United States Patent
Hay et al.

(10) Patent No.: US 11,370,778 B2
(45) Date of Patent: Jun. 28, 2022

(54) BIS(PENTAHYDROXYHEXYL)AMINO SUBSTITUTED 2-{[(3-AMINO-PYRAZIN-2-YL)FORMAMIDO]METHYL}-1H-1,3-BENZODIAZOL-3-IUM DERIVATIVES AS ENAC INHIBITORS FOR TREATING RESPIRATORY DISEASES

(71) Applicant: ENTERPRISE THERAPEUTICS LIMITED, Brighton (GB)

(72) Inventors: Duncan Alexander Hay, Abingdon (GB); Thomas Beauregard Schofield, Abingdon (GB); Naomi Went, Abingdon (GB); Clive McCarthy, Brighton (GB)

(73) Assignee: Enterprise Therapeutics Limited, Falmer (GB)

( * ) Notice: Subject to any disclaimer, the term of this patent is extended or adjusted under 35 U.S.C. 154(b) by 14 days.

(21) Appl. No.: 16/756,416

(22) PCT Filed: Oct. 17, 2018

(86) PCT No.: PCT/GB2018/052983
§ 371 (c)(1),
(2) Date: Apr. 15, 2020

(87) PCT Pub. No.: WO2019/077340
PCT Pub. Date: Apr. 25, 2019

(65) Prior Publication Data
US 2020/0239442 A1    Jul. 30, 2020

(30) Foreign Application Priority Data
Oct. 17, 2017    (GB) .................................... 1717051

(51) Int. Cl.
| | | |
|---|---|---|
| *C07D 401/14* | (2006.01) | |
| *C07D 403/12* | (2006.01) | |
| *C07D 403/14* | (2006.01) | |
| *A61P 11/00* | (2006.01) | |
| *A61K 45/06* | (2006.01) | |

(52) U.S. Cl.
CPC ............ *C07D 401/14* (2013.01); *A61P 11/00* (2018.01); *C07D 403/12* (2013.01); *C07D 403/14* (2013.01); *A61K 45/06* (2013.01)

(58) Field of Classification Search
CPC ... C07D 401/14; C07D 403/12; C07D 403/14
See application file for complete search history.

(56) References Cited

U.S. PATENT DOCUMENTS

| | | |
|---|---|---|
| 2015/0018313 A1 | 1/2015 | Kley et al. |
| 2015/0018314 A1 | 1/2015 | Kley et al. |

FOREIGN PATENT DOCUMENTS

| | | |
|---|---|---|
| WO | WO 03/070182 | 8/2003 |
| WO | WO 03/070184 | 8/2003 |
| WO | WO 2004/073629 | 9/2004 |
| WO | WO 2005/016879 | 2/2005 |
| WO | WO 2005/018644 | 3/2005 |
| WO | WO 2005/025496 | 3/2005 |
| WO | WO 2005/034847 | 4/2005 |
| WO | WO 2005/044180 | 5/2005 |
| WO | WO 2006/022935 | 3/2006 |
| WO | WO 2007/018640 | 2/2007 |
| WO | WO 2007/071396 | 6/2007 |
| WO | WO 2007/071400 | 6/2007 |
| WO | WO 2008/124491 | 10/2008 |

(Continued)

OTHER PUBLICATIONS

Howsham et al., "The discovery of novel inhaled ENaC blockers for the treatment of cystic fibrosis lung disease," Ch. 7 in *Ion Channel Drug Discovery*, published by Royal Society of Chemistry, Sep. 18, 2014 (26 pages).

(Continued)

*Primary Examiner* — Brian E McDowell
(74) *Attorney, Agent, or Firm* — Bookoff McAndrews, PLLC

(57) ABSTRACT

The present invention discloses bis(pentahydroxyhexyl) amino substituted 2-{[(3-amino-pyrazin-2-yl)formamido] methyl}-1H-1,3-benzodiazol-3-ium derivatives of formula (I) as inhibitors of ENaC and are of use in the treatment of respiratory diseases and conditions, skin conditions or ocular conditions, wherein the respiratory disease or condition is e.g. cystic fibrosis, chronic obstructive pulmonary disease (COPD), chronic bronchitis, emphysema, bronchiectasis, including non-cystic fibrosis bronchiectasis, and asthma; the skin condition is e.g. psoriasis, atopic dermatitis and ichthyosis; and the ocular condition is e.g. dry eye disease.

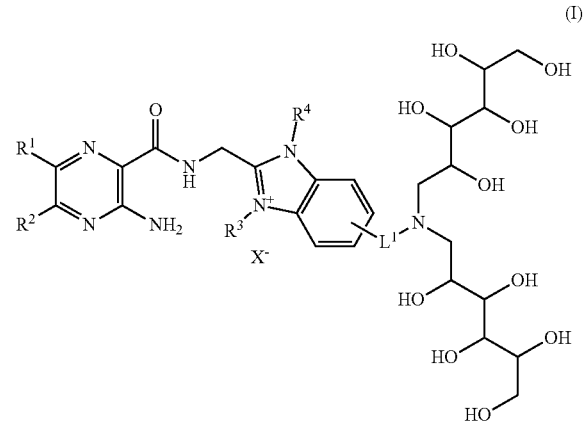

10 Claims, No Drawings

(56) References Cited

FOREIGN PATENT DOCUMENTS

| | | |
|---|---|---|
| WO | WO 2008/135557 | 11/2008 |
| WO | WO 2009/019506 | 2/2009 |
| WO | WO 2009/074575 | 6/2009 |
| WO | WO 2009/138378 | 11/2009 |
| WO | WO 2009/139948 | 11/2009 |
| WO | WO 2009/150137 | 12/2009 |
| WO | WO 2011/028740 | 3/2011 |
| WO | WO 2011/079087 | 6/2011 |
| WO | WO 2011/113894 | 9/2011 |
| WO | WO 2012/035158 | 3/2012 |
| WO | WO 2013/003386 | 1/2013 |
| WO | WO 2013/064450 | 5/2013 |
| WO | WO 2013/092674 | 6/2013 |
| WO | WO 2013/181232 | 12/2013 |
| WO | WO 2014/044849 | 3/2014 |
| WO | WO 2014/099673 | 6/2014 |
| WO | WO 2014/099676 | 6/2014 |
| WO | WO 2014/099705 | 6/2014 |
| WO | WO 2014/177469 | 11/2014 |
| WO | WO 2015/003083 | 1/2015 |
| WO | WO 2015/003958 | 1/2015 |
| WO | WO 2015/007516 | 1/2015 |
| WO | WO 2015/007517 | 1/2015 |
| WO | WO 2015/007519 | 1/2015 |
| WO | WO 2015/018754 | 2/2015 |
| WO | WO 2016/113167 | 7/2016 |
| WO | WO 2016/113168 | 7/2016 |
| WO | WO 2016/113169 | 7/2016 |
| WO | WO 2016/113170 | 7/2016 |
| WO | WO 2017/028926 | 2/2017 |
| WO | WO 2017/028927 | 2/2017 |
| WO | WO 2017/221008 | 12/2017 |
| WO | WO 2018/096325 | 5/2018 |

OTHER PUBLICATIONS

Knowles et al., "A Pilot Study Of Aerosolized Amiloride for The Treatment of Lung Disease In Cystic Fibrosis," *The New England Journal of Medicine*, 1990, 322(17):1189-94.

International Search Report in PCT/GB2018/052983 dated Dec. 4, 2018 (2 pages).

App et al., "Acute and Long-term Amiloride Inhalation in Cystic Fibrosis Lung Disease. A Rational Approach to Cystic Fibrosis Therapy," *Am Rev Respir Dis.*, 1990, 141(3):605-12.

Botero-Velez et al., "Brief Report: Liddle's Syndrome Revisited—A Disorder of Sodium Reabsorption in The Distal Tubule," *The New England Journal of Medicine*, 1994, 330(3):178-81.

Boucher, "Evidence for Airway Surface Dehydration as The Initiating Event in CF Airway Disease," *Journal of Internal Medicine*, 2007, 261(1):5-16.

Bowler et al., "Nebulised Amiloride in Respiratory Exacerbations of Cystic Fibrosis: A Randomised Controlled Trial," *Archives of Disease In Childhood*, 1995, 73(3):427-30.

Chang et al., "Mutations in Subunits of The Epithelial Sodium Channel Cause Salt Wasting With Hyperkalaemic Acidosis, Pseudohypoaldosteronism Type 1," *The Nature Publishing Group, Nature Genetics*, 1996, 12(3):248-53.

Coote et al., "Camostat Attenuates Airway Epithelial Sodium Channel Function in Vivo Through The Inhibition of A Channel-Activating Protease," *The Journal Of Pharmacology And Experimental Therapeutics*, 2009, 329(2):764-74.

Coote et al., "The Guinea-Pig Tracheal Potential Difference as an In Vivo Model for The Study Of Epithelial Sodium Channel Function in The Airways," *British Journal of Pharmacology*, 2008, 155(7):1025-33.

Fajac et al., "Nasal Airway Ion Transport Is Linked To The Cystic Fibrosis Phenotype In Adult Patients," *Thorax*, 2004, 59(11):971-76.

Frateschi et al., "The Epithelial Sodium Channel ENaC And Its Regulators in The Epidermal Permeability Barrier Function," *The Open Dermatology Journal*, 2010, 4: 27-35.

Graham et al., "No Added Benefit From Nebulized Amiloride in Patients With Cystic Fibrosis," *Eur Respir J.*, 1993, 6(9):1243-48.

Hirsh et al., "Pharmacological Properties of N-(3,5-diamino-6-chloropyrazine-2-carbonyl)-N'-4-[4-(2,3-dihydroxypropoxy)phenyl]butyl-guanidine Methanesulfonate (552-02), A Novel Epithelial Sodium Channel Blocker With Potential Clinical Efficacy for Cystic Fibrosis Lung Disease," *The Journal Of Pharmacology And Experimental Therapeutics*, Apr. 2008; 325(1):77-88.

Kellenberger, "Epithelial Sodium Channel/Degenerin Family of Ion Channels: A Variety of Functions For A Shared Structure," *Physiol Rev.*, 2002 82(3):735-67.

Kerem et al., "Pulmonary Epithelial Sodium-Channel Dysfunction And Excess Airway Liquid In Pseudohypoaldosteronism," *The New England Journal of Medicine*, 1999, 341(3):156-62.

Knowles et al., "Abnormal Ion Permeation Through Cystic Fibrosis Respiratory Epithelium," *Science*, 1983, 221(4615):1067-70.

Leal et al., "Airway Ion Transport Impacts on Disease Presentation and Severity in Cystic Fibrosis," *Science Direct, Clinical Biochemistry*, 2008, 41(10-11):764-72.

Matsui et al., "Evidence for Periciliary Liquid Layer Depletion, Not Abnormal Ion Composition, in the Pathogenesis of Cystic Fibrosis Airways Disease," *Cell*, 1998, 95(7):1005-15.

Middleton et al., "Effect Of Amiloride and Saline on Nasal Mucociliary Clearance and Potential Difference in Cystic Fibrosis and Normal Subjects," *Thorax*, 1993, 48(8):812-6.

Noone et al., "Airway Deposition and Clearance and Systemic Pharmacokinetics of Amiloride Following Aerosolization With an Ultrasonic Nebulizer to Normal Airways," *Chest*, 1997, 112(5):1283-90.

Paulekuhn et al., "Trends in Active Pharmaceutical Ingredient Salt Selection based on Analysis of the Orange Book Database," *J. Med. Chem.*, 2007, 50: 6665-6672.

Perazella, "Drug-Induced Hyperkalemia: Old Culprits and New Offenders," *Am J Med.*, 2000, 109(4):307-14.

Pons et al., "French Multicenter Randomized Double-Blind Placebo-Controlled Trial on Nebulized Amiloride in Cystic Fibrosis Patients," *Pediatric Pulmonology*, 2000, 30(1):25-31.

Schoenberger et al., "Novel Small Molecule Epithelial Sodium Channel Inhibitors as Potential Therapeutics in Cystic Fibrosis—A Patent Evaluation," *Expert Opinion Ther. Patents*, 2013, 23(10), 1383-89.

Thelin et al., "Effect of Topically Applied Epithelial Sodium Channel Inhibitors on Tear Production in Normal Mice and in Mice With Induced Aqueous Tear Deficiency," Journal of Ocular Pharmacology And Therapeutics, 2012, 28(4): 433-38.

BIS(PENTAHYDROXYHEXYL)AMINO SUBSTITUTED 2-{[(3-AMINO-PYRAZIN-2-YL)FORMAMIDO]METHYL}-1H-1,3-BENZODIAZOL-3-IUM DERIVATIVES AS ENAC INHIBITORS FOR TREATING RESPIRATORY DISEASES

This application is a U.S. National Stage filing under 35 U.S.C. § 371 of International Application No. PCT/GB2018/052983, filed on Oct. 17, 2018, which claims priority to GB 1717051.5, filed on Oct. 17, 2017.

The present invention relates to novel compounds which have activity as inhibitors of the epithelial sodium channel (ENaC). The invention also relates to the use of these compounds in treating diseases and conditions modulated by ENaC, particularly respiratory diseases and conditions, methods of preparing the compounds and pharmaceutical compositions containing them.

Humans can inhale up to 12,000 L of air each day and with it comes the potential for airborne pathogens (bacteria, viruses, fungal spores). To protect against these airborne pathogens, the lung has evolved innate defence mechanisms to minimise the potential for infection and colonisation of the airways. One such mechanism is the mucus clearance system, whereby secreted mucus is propelled up and out of the airways by the coordinated beating of cilia together with cough clearance. This ongoing 'cleansing' of the lung constantly removes inhaled particles and microbes thereby reducing the risk of infection.

In recent years it has become clear that the hydration of the mucus gel is critical to enable mucus clearance (Boucher 2007; Matsui et al, 1998). In a normal, healthy airway, the mucus gel is typically 97% water and 3% solids under which conditions the mucus is cleared by mucociliary action. The hydration of the airway mucosa is regulated by the coordinated activity of a number of ion channels and transporters. The balance of anion ($Cl^-/HCO_3^-$) secretion mediated via the Cystic Fibrosis Transmembrane Conductance Regulator (CFTR) and the Calcium Activated Chloride Conductance (CaCC; TMEM16A) and $Na^+$ absorption through the epithelial $Na^+$ channel (ENaC) determine the hydration status of the airway mucosa. As ions are transported across the epithelium, water is osmotically obliged to follow and thus fluid is either secreted or absorbed.

In respiratory diseases such as chronic bronchitis and cystic fibrosis, the % solids of the mucus gel is increased as the hydration is reduced and mucus clearance is reduced (Boucher, 2007). In cystic fibrosis, where loss of function mutations in CFTR attenuates ability of the airway to secrete fluid, the % solids can be increased to 15% which is believed to contribute towards the plugging of small airways and failure of mucus clearance. Furthermore, in cystic fibrosis an increase in ENaC activity has been reported by several groups (Knowles et al, 1983; Middleton et al, 1993) and this increase in ENaC function has been shown to correlate with disease severity (Fajac et al, 2004; Leal et al, 2008). Strategies to increase the hydration of the airway mucus include either the stimulation of anion and thereby fluid secretion or the inhibition of $Na^+$ absorption. To this end, blocking the activity of ENaC will inhibit $Na^+$ absorption and therefore increase fluid accumulation in the airway mucosa, hydrate mucus and enhance mucus clearance mechanisms.

ENaC is expressed in renal, colonic, corneal, sweat duct and respiratory epithelia where it forms a low conductance channel (~4 pS) with a selectivity for $Na^+$ over $K^+$ of approximately 10-fold (Kellenberger 2002). Loss and gain of function mutations in the channel can cause human disease including pseudohypoaldosteronism type 1 (PHA1), a salt wasting disease (Chang et al, 1996), and Liddles's syndrome, a disease associated with salt retention and hypertension (Botero-Velez et al, 1994). Of particular note to lung physiology is the observation that patients with PHA1 loss-of-function mutations in ENaC have an enhanced rate of airway mucociliary clearance (MCC) compared with the normal healthy population, typically 3-4 fold faster (Kerem et al, 1999). Furthermore the upper airways of these patients appear to be 'wet' and have extra-hydration compared to normal. These observations further support the salient role that ENaC plays in the human airway in the regulation of hydration and the therapeutic benefit that blocking ENaC in the airway could deliver in terms of enhancing MCC and innate defence.

Amiloride, a small compound blocker of ENaC, has been demonstrated to increase MCC in both healthy controls and also patients with CF, further supporting the physiological significance of this mechanism (App et al, 1990). However, the lack of a robust effect of inhaled amiloride on clinical endpoints (Bowler et al, 1995; Graham et al, 1993; Knowles et al, 1990; Pons et al, 2000) was ascribed to the short duration of action of this compound in the lungs (Noone et al., 1997). Novel ENaC blockers, specifically designed for a long duration of action in the airway are therefore predicted to acutely provide an extended enhancement of MCC with resulting clinical benefit in the longer term.

A challenge with the design of inhaled ENaC blockers for the treatment of respiratory diseases has been the potential for the renal-based side effect of hyperkalaemia (Perazela et al., 2000). ENaC is expressed in the cortical collecting duct of the kidney epithelium and block of the channel here can lead to a systemic accumulation of $K^+$. For this reason, it is desirable that an inhaled ENaC blocker minimises renal exposure following absorption from the lung. This could be achieved through either a high lung retention of ENaC blocker therefore enabling only a low dose to be administered or through the design of a compound that will be rapidly broken down before it reaches the kidney.

ENaC blockers have also been implicated in the hydration of skin and the surface of the eye (Frateschi et al, 2010; Thelin et al, 2012).

Several ENaC blockers are known. For example, WO 2011/079087 relates to compounds of the formula:

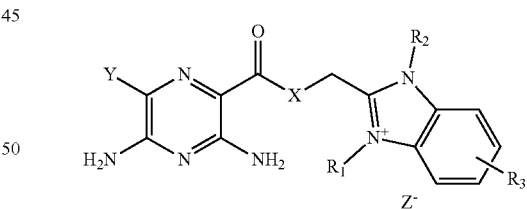

WO 2015/007516, WO 2015/007517 and WO 2015/007519 all relate to compounds of the formula:

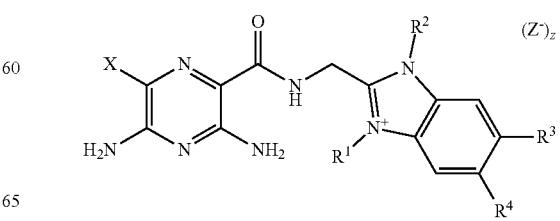

WO 2016/113168, WO 2016/113167 and WO 2016/113169 relate to compounds of the formula:

WO 2016/113170 relates to compounds of the formula:

Similar ENaC inhibitors are disclosed in WO2013/0664450, WO2013/092674, WO2014/044849, WO 2014/177469, WO 2015/003958, WO2015/018754, WO 2011/028740, WO 2007/071396, WO 2007/071400, WO 2008/135557, WO 2009/074575, WO 2009/138378, WO 2009/150137, WO 2012/035158, WO 2015/003083, WO 2004/073629, WO 03/070184, WO 03/070182, WO 2006/022935, WO 2007/018640, WO 2008/124491, WO 2009/139948, WO 2005/044180, WO 2005/016879, WO 2005/018644, WO 2005/025496, WO 2005/034847 and WO 2013/181232.

Our co-pending international patent application no. PCT/GB2017/051815 and our UK patent application no. 1619694.1 also relate to ENaC inhibiting compounds.

The present inventors have surprisingly discovered that compounds derivatised with sugar residues show prolonged retention in the lung which can be assessed by measuring drug levels in the epithelial lining fluid (ELF) at various timepoints after administration. This prolonged lung retention allows a smaller dose of compound to be administered with concommitent reduction in kidney exposure.

In the present invention there is provided a compound of general formula (I) including all tautomeric forms, all enantiomers and isotopic variants and salts thereof:

(I)

wherein
$X^-$ is an anion;
$R^1$ is halo, cyano, $C_{1-3}$ alkyl, $C_{1-3}$ haloalkyl, or —S($C_{1-3}$ alkyl);
$R^2$ is H or $NH_2$;
each of $R^3$ and $R^4$ is independently $C_{1-10}$ alkyl, wherein one or more —$CH_2$— groups is optionally replaced by —O—, —S— or —$NR^5$—, provided that adjacent —$CH_2$— groups are not so replaced, and which is optionally substituted with one or more substituents selected from halo, —$OR^6$, —$SR^6$, —$NR^6R^7$, aryl, heteroaryl, cycloalkyl, heterocyclyl, —C(O)$OR^6$ and —C(O)$NR^6R^7$;
wherein each $R^5$, $R^6$ and $R^7$ is independently selected from H or $C_{1-4}$ alkyl;
$L^1$ is:
—$Z^1$—, -$Q^1$-, —$Z^1Q^1$-, -$Q^1Z^1$—, —$Z^1Q^1Z^2$—, -$Q^1Q^2$-, -$Q^1Q^2Z^1$, -$Q^1Q^2Z^1Q^3Z^2$—, —$Z^1Q^1Q^2OQ^3$-;
—$OZ^1$—, —$OQ^1$-, —$OZ^1Q^1$-, —$OQ^1Z^1$—, —$OZ^1Q^1Z^2$—, —$OQ^1Q^2$-, —$OQ^1Q^2Z^1$—, —$OQ^1Q^2Z^1Q^3Z^2$—, —$OZ^1Q^1OQ^2OQ^3$-;
—$NR^8Z^1$—, —$NR^8Q^1$, —$NR^8Z^1Q^1$-, —$NR^8Q^1Z^1$—, —$NR^8Z^1Q^1Z^2$—, —$NR^8Q^1Q^2$-, —$NR^8Q^1Q^2Z^1$—, —$NR^8Q^1Q^2Z^1Q^3Z^2$—, —$NR^8Z^1Q^1OQ^2OQ^3$-;
—$Z^1NR^8Z^2$—, -$Q^1Z^1NR^8Z^2$—, —$Z^1NR^8Z^2Q^1$-, -$Q^1Z^1NR^8Z^2Q^2Z^3$—; —$Z^1O(CH_2CH_2O)_nZ^2$—, —$Z^1O(CH_2CH_2O)_nQ^1$-, —$Z^1O(CH_2CH_2O)_nZ^2Q^1$, —$Z^1O(CH_2CH_2O)_nQ^1Z^2$—, -$Q^1Z^1O(CH_2CH_2O)_nZ^2$—, -$Q^1Z^1O(CH_2CH_2O)_nQ^1$-, -$Q^1Z^1O(CH_2CH_2O)_nZ^2Q^1$—, —$Z^1O(CH_2CH_2O)_nZ^2Q^1Z^3$—
—C(O)$Z^1$—, —C(O)$Q^1$-, —C(O)$Z^1Q^1$-, —C(O)$Z^1Q^1Z^2$—, —C(O)$Q^1Z^1$—, —C(O)$Q^1Q^2$-, —C(O)$Q^1Q^2Z^1$—, —C(O)$Q^1NR^8C(O)Z^1$—, —C(O)$Q^1NR^8C(O)Z^1Q^2$-, —C(O)$Q^1NR^8C(O)Z^1Q^2Q^3$- —C(O)$Q^1NR^8C(O)Z^1Q^2Z^2$—, —C(O)$Z^1Q^1OQ^2OQ^3$-;
—C(O)$NR^8Z^1$—, —C(O)$NR^8Q^1$-, —C(O)$NR^8Z^1Q^1$-, —C(O)$NR^8Z^1Q^1Z^2$—, —C(O)$NR^8Q^1Z^1$—, —C(O)$NR^8Q^1Q^2$-, —C(O)$NR^8Q^1Q^2Z^1$—, —C(O)$NR^8Z^1Q^1Q^2Z^2$—, —C(O)$NR^8(CH_2CH_2)_nZ^1$— —C(O)$NR^8Z^1O(CH_2O)_nZ^2$—, —C(O)$NR^8Z^1Q^1Z^2NR^9Z^3$—, —C(O)$NR^8Z^1NR^9Z^2$—, —C(O)$NR^8Q^1Z^1NR^9Z^2$—, —C(O)$NR^8Z^1Q^1OQ^2OQ^3$-, —C(O)$NR^8Z^1Q^1OQ^2OQ^3Z^2$—;
—$Z^1C(O)NR^8Z^2$—, —$Z^1C(O)NR^8Q^1$-, —$Z^1C(O)NR^8Z^2Q^1$-, —$Z^1C(O)NR^8Q^1Z^2$—, —$Z^1C(O)NR^8Q^1Q^2$-, —$Z^1C(O)Q^1$-, —$Z^1C(O)Q^1Z^2$—, —$Z^1C(O)Q^1Q^2$-, —$Z^1C(O)NR^8Q^1Q^2Z^2$—;
—C(O)$OZ^1$—, —C(O)$OQ^1$-, —C(O)$OZ^1Q^1$-, —C(O)$OZ^1Q^1Z^2$—, —C(O)$OQ^1Z^1$—, —C(O)$OQ^1Q^2$-, —C(O)$OQ^1Q^2Z^1$—;
-$Q^1C(O)Q^2$-, $Q^1C(O)Z^1$—, -$Q^1C(O)Q^2Z^1$—, $Q^1C(O)Q^2Q^3$-, $Q^1C(O)Z^1Q^2$-, $Q^1C(O)Q^2Q^3Z^1$—; —C(=$NR^{10}$)$NR^8Z^1$—, —C(=$NR^{10}$)$NR^8Q^1$-, —C(=$NR^{10}$)$NR^8Z^1Q^1$-, —C(=$NR^{10}$)$NR^8Z^1Q^1Z^2$—, —C(=$NR^{10}$)$NR^8Q^1Z^1$—, —C(=$NR^{10}$)$NR^8Q^1Q^2$-, C(=$NR^{10}$)$NR^8Q^1Q^2Z^1$—;
each of $Z^1$, $Z^2$ and $Z^3$ is independently $C_{1-12}$ alkylene, $C_{2-12}$ alkenylene, $C_{2-12}$ alkynylene any of which is optionally substituted by one or more halo, OH, C(O)$NR^{11}R^{12}$, C(O)$OR^{11}$ or $NR^{11}R^{12}$;
each $R^{11}$ and $R^{12}$ is independently H or $C_{1-6}$ alkyl;
each of $Q^1$, $Q^2$ and $Q^3$ is independently carbocyclyl, heterocyclyl, aryl or heteroaryl any of which is optionally substituted with one or more substituents selected from halo, OH, C(O)$NR^{11}R^{12}$, C(O)$OR^{11}$ or $NR^{11}R^{12}$, or, for cycloalkyl and heterocyclyl groups, oxo, wherein $R^{11}$ and $R^{12}$ are as defined above;
n is 1 to 6;

each $R^8$ and $R^9$ is independently selected from H or $C_{1-12}$ alkyl optionally substituted with one or more halo or OH groups, or when an $R^8$ and an $R^9$ or two $R^9$ groups are attached to a nitrogen atom they may, together with the nitrogen atom combine to form a 5- or 6-membered heterocyclic ring optionally comprising one or more further heteroatoms selected from N, O and S;

$R^{10}$ is H or $C_{1-6}$ alkyl.

The compounds of general formula (I) have ENaC blocking activity and, in particular excellent retention time in the epithelial lining of the lungs. It appears that this advantageous property is conferred by the presence of the sugar residues.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

In the present specification, references to "pharmaceutical use" refer to use for administration to a human or an animal, in particular a human or a mammal, for example a domesticated or livestock mammal, for the treatment or prophylaxis of a disease or medical condition. The term "pharmaceutical composition" refers to to a composition which is suitable for pharmaceutical use and "pharmaceutically acceptable" refers to an agent which is suitable for use in a pharmaceutical composition. Other similar terms should be construed accordingly.

In the context of the present specification, the term "plurality" refers to two or more.

The anion $X^-$ can have any negative charge and will be balanced by the appropriate number of cations. Thus, for example, a compound of general formula (I) in which $X^-$ is an anion having a single negative charge will have a 1:1 ratio of cation:anion whereas if the anion $X^-$ has a charge of –2, the ratio of cation:anion in the compound of general formula (I) will be 2:1. The anion $X^-$ is suitably a pharmacologically acceptable anion, although other anions may also be useful, particularly in synthetic precursors to the compounds of general formula (I). Suitable anions, $X^-$ include halide, sulfate, nitrate, phosphate, formate, acetate, trifluoroacetate, fumarate, citrate, tartrate, oxalate, succinate, mandelate, methane sulfonate and p-toluene sulfonate. Alternatively, the counter ion $X^-$ may be part of the structure of the compound such that the compound of general formula (I) is a zwitterion. This may be the case, for example, when the compound comprises a carboxyl group.

All of the compounds of general formula (I) are salts. In the present specification, references to salts of the compounds of formula (I) refer to salts of an additional basic nitrogen atom, for example the nitrogen atom to which the sugar moieties are attached. Counter ions for such salts are as defined for $X^-$.

Alternatively, when the compound of general formula (I) comprises a carboxyl group C(O)OH, salts may be formed. Suitable counter ions for such salts include sodium, potassium, calcium, aluminium, zinc, magnesium and other metal ions as well as choline, diethanolamine, ethanolamine, ethyl diamine, megulmine and other well-known basic addition salts as summarised in Paulekuhn et al., (2007) *J. Med. Chem.* 50: 6665-6672 and/or known to those skilled in the art.

In the present specification, the term "$C_{1-6}$" alkyl refers to a straight or branched fully saturated hydrocarbon group having from 1 to 6 carbon atoms. The term encompasses methyl, ethyl, n-propyl, isopropyl, n-butyl, isobutyl and t-butyl. Other alkyl groups, for example $C_{1-12}$ alkyl and $C_{1-4}$ alkyl are as defined above but contain 1 to 12 and 1 to 4 carbon atoms respectively.

The term "$C_{2-6}$ alkenyl" refers to a straight or branched hydrocarbon group having from 2 to 6 carbon atoms and at least one carbon-carbon double bond. Examples include ethenyl, prop-1-enyl, hex-2-enyl etc. Other alkenyl groups, for example $C_{1-12}$ alkenyl are as defined above except that they contain the specified number (e.g. 2 to 12) carbon atoms.

The term "$C_{2-6}$ alkynyl" refers to a straight or branched hydrocarbon group having from 2 to 6 carbon atoms and at least one carbon-carbon triple bond. Examples include ethynyl, prop-1-ynyl, hex-2-ynyl etc. Other alkynyl groups, for example $C_{2-12}$ alkynyl are as defined above except that they contain the specified number (e.g. 2 to 12) carbon atoms.

The term "$C_{1-6}$ alkylene" refers to a straight or branched fully saturated hydrocarbon chain having from 1 to 6 carbon atoms. Examples of alkylene groups include —$CH_2$—, —$CH_2CH_2$—, $CH(CH_3)$—$CH_2$—, $CH_2CH(CH_3)$—, —$CH_2CH_2CH_2$—, —$CH_2CH(CH_2CH_3)$— and —$CH_2CH(CH_2CH_3)CH_2$—. Other alkylene groups, for example $C_{1-12}$ alkylene are as defined above except that they contain the specified number (e.g. 1 to 12) carbon atoms.

The term "$C_{2-6}$ alkenylene" refers to a straight or branched hydrocarbon chain containing from 2 to 6 carbon atoms and at least one carbon-carbon double bond. Examples of alkenylene groups include —CH=CH—, —CH=C(CH_3)—, —$CH_2$CH=CH—, —CH=CH$CH_2$—, $CH_2CH_2$CH=CH—, $CH_2$CH=C(CH_3)— and —$CH_2$CH=C($CH_2CH_3$)—. Other alkenylene groups, for example $C_{2-12}$ alkenylene, are as defined above except that they contain the specified number (e.g. 2 to 12) carbon atoms.

The term "$C_{2-6}$ alkynylene" refers to a straight or branched hydrocarbon chain containing from 2 to 6 carbon atoms and at least one carbon-carbon triple bond. Examples of alkenylene groups include —C≡C—, —$CH_2$C≡C—, —C≡C—$CH_2$—, $CH_2CH_2$C≡C—, $CH_2$C≡C$CH_2$— and —$CH_2$CH≡C—$CH_2CH_2$—)—. Other alkynylene groups, for example $C_{2-12}$ alkynylene, are as defined above except that they contain the specified number (e.g. 2 to 12) carbon atoms.

The terms "carbocyclic" and "carbocyclyl" refer to a non-aromatic hydrocarbon ring system containing from 3 to 10 ring carbon atoms, unless otherwise indicated, and optionally one or more double bond. The carbocyclic group may be a single ring or may contain two or three rings which may be fused or bridged. Examples include cyclopropyl, cyclobutyl, cyclopentyl, cyclohexyl, cyclopentenyl and cyclohexenyl.

In the context of the present specification, the terms "heterocyclic" and "heterocyclyl" refer to a non-aromatic ring system containing 3 to 10 ring atoms including at least one heteroatom selected from N, O and S. The heterocyclic group may be a single ring or may contain two or three rings which may be fused or bridged. Examples include tetrahydrofuranyl, tetrahydroypranyl, pyrrolidine, piperidinyl, morpholinyl, piperazinyl and thiomorpholinyl.

The terms "aryl" and "aromatic" in the context of the present specification refer to a ring system with aromatic character having from 5 to 14 ring carbon atoms and containing up to three rings. Where an aryl group contains more than one ring, not all rings must be fully aromatic in character. Examples of aromatic moieties are benzene, naphthalene, fluorene, indane and indene.

The terms "heteroaryl" and "heteroaromatic" in the context of the specification refer to a ring system with aromatic character having from 5 to 14 ring atoms, at least one of which is a heteroatom selected from N, O and S, and containing up to three rings. Where a heteroaryl group contains more than one ring, not all rings must be fully aromatic in character. Examples of heteroaryl groups include pyridine, pyrimidine, indole, benzofuran, benzimidazole and indolene.

The term "halogen" refers to fluorine, chlorine, bromine or iodine and the term "halo" to fluoro, chloro, bromo or iodo groups.

The term "$C_{1-6}$ haloalkyl" as used herein refers to a $C_{1-6}$ alkyl group as defined above in which one or more of the hydrogen atoms is replaced by a halo group. Any number of hydrogen atoms may be replaced, up to perhalo substitution. Examples include trifluoromethyl, chloroethyl and 1,1-difluoroethyl. Other haloalkyl groups, for example $C_{1-12}$ haloalkyl are as defined above except that they contain the specified number (e.g. 1 to 12) carbon atoms.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as 2H (deuterium), 3H, 11C, 13C, 14C, 18F, 123I or 125I (e.g. 3H, 11C, 14C, 18F, 123I or 125I), which may be naturally occurring or non-naturally occurring isotopes.

The concept of canonical forms is well understood by the person of skill in the art. Thus, a compound of general formula (I) can have canonical forms as follows:

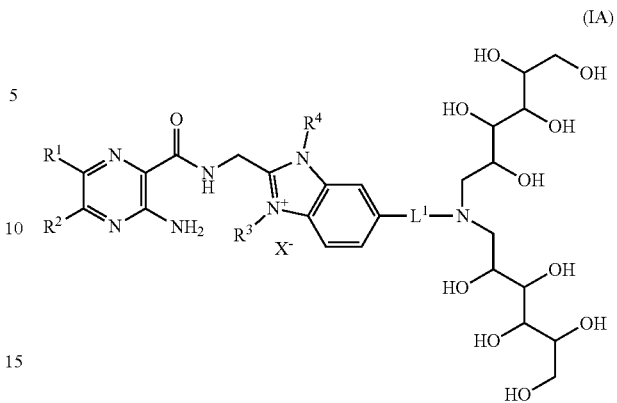

wherein $R^1$, $R^2$, $R^3$, $R^4$, $L^1$ and $X^-$ are as defined for general formula (I); or a compound of general formula (IB):

(IB)

wherein $R^1$, $R^2$, $R^3$, $R^4$, $L^1$ and $X^-$ are as defined for general formula (I).

both of which are included within the scope of the invention.

The $L^1$ linker is suitably at the 5- or the 6-position and thus the compound of general formula (I) can be a compound of general formula (IA):

Compounds of general formula (IA) are particularly suitable, although it should be noted that, because the compound of general formula (I) can have different canonical forms as discussed above, if $R^3$ and $R^4$ are the same then the 5- and 6-positions are equivalent.

In the compounds of general formula (I), (IA) and (IB), $R^1$ is suitably halo, methyl or cyano, and more suitably halo or methyl, and especially halo such as chloro or bromo.

Suitably, in compounds of general formulae (I), (IA) and (IB), $R^2$ is $NH_2$.

As mentioned above, each of $R^3$ and $R^4$ is $C_{1-10}$ alkyl in which one or more —$CH_2$— groups is optionally replaced by —O—, —S— or —$NR^5$— and which is optionally substituted as defined above.

Suitably, each of $R^3$ and $R^4$ is $C_{1-10}$ alkyl in which one or more —$CH_2$— groups is optionally replaced by —O—, —S— and which is optionally substituted as defined above.

More suitable substituents for $R^3$ and $R^4$ include OH, SH, halo, $NR^6R^7$, $C(O)OR^6$, $C(O)NR^6R^7$, phenyl or pyridyl, where $R^6$ and $R^7$ are as defined above. Particularly suitable substituents for $R^3$ include OH, SH, phenyl or pyridyl, particularly OH, phenyl, pyridyl, $C(O)O$—$C_{1-6}$ alkyl, $C(O)$OH or $C(O)NR^6R^7$, where each of $R^6$ and $R^7$ is H or $C_{1-3}$ alkyl.

In more suitable compounds of general formula (I), each or $R^3$ and $R^4$ is $C_{1-10}$ alkyl, $C_{1-10}$ alkyl-OH, $(CH_2CH_2O)_t$—$CH_3$, $(CH_2CH_2O)_t$—H, $(CH_2CH_2CH_2O)_t$—$CH_3$ or $(CH_2CH_2CH_2O)_t$—H; wherein s is 0-9; and t is 1-3.

Still more suitable examples of $R^3$ and $R^4$ groups include —$(CH_2)_sCH_3$, —$(CH_2)_sOH$, $(CH_2CH_2O)_t$—$CH_3$ or $(CH_2CH_2O)_t$—H, any of which is optionally substituted as defined above; and wherein s is 0-9, more suitably 0-6 and still more suitably 0-3; and t is 1-3, especially 2 or 3.

In some compounds of general formula (I), at least one of $R^3$ and $R^4$ is —$(CH_2)_sCH_3$, wherein s is 0-9, more suitably 0-6 and still more suitably 0-3; and t is 1-3, especially 2 or 3, and is optionally substituted with a single substituent as defined above. Optionally both $R^3$ and $R^4$ are —$(CH_2)_sCH_3$, wherein s is 0-9, more suitably 0-6 and still more suitably 0-3; and t is 1-3, especially 2 or 3, optionally substituted with a single substituent as defined above.

In some such compounds of general formula (I) one of or both of $R^3$ and $R^4$ are methyl, ethyl, benzyl, pyridylmethyl, —$CH_2OH$, —$CH_2NH_2$, —$CH_2CH_2OH$ or $CH_2CH_2NH_2$.

In other suitable compounds of general formula (I), both $R^3$ and $R^4$ are $C_{1-10}$ alkyl, more suitably both $R^3$ and $R^4$ are $C_{1-6}$ alkyl, for example methyl, ethyl or n-propyl, particularly ethyl.

In other particularly suitable compounds, at least one of $R^3$ and $R^4$ is —$CH_2CH_2OCH_2CH_2OH$ or —$CH_2CH_2OCH_2CH_2OCH_2CH_2OH$ In some suitable compounds of general formula (I), (IA), and (IB), $L^1$ is:
—$C(O)Z^1$—, —$C(O)Q^1$-, —$C(O)Z^1Q^1$-, —$C(O)Z^1Q^1Z^2$—, —$C(O)Q^1Z^1$—, —$C(O)Q^1Q^2$-, —$C(O)Q^1Q^2Z^1$—, —$C(O)Q^1NR^8C(O)Z^1$—, —$C(O)Q^1NR^8C(O)Z^1Q^2$-, —$C(O)Q^1NR^8C(O)Z^1Q^2Q^3$- —$C(O)Q^1NR^8C(O)Z^1Q^2Z^2$—, —$C(O)Z^1Q^1Q^2OQ^3$-;
—$C(O)NR^8Z^1$—, —$C(O)NR^8Q^1$-, —$C(O)NR^8Z^1Q^1$-, —$C(O)NR^8Z^1Q^1Z^2$—, —$C(O)NR^8Q^1Z^1$—, —$C(O)NR^8Q^1Q^2$-, —$C(O)NR^8Q^1Q^2Z^1$—, —$C(O)NR^8Z^1Q^1Q^2Z^2$—, —$C(O)NR^8(CH_2CH_2O)_nZ^1$— —$C(O)NR^8Z^1O(CH_2O)_nZ^2$—, —$C(O)NR^8Z^1Q^1Z^2NR^9Z^3$—, —$C(O)NR^8Z^1NR^9Z^2$—, —$C(O)NR^8Q^1Z^1NR^9Z^2$—, —$C(O)NR^8Z^1Q^1OQ^3$-, —$C(O)NR^8Z^1Q^1Q^2OQ^32Z^2$—;

More suitably, $L^1$ is —$C(O)Q^1$-, $C(O)Q^1Z^1$—, —$C(O)Q^1Q^2$-, —$C(O)Q^1Q^2Z^1$—, —$C(O)NR^8Z^1$—, —$C(O)NR^8Q^1$-, —$C(O)NR^8Z^1Q^1Z^2$—, —$C(O)NR^8Z^1Q^1Q^2Z^2$—, —$C(O)NR^8(CH_2CH_2O)_nZ^1$— or —$C(O)NR^8Z^1O(CH_2O)_nZ^2$—.

In still more suitable compounds of the invention, $L^1$ is —$C(O)Q^1$-, $C(O)Q^1Z^1$—, —$C(O)NR^8Z^1$—, —$C(O)NR^8Z^1Q^1Z^2$—, —$C(O)NR^8Z^1Q^1Q^2Z^2$—, —$C(O)NR^8(CH_2CH_2O)_nZ^1$— or —$C(O)NR^8Z^1O(CH_2O)_nZ^2$—.

In particularly suitable compounds of the invention, $L^1$ is —$C(O)Q^1$-, —$C(O)Q^1Z^1$—, —$C(O)NR^8Z^1$—, —$C(O)NR^8Z^1Q^1Q^2Z^2$—, —$C(O)NR^8(CH_2CH_2O)_nZ^1$—

Suitably, where the linker moiety $L^1$ comprises one or more cyclic groups $Q^1$, $Q^2$ and $Q^3$, these cyclic groups are independently selected from 5- and 6-membered aryl or heteroaryl groups and 4 to 8-membered carbocyclic and heterocyclic groups.

In some more suitable compounds, $Q^1$, $Q^2$ and $Q^3$ are selected from 5- to 7-membered heterocyclyl groups, suitably nitrogen-containing heterocyclyl groups which optionally comprise one or more further heteroatoms.

Examples of such heterocyclic $Q^1$, $Q^2$ and $Q^3$ groups include azetidinyl, piperidinyl, pyrrolidinyl, piperazinyl, and aziridinyl, with 5- and 6-membered rings such as pyrrolidinyl, piperazinyl and piperidinyl being more suitable.

When $L^1$ comprises a C(O) moiety linked to a Q moiety, the Q moiety is suitably a nitrogen-containing heterocyclic ring in which a ring nitrogen atom is linked to the carbonyl moiety. For example, the Q moiety may be pyrrolidin-1-yl, piperidin-1-yl or piperazin-1-yl.

For example, in —$C(O)Q^1$-, —$C(O)Q^1Z^1$—, —$C(O)Q^1Q^2$-, —$C(O)Q^1Q^2Z^1$—, —$C(O)Q^1NR^8C(O)Z^1$—, —$C(O)Q^1NR^8C(O)Z^1Q^2$-, —$C(O)Q^1NR^8C(O)Z^1Q^2Q^3$-, —$C(O)Q^1NR^8C(O)Z^1Q^2Z^2$—, $Q^1$ is suitably a 5- or 6-membered heterocyclic ring which is linked to the —C(O) moiety via a ring nitrogen atom. Suitably, $Q^1$ is pyrrolidin-1-yl, piperidin-1-yl or piperazin-1-yl. When $Q^1$ is piperidin-1-yl or piperazin-1-yl, the remainder of the molecule is suitably linked to the 4-position of the ring and when $Q^1$ is pyrrolidine-1-yl, the remainder of the molecule is suitably linked to the 3-position of the ring.

In some compounds of the invention, $L^1$ is -$Q^1C(O)Q^2$-, -$Q^1C(O)Q^2Z^1$—, $Q^1C(O)Q^2Q^3$-, $Q^1C(O)Q^2Q^3Z^1$—, and $Q^2$ is suitably a 5- or 6-membered heterocyclic ring which is linked to the —C(O) moiety via a ring nitrogen atom. Suitably, $Q^2$ is pyrrolidin-1-yl, piperidin-1-yl or piperazin-1-yl. When $Q^2$ is piperidin-1-yl or piperazin-1-yl, the remainder of the molecule is suitably linked to the 4-position of the ring and when $Q^2$ is pyrrolidine-1-yl, the remainder of the molecule is suitably linked to the 3-position of the ring.

In compounds of the invention in which $L^1$ comprises a —$C(O)NR^8$ moiety linked to a Q moiety, the Q moiety is suitably a heterocyclic ring, e.g. a 5- or 6-membered nitrogen-containing heterocyclic ring, which is linked to the —$C(O)NR^8$— moiety via a ring carbon atom.

For example, when $L^1$ is —$C(O)NR^8Q^1$-, —$C(O)NR^8Q^1Z^1$—, —$C(O)NR^8Q^1Q^2$-, —$C(O)NR^8Q^1Q^2Z^1$—, —$C(O)NR^8Q^1Z^1NR^9Z^2$—, —$Z^1C(O)NR^8Q^1$-, —$Z^1C(O)NR^8Q^1Z^2$— or —$Z^1C(O)NR^8Q^1Q^2$-, $Q^1$ is suitably a 5- or 6-membered heterocyclic ring which is linked to the —$C(O)NR^8$— moiety via a ring carbon atom. Suitably, $Q^1$ is piperidin-4-yl and the remainder of the molecule is linked to the 1-position of the piperidine ring.

For other $L^1$ groups in which $Q^1$ and/or $Q^2$ and/or $Q^2$ is piperidinyl, they are suitably either piperidin-1-yl or piperidin-4-yl.

In other suitable compounds, one or more of $Q^1$, $Q^2$ and $Q^3$ is a 5- or 6-membered aryl or heteroaryl group. Examples of such groups include phenyl, pyridyl, pyrrolyl and imidazolyl, with phenyl being particularly suitable.

When the $L^1$ comprises a -$Q^1Q^2$- or -$Q^2Q^3$- moiety, this may be, for example:

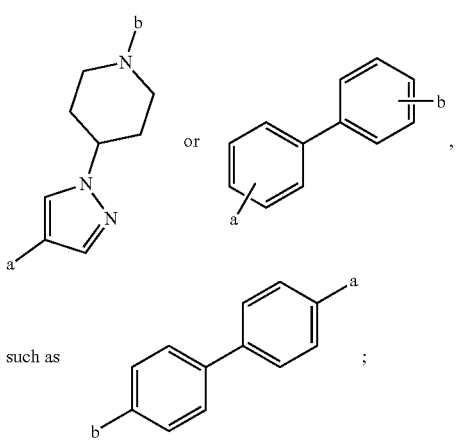

where a and b show the links to the remainder of the molecule.

Particularly suitable salts of the invention include the following, where the numbers relate to the numbers of the examples below:
1. 6-(4-{bis[(2S,3R,4R,5R)-2,3,4,5,6-pentahydroxyhexyl]amino}piperidine-1-carbonyl)-2-{[(3,5-diamino-6-chloropyrazin-2-yl)formamido]methyl}-1,3-diethyl-1H-1,3-benzodiazol-3-ium;
2. 2-{[(3-amino-6-bromopyrazin-2-yl)formamido]methyl}-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium;
3. 6-[4-({bis[(2S,3R,4R,5R)-2,3,4,5,6-pentahydroxyhexyl]amino}methyl)piperidine-1-carbonyl]-2-{[(3,5-diamino-6-chloropyrazin-2-yl)formamido]methyl}-1,3-diethyl-1H-1,3-benzodiazol-3-ium;
4. 6-[(3R)-3-{bis[(2S,3R,4R,5R)-2,3,4,5,6-pentahydroxyhexyl]amino}pyrrolidine-1-carbonyl]-2-{[(3,5-diamino-6-chloropyrazin-2-yl)formamido]methyl}-1,3-diethyl-1H-1,3-benzodiazol-3-ium;
5. 6-[(2-{bis[(2S,3R,4R,5R)-2,3,4,5,6-pentahydroxyhexyl]amino}ethyl)carbamoyl]-2-{[(3,5-diamino-6-chloropyrazin-2-yl)formamido]methyl}-1,3-diethyl-1H-1,3-benzodiazol-3-ium;
6. 2-{[(3,5-diamino-6-chloropyrazin-2-yl)formamido]methyl}-1,3-diethyl-6-{[(14S,15R,16R,17R)-14,15,16,17,18-pentahydroxy-12-[(2S,3R,4R,5R)-2,3,4,5,6-pentahydroxyhexyl]-3,6,9-trioxa-12-azaoctadecan-1-yl]carbamoyl}-1H-1,3-benzodiazol-3-ium;
7. 6-({2-[4'-(2-{bis[(2S,3R,4R,5R)-2,3,4,5,6-pentahydroxyhexyl]amino}ethyl)-[1,1'-biphenyl]-4-yl]ethyl}carbamoyl)-2-{[(3,5-diamino-6-chloropyrazin-2-yl)formamido]methyl}-1,3-diethyl-1H-1,3-benzodiazol-3-ium.

Suitable counter ions for the salts of the invention are as described above with formate, acetate and trifluororacetate anions being particularly suitable. In some cases, the specific salts of the invention mentioned above have a trifluoroacetate counter ion.

Compounds of general formula (I) in which $L^1$ is —C(O)$Z^1$—, —C(O)$Q^1$-, —C(O)$Z^1Q^1$-, —C(O)$Z^1Q^1Z^2$—, —C(O)$Q^1Z^1$—, —C(O)$Q^1Q^2$-, —C(O)$Q^1Q^2Z^1$—, —C(O)$Q^1NR^8C(O)Z^1$—, —C(O)$Q^1NR^8C(O)Z^1Q^2$-, —C(O)$Q^1NR^8C(O)Z^1Q^2Q^3$-, —C(O)$Q^1NR^8C(O)Z^1Q^2Z^2$—, —C(O)$Z^1Q^1OQ^2OQ^3$-; —C(O)$NR^8Z^1$—, —C(O)$NR^8Q^1$-, —C(O)$NR^8Z^1Q^1$-, —C(O)$NR^8Z^1Q^1Z^2$—, —C(O)$NR^8Q^1Z^1$—, —C(O)$NR^8Q^1Q^2$-, —C(O)$NR^8Q^1Q^2Z^1$—, —C(O)$NR^8Z^1Q^1Q^2Z^2$—, —C(O)$NR^8(CH_2CH_2O)_nQ^1$— —C(O)$NR^8Z^1O(CH_2O)_nZ^2$—, —C(O)$NR^8Z^1Q^1Z^2NR^9Z^3$—, —C(O)$NR^8Z$ $NR^9Z^2$—, —C(O)$NR^8Q^1Z^1NR^9Z^2$—, —C(O)$NR^8Z^1Q^1Q^2OQ^3$- or —C(O)$NR^8Z^1Q^1Q^2OQ^3Z^2$—; —C(O)$OZ^1$—, —C(O)$OQ^1$-, —C(O)$OZ^1Q^1$-, —C(O)$OZ^1Q^1Z^2$—, —C(O)$OZ^1Q^1Z^2$—, —C(O)$OQ^1Q^2$-, —C(O)$OQ^1Q^2Z^1$—;

may be prepared by reacting a compound of general formula (II)

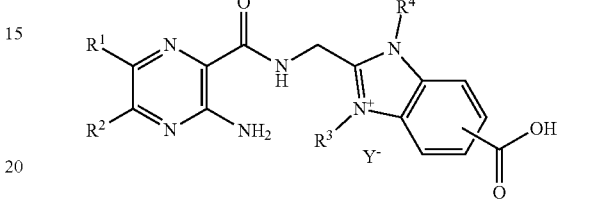

wherein $R^1$, $R^2$, $R^3$ and $R^4$ are as defined for general formula (I) and $Y^-$ is an anion which may be the same as or different from the anion $X^-$ of general formula (I); with a compound of general formula (III) or a protected compound of general formula (IIIa):

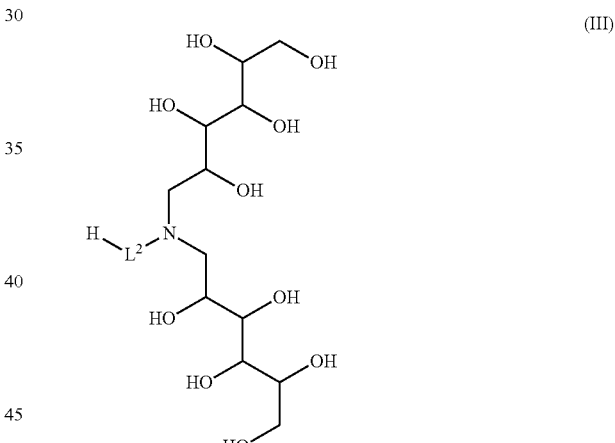

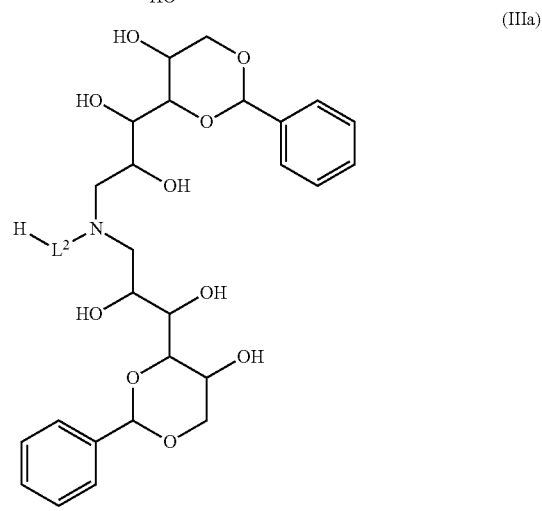

wherein:
L² is:
-Q¹-, -Q¹Z¹—, -Q¹Q²-, -Q¹Q²Z¹, -Q¹NR⁸C(O)Z¹—, -Q¹NR⁸C(O)Z¹Q², -Q¹NR⁸C(O)Z¹Q²Q³- or -Q¹NR⁸C(O)Z¹Q²Z²—;

where Q¹ is a nitrogen-containing heterocycle such that the L²-H bond is a bond between a ring nitrogen atom and the hydrogen atom; or —NR⁸Z¹—, —NR⁸Q¹-, —NR⁸Z¹Q¹-, —NR⁸Z¹Q¹Z²—, —NR⁸Q¹Z¹—, —NR⁸Q¹Q²-, —NR⁸Q¹Q²Z¹—, —NR⁸Z¹Q¹Q²Z²—, —NR⁸(CH₂CH₂O)ₙZ¹— —NR⁸Z¹O(CH₂O)ₙZ²—, —NR⁸Z¹Q¹Z²NR⁹Z³—, —NR⁸Z¹NR⁹Z²—, —NR⁸Q¹Z¹NR⁹Z²—, —NR⁸Z¹Q¹OQ²OQ³- or —NR⁸Z¹Q¹OQ²OQ³Z²—; or

—OZ¹—, —OQ¹-, —OZ¹Q¹-, —OZ¹Q¹Z²—, —OQ¹Z¹—, —OQ¹Q²-, —OQ¹Q²Z¹—;

wherein Q¹ and Q² are as defined for general formula (I); and when a compound of general formula (IIa) is used, deprotecting by treatment with an acid to remove the acetal protecting groups on the sugar moieties.

The reaction with compounds of general formula (II) which are amines may take place in the presence of a coupling agent, for example 1,1'-carbonyldiimidazole (CDI). The coupling reaction is suitably conducted at a temperature of 15-25° C., for example room temperature, in an organic solvent such as N,N-dimethylformamide (DMF).

The preparation of compounds of general formula (III) and (IIIa) will be described later.

A compound of general formula (II) may be prepared by reacting a compound of general formula (IV):

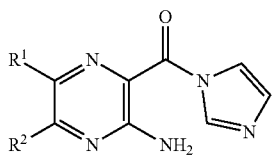

(IV)

wherein R¹ and R² are as defined for general formula (I); with a compound of general formula (V):

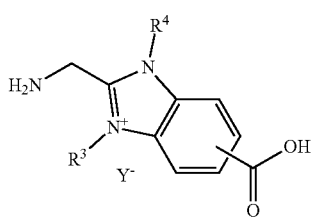

(V)

wherein R³ and R⁴ are as defined for general formula (I) and Y⁻ may be the same as or different from Y⁻ in general formula (II).

The coupling reaction may be conducted in an organic solvent such as DMF and is suitably carried out a temperature of 15-25° C., for example room temperature.

A compound of general formula (IV) may be prepared from a compound of general formula (VI):

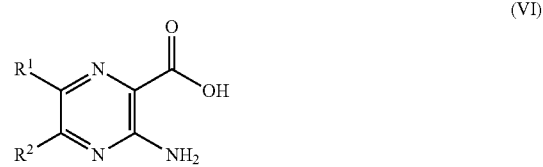

(VI)

wherein R¹ and R² are as defined for general formula (I); by reaction with carbonyl diimidazole (CDI) as described for the preparation of Intermediates 8 and 10 in the examples below.

Compounds of general formula (VI) are known to those of skill in the art and are either readily available or may be synthesised by known methods.

Compounds of general formula (V) may be synthesised from compounds of general formula (VII):

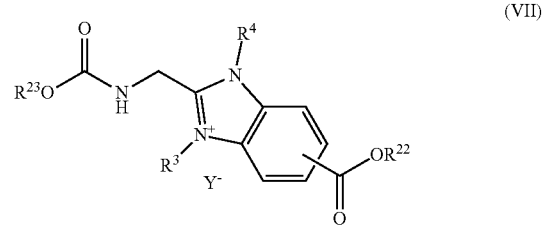

(VII)

wherein R³ and R⁴ are as defined for general formula (I), Y⁻ is an anion which may be the same as or different from Y⁻ of general formula (II) and R²² and R²³ are each independently C₁₋₁₀ alkyl optionally substituted with aryl, e.g. ⁿpropyl, ⁱpropyl, ᵗbutyl, benzyl or fluorenylmethyl.

In some cases, the removal of the protecting groups R²² and R²³ may be achieved by reaction with an acid. This is appropriate for alkyloxycarbonyl protecting groups, for example when R²² and/or R²³ is ᵗbutyl. Reaction with an acid may result in a change in the anion Y⁻. For example, as shown in the description of the preparation of Intermediate 7 in the examples below, reaction of a compound of general formula (VII) in which Y⁻ is I⁻ with HBr solution can give rise to a compound of general formula (V) in which Y⁻ is Br. Furthermore, following reaction with an acid, the compound of formula (V) will usually be present in the form of its acid addition salt.

Other protecting groups, for example Fmoc (i.e. when R²² and/or R²³ is fluorenylmethyl), can be removed by treatment with a base, for example piperidine.

In some suitable compounds of general formula (VII), R²² is ᵗbutyl and R²³ is benzyl or fluoren-9-ylmethyl.

A compound of general formula (VII) may be prepared from a compound of general formula (VIII):

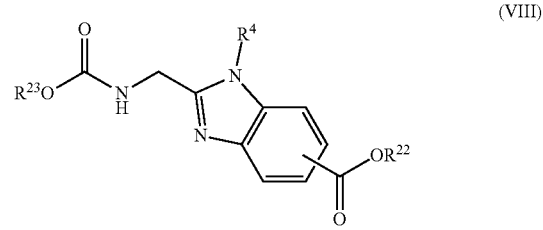

(VIII)

wherein R[4] is as defined for general formula (I) and R[22] and R[23] are as defined for general formula (VII);
by reaction with a compound of general formula (IX):

R[3]-LG[1]  (IX)

wherein R[3] is as defined for general formula (I) and LG[1] is a leaving group, typically halo, for example iodo.

The reaction may be conducted in a solvent with a high boiling point, such as acetonitrile, and the reaction mixture may be heated to a temperature of 90 to 150° C., typically about 120° C. and irradiated with microwave radiation as described for the preparation of Intermediate 6 in the examples below.

Compounds of general formula (IX) are well known and are readily available or may be prepared by methods familiar to those of skill in the art.

Compounds of general formula (VIII) may be prepared by reacting compounds of general formula (X):

(X)

wherein R[4] is as defined for general formula (I) and R[23] is as defined for general formula (VII);
by reaction with a compound of general formula (XI):

(XI)

R[22] is as defined for general formula (VII).

The reaction may be conducted in an organic solvent such as α,α,α-trifluorotoluene at a temperature of 80-120° C. as described for the preparation of Intermediate 5 in the examples below.

Compounds of general formula (XI) are well known and are readily available or may be prepared by methods familiar to those of skill in the art.

Compounds of general formula (X) in which R[23] is benzyl may be prepared from compounds of general formula (XII):

(XII)

wherein R[4] is as defined for general formula (I);

by reaction with a compound of general formula (XVII):

(XVII)

wherein R[23] is as defined for general formula (VII).

For example, when R[23] is benzyl, the compound of general formula (XVII) is benzyl 2,5-dioxopyrrolidin-1-yl carbonate as described in the examples below for the preparation of Intermediate 4.

Compounds of general formula (XII) may be prepared from compounds of general formula (XIII):

(XIII)

wherein R[4] is as defined for general formula (I) and R[24] is $C_{1-10}$ alkyl or benzyl; by reaction with an acid, suitably HCl, in a solvent such as dioxane. This reaction is suitably conducted in a solvent such as acetonitrile at a temperature of about 15 to 25° C., for example room temperature.

Suitably, R[24] is a $C_{1-10}$ alkyl group, for example [t]butyl as in Intermediate 2 in the examples below.

A compound of general formula (XIII) may be prepared by reacting a compound of general formula (XIV):

(XIV)

wherein R[4] is as defined for general formula (I), R[24] is as defined for general formula (XIII) and R[25] is $C_{1-10}$ alkyl or benzyl;
with a base, typically a hydroxide, for example, sodium, potassium or lithium hydroxide.

The reaction may be conducted in a solvent such as THF at a temperature of about 40-60° C., typically about 50° C. as described for the preparation of Intermediate 2 in the examples below.

Suitably, R[25] is a $C_{1-10}$ alkyl group, for example methyl as for Intermediate 1 in the examples below.

A compound of general formula (XIV) may be prepared by reacting a compound of general formula (XV):

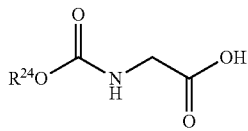

$R^{24}$ is as defined for general formula (XIII);
with a compound of general formula (XVI):

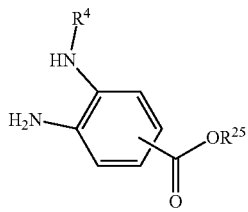

wherein $R^4$ is as defined for general formula (I), $R^{25}$ is as defined for general formula (XIVa).

The reaction is suitably carried out in the presence of a coupling agent such as 1-[bis(dimethylamino)methylene]-1H-1,2,3-triazolo[4,5-b]pyridinium 3-oxide hexafluorophosphate (HATU) and a base such as N,N-diisopropylethylamine (DIPEA).

An example of this type of reaction is shown in the examples below for the preparation of Intermediate 1.

Compounds of general formulae (XV) and (XVI) are known and are readily available or may be prepared by known methods.

A compound of general formula (III) may be prepared by reacting a protected compound of general formula (IIIa) as defined above with an acid, typically aqueous hydrochloric acid.

Suitably, the reaction is conducted at 15-25° C., usually at room temperature.

A compound of general formula (IIIa) may be prepared from a compound of general formula (XIX):

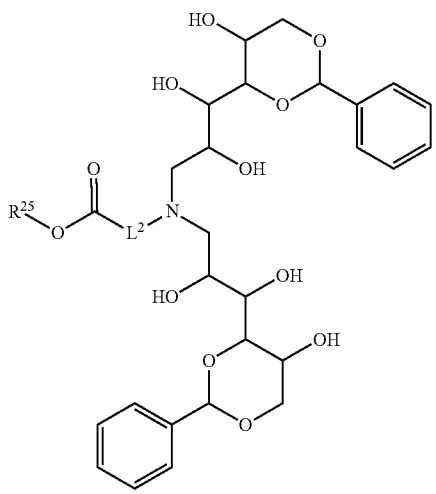

wherein $L^2$ is as defined above and $R^{25}$ is chosen such that the protecting group $R^{25}$—O—C(O)— is stable under acidic conditions;

by treatment with a base, typically a weak base such as piperidine.

Suitably, $R^{25}$ is fluorenylmethyl.

It is necessary to select the group $R^{25}$ such that $R^{25}$—O—C(O)— is stable under acidic conditions and can be removed using a base in order to avoid removal of the acetal groups protecting the sugar moieties.

Alternatively, a compound of general formula (XIX) in which $R^{25}$—O—C(O)— is not stable under acid conditions can be converted directly to a compound of general formula (III) by treatment with an acid, for example hydrochloric acid.

Examples of protecting groups suitable for removal under acid conditions include those in which $R^{25}$ is $C_{1-6}$ alkyl, for example $^t$butyl.

A compound of general formula (XIX) may be prepared from a compound of general formula (XX):

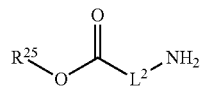

wherein $L^2$ is as defined for general formula (III) and $R^{25}$ is as defined for general formula (XIX);

by reaction with 4,6-O-benzylidene-D-glucopyranose or other 4,6-O-benzylidene protected pyranose in the presence of a reducing agent. Suitable reducing agents include hydrides, for example sodium cyanoborohydride.

Some compounds of general formula (XX) are readily available and others may be synthesised by methods familiar to those of skill in the art. The examples below describe methods for synthesising Intermediates 16, 25 and 31, all of which are compounds of general formula (XX).

A compound of general formula (I) may also be prepared by reacting a compound of general formula (IV) with a compound of general formula (XXI):

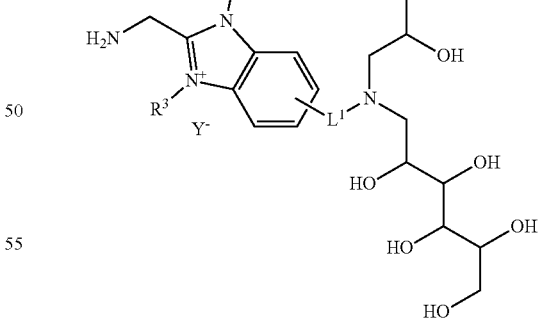

wherein $R^3$ and $R^4$ are as defined in general formula (I), $Y^-$ is an anion which may be the same as or different from $Y^-$ of general formula (II) and $L^1$ is as defined for general formula (I).

This method is particularly suitable for compounds of general formula (I) in which $L^1$ is:
—$Z^1$—, -$Q^1$-, —$Z^1Q^1$-, -$Q^1Z^1$—, —$Z^1Q^1Z^1$—, -$Q^1Q^2$-, -$Q^1Q^2Z^1$—, -$Q^1Q^2Z^1Q^3Z^2$—, —$Z^1Q^1OQ^2OQ^3$-;

—OZ$^1$—, —OQ$^1$-, —OZ$^1$Q$^1$-, —OQ$^1$Z$^1$—, —OZ$^1$Q$^1$Z$^2$—, —OQ$^1$Q$^2$-, —OQ$^1$Q$^2$Z$^1$—, —OQ$^1$Q$^2$Z$^1$Q$^3$Z$^2$—, —OZ$^1$Q$^1$OQ$^2$OQ$^3$-;

—Z$^1$NR$^8$Z$^2$—, -Q$^1$Z$^1$NR$^8$Z$^2$—, —Z$^1$NR$^8$Z$^2$Q$^1$-, -Q$^1$Z$^1$NR$^8$Z$^2$Q$^2$Z$^3$—;

—Z$^1$O(CH$_2$CH$_2$O)$_n$Z$^2$—, —Z$^1$O(CH$_2$CH$_2$O)$_n$Q$^1$-, —Z$^1$O(CH$_2$CH$_2$O)$_n$Z$^2$Q$^1$, —Z$^1$O(CH$_2$CH$_2$O)$_n$Q$^1$Z$^2$—, -Q$^1$Z$^1$O(CH$_2$CH$_2$O)$_n$Z$^2$—, -Q$^1$Z$^1$O(CH$_2$CH$_2$O)$_n$Q$^1$-, -Q$^1$Z$^1$O(CH$_2$CH$_2$O)$_n$Z$^2$Q$^1$, —Z$^1$O(CH$_2$CH$_2$O)$_n$Z$^2$Q$^1$Z$^3$—;

—Z$^1$C(O)NR$^8$Z$^2$—, —Z$^1$C(O)NR$^8$Q$^1$-, —Z$^1$C(O)NR$^8$Z$^2$Q$^1$-, —Z$^1$C(O)NR$^8$Q$^1$Z$^2$—, —Z$^1$C(O)NR$^8$Q$^1$Q$^2$-, —Z$^1$C(O)Q$^1$-, —Z$^1$C(O)Q$^1$Z$^2$—, —Z$^1$C(O)Q$^1$Q$^2$-, —Z$^1$C(O)NR$^8$Q$^1$Q$^2$Z$^2$—;

-Q$^1$C(O)Q$^2$-, Q$^1$C(O)Z$^1$—, -Q$^1$C(O)Q$^2$Z$^1$, Q$^1$C(O)Q$^2$Q$^3$-, Q$^1$C(O)Z$^1$Q$^2$-, Q$^1$C(O)Q$^2$Q$^3$Z$^1$—; —C(=NR$^{10}$)NR$^8$Z$^1$, —C(=NR$^{10}$)NR$^8$Q$^1$-, —C(=NR$^{10}$)NR$^8$Z$^1$Q$^1$-, —C(=NR$^{10}$)NR$^8$Z$^1$Q$^1$Z$^2$—, —C(=NR$^{10}$)NR$^8$Q$^1$Z$^1$, —C(=NR$^{10}$)NR$^8$Q$^1$Q$^2$-, C(=NR$^{10}$)NR$^8$Q$^1$Q$^2$Z$^1$—;

since these compounds cannot be prepared from a compound of general formula (II).

The reaction between the compounds of general formulae (IV) and (XXI) may be conducted under similar conditions to those described above for the reaction of the compound of general formula (IV) with the compound of general formula (V), A compound of general formula (XXI) may be prepared from a compound of general formula (XII):

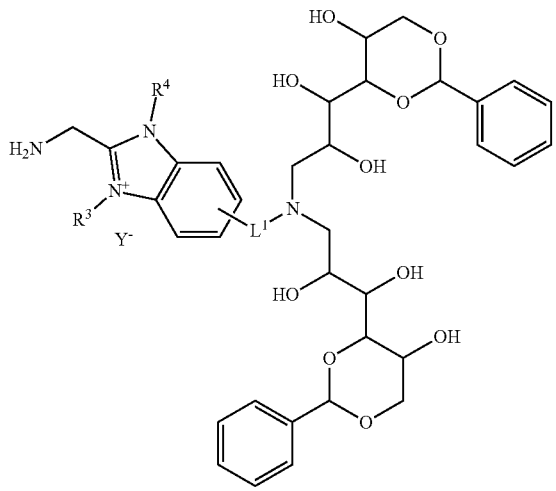

(XXII)

wherein R$^3$ and R$^4$ are as defined in general formula (I), Y$^-$ is an anion which may be the same as or different from Y$^-$ of general formula (II) and L$^1$ is as defined for general formula (XXI) by treatment with an acid, for example aqueous hydrochloric acid. The reaction is suitably carried out at 15-25° C., for example at room temperature.

A compound of general formula (XXII) may be prepared by reacting a compound of general formula (XXIIII):

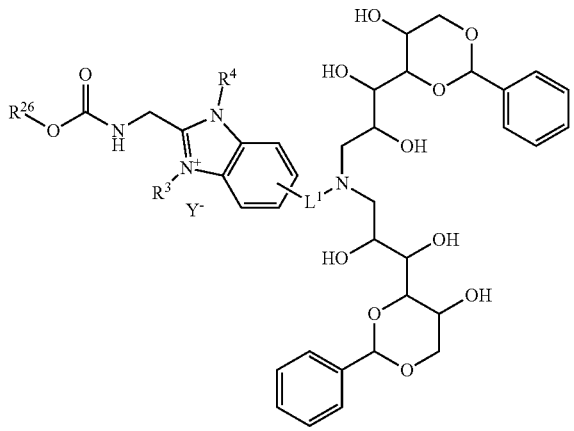

(XXIII)

wherein R$^3$ and R$^4$ are as defined in general formula (I), Y$^-$ is an anion which may be the same as or different from Y$^-$ of general formula (II), L$^1$ is as defined for general formula (XXI) and R$^{26}$ is chosen such that the protecting group R$^{26}$—O—C(O)— is stable under acidic conditions;

by treatment with a weak base such as piperidine or morpholine. Suitably, the reaction is carried out at 15-25° C., for example at room temperature and in an organic solvent such as tetrahydrofuran.

Suitably, R$^{26}$ is fluorenylmethyl.

Alternatively, a compound of general formula (XXIII) in which R$^{26}$—O—C(O)— is not stable under acid conditions can be converted directly to a compound of general formula (XI) by treatment with an acid, for example hydrochloric acid.

Examples of protecting groups suitable for removal under acid conditions include those in which R$^{26}$ is C$_{1-6}$ alkyl group, for example $^t$butyl.

Compounds of general formula (XXIII) may be prepared from compounds of general formula (XXIV):

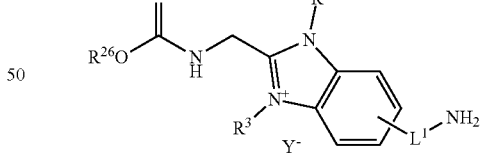

(XXIV)

wherein R$^3$ and R$^4$ are as defined in general formula (I), Y$^-$ is an anion which may be the same as or different from Y$^-$ of general formula (II), L$^1$ is as defined for general formula (XXI) and R$^{26}$ is as defined for general formula (XXIII);

by reaction with 4,6-O-benzylidene-D-glucopyranose in the presence of a weak acid, and a reducing agent such as sodium cyanoborohydride.

Compounds of general formula (XXIV) may be prepared from compounds of general formula (XXV): by reaction with an acid, for example hydrochloric acid in an organic solvent such as dioxane.

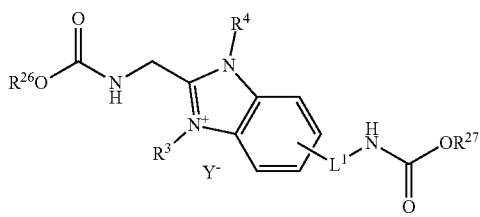
(XXV)

wherein $R^3$ and $R^4$ are as defined in general formula (I), $Y^-$ is an anion which may be the same as or different from $Y^-$ of general formula (II), $L^1$ is as defined for general formula (XXI) and $R^{26}$ is as defined for general formula (XXIII); and $R^{27}$ is chosen such that the protecting group $R^{27}$—O—C(O)— is stable under basic conditions.

Suitably, $R^{27}$ is a $C_{1-6}$ alkyl group, typically $^t$butyl.

The synthesis of several compounds of formula (XXV) is described in the examples below (see Intermediates 58, 63 and 68).

In the discussion below, references to compounds of general formula (I) include also compounds of general formulae (IA) and (IB) as set out above.

The compounds of general formula (I) are ENaC blockers and are therefore useful in the treatment or prevention of respiratory diseases and conditions.

Therefore in a further aspect of the invention there is provided a compound of general formula (I) for use in medicine.

Suitably, the compound of general formula (I) is for use in the treatment or prophylaxis of a disease or condition mediated by ENaC.

There is also provided:
A compound of general formula (I) for use in the treatment or prophylaxis of respiratory diseases and conditions.
A compound of general formula (I) for use in the treatment or prophylaxis of skin conditions or ocular conditions.

The invention further provides:
The use of a compound of general formula (I) in the preparation of an agent for the treatment or prophylaxis of respiratory diseases and conditions.
The use of a compound of general formula (I) in the preparation of an agent for the treatment or prophylaxis of skin conditions or ocular conditions There is also provided:
A method for the treatment or prophylaxis of respiratory diseases and conditions, the method comprising administering to a patient in need of such treatment an effective amount of a compound of general formula (I).
A method for the treatment or prophylaxis of skin conditions and ocular conditions, the method comprising administering to a patient in need of such treatment an effective amount of a compound of general formula (I).

Respiratory diseases and conditions which may be treated by the compounds of general formula (I) include cystic fibrosis, chronic obstructive pulmonary disease (COPD), chronic bronchitis, emphysema, bronchiectasis, including non-cystic fibrosis bronchiectasis, and asthma.

Skin conditions which may be treated by the compounds of the present invention include psoriasis, atopic dermatitis and ichthyosis.

Ocular conditions which may be treated by the compounds of the present invention included dry eye disease.

The patient to be treated is suitably a mammal and more suitably a human.

The compounds of general formula (I) may be administered in a pharmaceutical composition and therefore in a further aspect of the invention there is provided a pharmaceutical composition comprising a compound of general formula (I) and a pharmaceutically acceptable excipient. Other pharmacologically active materials may also be present, as considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including dermal, transdermal, eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12).

Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 µm e.g. around 1-5 µm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 µm or more, e.g. 100 µm or more or a $D_{50}$ of 40-150 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients. Thus in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®.

Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of general formula (I) is provided as a micronized dry powder formulation, for example comprising lactose of a suitable grade.

Thus, as an aspect of the invention there is provided a pharmaceutical composition comprising a compound of general formula (I) in particulate form in combination with particulate lactose, said composition optionally comprising magnesium stearate.

In one embodiment a compound of general formula (I) is provided as a micronized dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment a compound of general formula (I) is provided as a micronized dry powder formulation, for example comprising lactose of a suitable grade, filled into hard shell capsules for use in a single dose device such as AEROLISER.

In another embodiment a compound of general formula (I) is provided as a micronized dry powder formulation, comprising lactose of a suitable grade and magnesium stearate, filled into hard shell capsules for use in a single dose device such as AEROLISER.

In another embodiment a compound of general formula (I) is provided as a fine powder for use in an inhalation dosage form wherein the powder is in fine particles with a $D_{50}$ of 0.5-10 µm e.g. around 1-5 µm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 µm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of general formula (I) will be about 0.0001 to less than 4.0% (w/w).

Preferably, for topical ocular administration, the compositions administered according to general formula (I) will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of general formula (I). In addition, the compound of general formula (I) may also be introduced by means of ocular implants or inserts.

The compositions administered according to general formula (I) may also include various other ingredients, including, but not limited to, tonicity agents, buffers, surfactants, stabilizing polymer, preservatives, co-solvents and viscosity building agents. Suitable pharmaceutical compositions of general formula (I) include a compound of the invention formulated with a tonicity agent and a buffer. The pharmaceutical compositions of general formula (I) may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of general formula (I). The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate.

Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of compounds of general formula (I) are demulcents which function as a stabilising polymer. The stabilizing polymer should be an ionic/charged example with precedence for topical ocular use, more specifically, a polymer that carries negative charge on its surface that can exhibit a zeta-potential of (–)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the compound of general formula (I) to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of general formula (I) will be sterile, but typically unpreserved. Such compositions, therefore, generally will not contain preservatives.

The medical practitioner, or other skilled person, will be able to determine a suitable dosage for the compound of general formula (I), and hence the amount of the compound of the invention that should be included in any particular pharmaceutical formulation (whether in unit dosage form or otherwise).

Parenteral formulations will generally be sterile.

Compounds of general formula (I) may be used in combination with one or more other active agents which are useful in the treatment or prophylaxis of respiratory diseases and conditions.

An additional active agent of this type may be included in the pharmaceutical composition described above but alternatively it may be administered separately, either at the same time as the compound of general formula (I) or at an earlier or later time.

Therefore, in a further aspect of the present invention there is provided a product comprising a compound of general formula (I) and an additional agent useful in the treatment or prevention of respiratory conditions as a combined preparation for simultaneous, sequential or separate use in the treatment of a disease or condition mediated by ENaC and especially a respiratory disease or condition, for example one of the diseases and conditions mentioned above.

Suitable additional active agents which may be included in a pharmaceutical composition or a combined preparation with the compounds of general formula (I) include:
- β2 adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol;
- antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;
- dornase alpha;
- corticosteroids such as prednisone, prednisolone, flunisolide, triamcinolone acetonide, beclomethasone dipropionate, budesonide, fluticasone propionate mometasone furoate and fluticasone furoate;
- Leukotriene antagonists such as montelukast and zafirlukast;
- CFTR repair therapies e.g. CFTR potentiators such as Ivacaftor and CFTR correctors such as Lumacaftor and Tezacaftor;
- TMEM16A modulators, particularly TMEM16A potentiators; Antibiotics.

EXAMPLES

All reactions involving moisture-sensitive reagents were carried out under a nitrogen atmosphere using standard vacuum line techniques and oven-dried glassware. Commercial anhydrous solvents were used in reactions and HPLC grade solvents were employed for work-up and chromatography. Water was purified using an Elix UV-5 system. All other reagents were used as supplied without prior purification. Reported yields are corrected for LC/MS purity (determined by UV (215 nm) or ELS detection) unless otherwise stated. Sealed tube reactions were carried out in heavy wall Ace pressure tubes. Microwave experiments were carried out using a Biotage Initiator+. Flash column chromatography was carried out using a Biotage Isolera 4 using Biotage SNAP columns. NMR spectra were recorded on a Bruker Avance III HD 500 MHz or a Bruker Avance III HD 250 MHz using the solvent as internal deuterium lock. Spectra were recorded at room temperature unless otherwise stated. Analytical LC/MS were carried out on the following systems: System A: stationary phase: Kinetex Core-Shell C18 2.1×50 mm, 5 µm, 40° C.; detection UV 215 nm-ELS-MS; mobile phase: A, water+0.1% formic acid; B, MeCN+ 0.1% formic acid; gradient (A:B ratio, time): 95:5-0:100, 1.20 min; 100:0, 0.10 min; 100:0-5:95, 0.01 min; flowrate: 1.2 ml/min; System B: stationary phase: Phenomenex Gemini-NX C18 2.0×100 mm, 3 µm, 40° C.; detection UV 215 nm-ELS-MS; mobile phase: A, 2 mM ammonium bicarbonate pH 10; B, MeCN; gradient (A:B ratio, time): 95:5-0:100, 5.5 min; 0:100, 0.4 min; 0:100-95:5, 0.02 min; flowrate: 0.6 ml/min; System C: stationary phase: Phenomenex Kinetex-XB C18 2.1×100 mm, 1.7 µm, 40° C.; detection UV 215 nm-ELS-MS; mobile phase: A, water+0.1% formic acid; B, MeCN+0.1% formic acid; gradient (A:B ratio, time): 95:5-0:100, 5.30 min; 100:0, 0.50 min; 100:0-5:95, 0.02 min; 5:95, 1.18 min; flowrate: 0.6 ml/min; System D: stationary phase: Waters CSH C18 2.1×100 mm, 1.7 µm, 40° C.; detection UV 215 nm-ELS-MS; mobile phase: A, 5 mM ammonium acetate pH 7; B, MeCN; gradient (A:B ratio, time): 95:5-0:100, 5.30 min; 100:0, 0.50 min; 100:0-5:95, 0.02 min; 5:95, 1.18 min; flowrate: 0.6 ml/min.

The following abbreviations and terms have the indicated meanings throughout:

AcOH glacial acetic acid

CDI 1,1'-carbonyldiimidazole

CV column volumes dd doublet of doublets

DIPEA N,N-diisopropylethylamine

DMF N,N-dimethylformamide

DMSO dimethyl sulfoxide dppf 1,1'-bis(diphenylphosphino)ferrocene

ELS evaporative light scattering

ESI electrospray ionisation

EtOAc ethyl acetate

HATU 1-[bis(dimethylamino)methylene]-1H-1,2,3-triazolo[4,5-b]pyridinium 3-oxide hexafluorophosphate HBTU 3-[bis(dimethylamino)methyliumyl]-3H-benzotriazol-1-oxide hexafluorophosphate HPLC high-performance liquid chromatography LC/MS liquid chromatography-mass spectrometry m multiplet MeCN acetonitrile MeOH methanol NMR nuclear magnetic resonance q quartet RT room temperature Rt retention time s singlet t triplet TFA trifluoroacetic acid THF tetrahydrofuran Intermediate 1—Synthesis of methyl 2-({[(tert-butoxy)carbonyl]amino}methyl)-1-ethyl-1H-1,3-benzodiazole-6-carboxylate

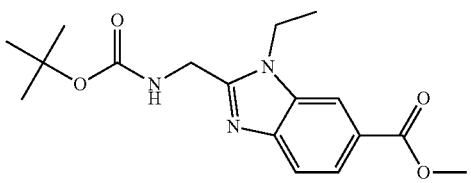 [SMILES: CCn1c(CNC(=O)OC(C)(C)C)nc2ccc(C(=O)OC)cc21]

A mixture of 2-{[(tert-butoxy)carbonyl]amino}acetic acid (8.57 g, 48.9 mmol), HATU (20.5 g, 53.8 mmol) and DIPEA (17.0 ml, 97.8 mmol) in DMF (200 ml) was stirred at RT for 1 h. Methyl 4-amino-3-(ethylamino)benzoate (9.59 g, 48.9 mmol) was added portionwise then rinsed into the reaction with THF (20 ml). The reaction mixture was stirred at RT for 18 h. A solution of 2-{[(tert-butoxy)carbonyl]amino}acetic acid (0.857 g, 4.89 mmol), HATU (1.86 g, 4.89 mmol) and DIPEA (1.70 ml, 9.78 mmol) in DMF (3 ml) was stirred at RT for 15 min then added to the main reaction. The resulting solution was stirred at RT for 3 h. A solution of 2-{[(tert-butoxy)carbonyl]amino}acetic acid (0.857 g, 4.89 mmol), HATU (1.86 g, 4.89 mmol) and DIPEA (1.70 ml, 9.78 mmol) in DMF (3 ml) was stirred at RT for 15 min then added to the main reaction. The resulting solution was stirred at RT for 64 h. The reaction mixture was added to saturated aqueous $NaHCO_3$ solution (200 ml). EtOAc (150 ml) and water (100 ml) were added then the phases were separated. The aqueous phase was extracted with EtOAc (2×150 ml), then the combined organic phases were washed with water (4×100 ml) and brine (50 ml) then dried over $Na_2SO_4$, filtered and evaporated to afford the crude intermediate as a black oil (18 g). The oil thus obtained was dissolved in acetic acid (80 ml) and stirred at 70° C. for 1 h. The reaction was allowed to cool to RT then evaporated to afford a brown solid. The solid was suspended in EtOAc (200 ml) then filtered and was washed with EtOAc, then dried under vacuum to afford a pale pink solid (6.5 g). The solid thus obtained was suspended in EtOAc (200 ml). The resulting suspension was heated at 50° C. for 15 min then allowed to cool to RT. The solid was collected by filtration to afford the product as a white solid (2.43 g). The filtrate was again filtered and the solid was collected by filtration, washed with EtOAc:heptane then dried under vacuum to afford a second batch of the product as a white solid (1.34 g). The filtrate was transferred to a separating funnel then washed with saturated aqueous $NaHCO_3$ solution (3×100 ml), water (100 ml) and brine (50 ml) then dried over $Na_2SO_4$, filtered and evaporated to a yellow solid which was suspended in the minimum volume of EtOAc:heptane (1:4) and filtered then dried under vacuum to afford a third batch of the product as a white solid (1.77 g). The filtrate from the first filtration was transferred to a separating funnel then washed with saturated aqueous $NaHCO_3$ solution (3×100 ml), water (100 ml) and brine (50 ml) then dried over $Na_2SO_4$, filtered and evaporated to a dark brown solid. The solid was suspended in EtOAc (50 ml) then filtered. The solid was dried under vacuum to afford a fourth batch of the product as a white solid (3.4 g). The filtrate was evaporated to afford a dark solid (8 g). The solid thus obtained was dissolved in $CH_2Cl_2$ then evaporated onto silica (16 g). The crude material was purified by flash column chromatography on a silica column (100 g). The column was eluted with EtOAc:heptane, increasing the gradient linearly from 0:100 to 100:0 over 10 column volumes. The desired fractions were combined and evaporated to afford a brown solid. The solid thus obtained was suspended in EtOAc:heptane (1:4, 20 ml) then filtered. The solid was washed with EtOAc:heptane then dried under vacuum to afford a fifth batch of the product as a white solid (1.45 g). The filtrate was concentrated in vacuo then the residue was suspended in EtOAc, filtered and dried under vacuum to afford a sixth batch of the product as an off-white solid (0.32 g). The 6 batches of solid were combined as an EtOAc suspension then evaporated and dried under vacuum to yield the product as an off-white solid (10.7 g, 66%).

$^1$H NMR (500 MHz, DMSO-$d_6$) δ 8.16 (d, J=1.1 Hz, 1H), 7.82 (dd, J=8.4, 1.6 Hz, 1H), 7.66 (d, J=8.4 Hz, 1H), 7.52 (t, J=4.9 Hz, 1H), 4.47 (d, J=5.8 Hz, 2H), 4.35 (q, J=7.2 Hz, 2H), 3.88 (s, 3H), 1.46-1.22 (m, 12H).

LC/MS (System A): m/z (ESI$^+$)=334 [MH$^+$], $R_t$=0.98 min, UV purity=100%.

Intermediate 2—2-({[(tert-butoxy)carbonyl]amino}methyl)-1-ethyl-1H-1,3-benzodiazole-6-carboxylic acid

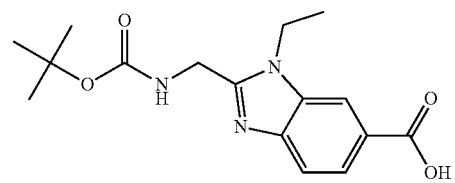 [SMILES: CCn1c(CNC(=O)OC(C)(C)C)nc2ccc(C(=O)O)cc21]

Aqueous LiOH solution (2.0 M, 16 ml, 32 mmol) was added to a suspension of methyl 2-({[(tert-butoxy)carbonyl]amino}methyl)-1-ethyl-1H-1,3-benzodiazole-6-carboxylate, Intermediate 1 (6.91 g, 20.7 mmol) in THF (100 ml). The reaction mixture was stirred at 50° C. for 16 h then allowed to cool to RT. The reaction mixture was concentrated in vacuo then the resulting solid was suspended in water (50 ml). Aqueous HCl solution (2 M) was added dropwise until pH 4 was reached. The resultant suspension was filtered then the solid was washed with the minimum volume of water and MeCN then dried under vacuum to afford the product as a white solid (6.05 g, 90%).

$^1$H NMR (500 MHz, DMSO-$d_6$) δ 12.77 (s, 1H), 8.18-8.07 (m, 1H), 7.80 (dd, J=8.4, 1.5 Hz, 1H), 7.63 (d, J=8.4 Hz, 1H), 7.52 (t, J=5.4 Hz, 1H), 4.47 (d, J=5.8 Hz, 2H), 4.34 (q, J=7.2 Hz, 2H), 1.46-1.21 (m, 12H).

LC/MS (System A): m/z (ESI$^+$)=320 [MH$^+$], $R_t$=0.84 min, UV purity=99%.

Intermediate 3—Synthesis of 2-(aminomethyl)-1-ethyl-1H-1,3-benzodiazole-6-carboxylic acid dihydrochloride

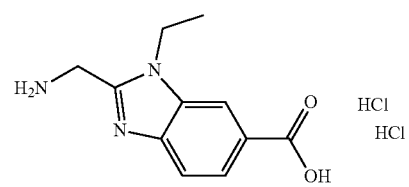 [SMILES: CCn1c(CN)nc2ccc(C(=O)O)cc21 ; Cl ; Cl]

HCl solution in dioxane (4.0 M, 14 ml, 56 mmol) was added to a suspension of 2-({[(tert-butoxy)carbonyl] amino}methyl)-1-ethyl-1H-1,3-benzodiazole-6-carboxylic acid, Intermediate 2 (3.55 g, 11.1 mmol) in MeCN (60 ml). The reaction mixture was stirred at RT for 4 h then filtered. The solid was dried under vacuum to afford the product as a white solid (3.39 g, 98%).

$^1$H NMR (500 MHz, DMSO-$d_6$) δ 8.78 (s, 3H), 8.25 (s, 1H), 7.88 (dd, J=8.5, 1.2 Hz, 1H), 7.74 (d, J=8.4 Hz, 1H), 4.54-4.47 (m, 2H), 4.38 (q, J=7.2 Hz, 2H), 1.34 (t, J=7.2 Hz, 3H).

LC/MS (System A): m/z (ESI$^+$)=220 [MH$^+$], $R_t$=0.16 min, ELS purity=94%.

Intermediate 4—Synthesis of 2-({[(benzyloxy)carbonyl]amino}methyl)-1-ethyl-1H-1,3-benzodiazole-6-carboxylic acid

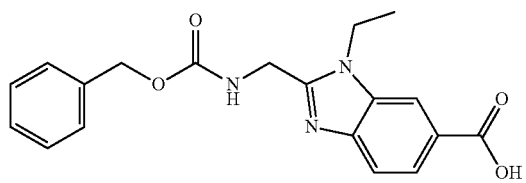 [SMILES: CCn1c(CNC(=O)OCc2ccccc2)nc2ccc(C(=O)O)cc21]

NaHCO$_3$ (4.83 g, 57.5 mmol) was added portionwise to a cooled (0° C.) suspension of 2-(aminomethyl)-1-ethyl-1H-1,3-benzodiazole-6-carboxylic acid dihydrochloride, Intermediate 3 (4.20 g, 14.4 mmol) in water (40 ml). The reaction mixture was allowed to warm to RT then a solution of benzyl 2,5-dioxopyrrolidin-1-yl carbonate (3.94 g, 15.8 mmol) in THF (40 ml) was added dropwise over 15 min. The reaction mixture was left to stir at RT for 16 h. The resultant mixture was extracted with EtOAc (50 ml). The phases were separated then the organic phase was washed with water (3×10 ml). The combined aqueous phases were acidified to pH 5 by addition of aqueous HCl solution (2 M), resulting in precipitation of a solid. The resultant suspension was filtered then the solid was dried under vacuum to afford the product as a white solid (3.5 g, 69%).

$^1$H NMR (500 MHz, DMSO-$d_6$) δ 8.12 (s, 1H), 7.97 (t, J=5.8 Hz, 1H), 7.80 (dd, J=8.4, 1.4 Hz, 1H), 7.62 (d, J=8.4 Hz, 1H), 7.42-7.09 (m, 5H), 5.06 (s, 2H), 4.54 (d, J=5.9 Hz, 2H), 4.33 (q, J=7.0 Hz, 2H), 1.28 (t, J=7.1 Hz, 3H).

LC/MS (System A): m/z (ESI$^+$)=354 [MH$^+$], $R_t$=0.89 min, UV purity=100%.

Intermediate 5—tert-butyl 2-({[(benzyloxy)carbonyl]amino}methyl)-1-ethyl-1H-1,3-benzodiazole-6-carboxylate

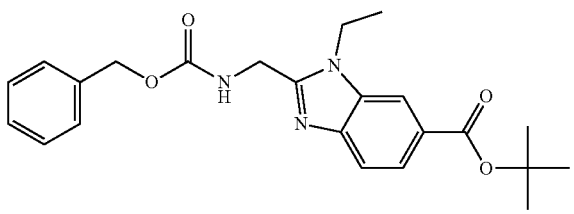 [SMILES: CCn1c(CNC(=O)OCc2ccccc2)nc2ccc(C(=O)OC(C)(C)C)cc21]

1,1-Di-tert-butoxy-N,N-dimethylmethanamine (6.77 ml, 28.3 mmol) was added to a suspension of 2-({[(benzyloxy) carbonyl]amino}methyl)-1-ethyl-1H-1,3-benzodiazole-6-carboxylic acid, Intermediate 4 (2.50 g, 7.08 mmol) in α,α,α-trifluorotoluene (50 ml). The reaction mixture was heated at 100° C. for 1 h. The reaction mixture was allowed to cool to RT then 1,1-di-tert-butoxy-N,N-dimethylmethanamine (6.77 ml, 28.3 mmol) was added dropwise over 15 min. The resultant mixture was heated at 100° C. for 45 min. The reaction mixture was cooled to 50° C. then 1,1-di-tert-butoxy-N,N-dimethylmethanamine (3.38 ml, 14.2 mmol) was added dropwise over 5 min. The resultant mixture was heated at 100° C. for 0.5 h then allowed to cool to RT. The reaction mixture was partitioned between EtOAc (50 ml) and water (50 ml). The phases were separated then the organic phase was washed with water (2×30 ml), saturated aqueous NaHCO$_3$ solution (20 ml) and brine (10 ml) then dried over Na$_2$SO$_4$, filtered and concentrated in vacuo to afford a beige solid (2.5 g). The solid thus obtained was suspended in MeCN (10 ml). The solid was collected by filtration then dried under vacuum to afford the product as an off-white solid (2.30 g, 79%).

$^1$H NMR (500 MHz, DMSO-$d_6$) δ 8.07 (s, 1H), 7.97 (m, 1H), 7.76 (dd, J=8.4, 1.5 Hz, 1H), 7.64 (d, J=8.4 Hz, 1H), 7.34 (m, 5H), 5.07 (s, 2H), 4.55 (d, J=6.0 Hz, 2H), 4.38-4.25 (m, 2H), 1.57 (s, 9H), 1.29 (m, 3H).

LC/MS (System A): m/z (ESI$^+$)=410 [MH$^+$], $R_t$=1.17 min, UV purity=99%.

Intermediate 6—Synthesis of 2-({[(benzyloxy)carbonyl]amino}methyl)-6-[(tert-butoxy)carbonyl]-1,3-diethyl-1H-1,3-benzodiazol-3-ium iodide

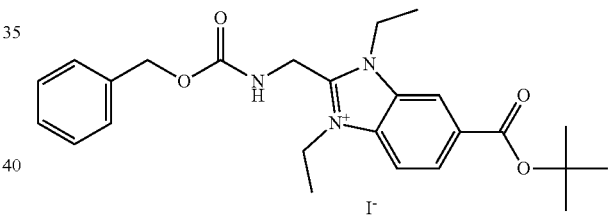

Three reactions were run independently as follows then combined for work-up. Reaction 1: a suspension of tert-butyl 2-({[(benzyloxy)carbonyl]amino}methyl)-1-ethyl-1H-1,3-benzodiazole-6-carboxylate, Intermediate 5 (800 mg, 1.95 mmol) and iodoethane (629 µl, 7.82 mmol) in MeCN (10 ml) was heated under microwave irradiation for 2 h at 120° C. The reaction was retreated with iodoethane (629 µl, 7.82 mmol) then the reaction mixture was heated under microwave irradiation for a further 2 h at 120° C. Reaction 2: a suspension of tert-butyl 2-({[(benzyloxy) carbonyl]amino}methyl)-1-ethyl-1H-1,3-benzodiazole-6-carboxylate, Intermediate 81 (800 mg, 1.95 mmol) and iodoethane (629 µl, 7.82 mmol) in MeCN (10 ml) was heated under microwave irradiation for 1 h 45 min at 120° C. The reaction was retreated with iodoethane (629 µl, 7.82 mmol) then the reaction mixture was heated under microwave irradiation for a further 1.5 h at 120° C. Reaction 3: a suspension of tert-butyl 2-({[(benzyloxy)carbonyl] amino}methyl)-1-ethyl-1H-1,3-benzodiazole-6-carboxylate, Intermediate 81 (700 mg, 1.71 mmol) and iodoethane (591 µl, 6.84 mmol) in MeCN (10 ml) was heated under microwave irradiation for 1.5 h at 120° C. The reaction was retreated with iodoethane (629 µl, 7.82 mmol) then the reaction mixture was heated under microwave irradiation for a further 1.5 h at 120° C. The three reactions were combined and concentrated in vacuo. The crude material was purified by flash column chromatography on C18 (60 g). The column was eluted with MeCN:water+0.1% formic acid using the following gradient (% MeCN, column volumes): 5%, 2 CV; 5-31%, 5 CV; 31%, 4 CV; 31-59%, 6 CV; 59-100%, 3 CV; 100% 1 CV. The desired fractions were combined and concentrated in vacuo to afford the product as a white foam (2.13 g, 67%).

$^1$H NMR (500 MHz, DMSO-d$_6$) δ 8.54 (s, 1H), 8.43 (t, J=5.1 Hz, 1H), 8.22-8.12 (m, 2H), 7.42-7.27 (m, 5H), 5.06 (s, 2H), 4.90 (d, J=5.3 Hz, 2H), 4.79-4.59 (m, 4H), 1.61 (s, 9H), 1.47-1.36 (m, 6H).

LC/MS (System A): m/z (ESI$^+$)=438 [M$^+$], R$_t$=1.07 min, UV purity=100%.

Intermediate 7—Synthesis of 2-(aminomethyl)-6-carboxy-1,3-diethyl-1H-1,3-benzodiazol-3-ium hydrobromide bromide

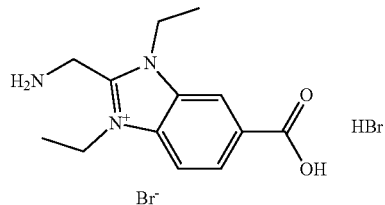 [SMILES: CCn1c(CN)[n+](CC)c2ccc(C(=O)O)cc21 ; Br ; [Br-]]

HBr solution in AcOH (33 wt %, 4.28 ml, 18.8 mmol) was added to a solution of 2-({[(benzyloxy)carbonyl]amino}methyl)-6-[(tert-butoxy)carbonyl]-1,3-diethyl-1H-1,3-benzodiazol-3-ium iodide, Intermediate 6 (2.13 g, 3.77 mmol) in AcOH (10 ml). The reaction mixture was stirred at RT for 0.5 h. The resultant suspension was concentrated in vacuo then azeotroped with MeCN. The solid thus obtained was suspended in the minimum volume of MeCN then filtered and dried under vacuum to afford the product as a white solid (1.52 g, 99%).

$^1$H NMR (500 MHz, DMSO-d$_6$) δ 8.69 (s, 1H), 8.31-8.20 (m, 2H), 4.85-4.63 (m, 6H), 1.53-1.40 (m, 6H).

LC/MS (System A): m/z (ESI$^+$)=248 [M$^+$], R$_t$=0.15 min, ELS purity=100%.

Intermediate 8—Synthesis of 3-chloro-5-(1H-imidazole-1-carbonyl)pyrazine-2,6-diamine

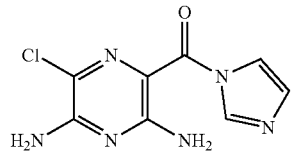 [SMILES: Nc1nc(N)c(C(=O)n2ccnc2)nc1Cl]

CDI (705 mg, 4.35 mmol) was added to a suspension of 3,5-diamino-6-chloro-pyrazine-2-carboxylic acid (546 mg, 2.90 mmol) in DMF (6 ml). The resulting suspension was stirred at RT for 10 min. More DMF (4 ml) was added then the reaction was left to stir at RT for a further 17 h. The reaction mixture was cooled (0° C.) then water (20 ml) was added in portions (2 ml) over 0.5 h. The mixture was stirred at 0° C. for 1 h. The resulting suspension was filtered then the solid was rinsed with ice cold water (10 ml) and then dried in vacuo to afford an off-white solid (674 mg, 95%).

$^1$H NMR (500 MHz, DMSO-d6) δ 8.54-8.52 (m, 1H), 8.27-7.26 (m, 5H), 7.08-6.99 (m, 1H). 3 wt % residual DMF.

LC/MS (System A): m/z (ESI$^+$)=239 [M($^{35}$Cl)H$^+$], 241 [M($^{37}$Cl)H$^+$], R$_t$=0.15 and 0.52 min, ELS purity=82+18%.

Intermediate 9—Synthesis of 6-carboxy-2-{[(3,5-diamino-6-chloropyrazin-2-yl)formamido]methyl}-1,3-diethyl-1H-1,3-benzodiazol-3-ium bromide

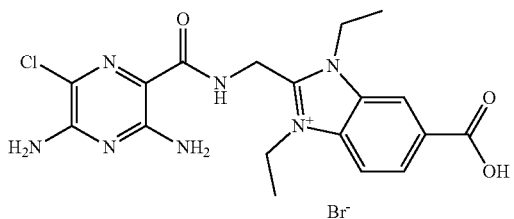 [SMILES: CCn1c(CNC(=O)c2nc(Cl)c(N)nc2N)[n+](CC)c2ccc(C(=O)O)cc21 ; [Br-]]

A suspension of 3-chloro-5-(1H-imidazole-1-carbonyl)pyrazine-2,6-diamine, Intermediate 8 (352 mg, 1.47 mmol) and 2-(aminomethyl)-6-carboxy-1,3-diethyl-1H-1,3-benzodiazol-3-ium hydrobromide bromide, Intermediate 7 (603 mg, 1.47 mmol) in DMF (15 ml) was stirred at RT. After a 3 min, DMSO (0.1 ml) was added then the reaction mixture was left to stir at RT for 23 h. The reaction mixture was concentrated in vacuo then azeotroped with MeCN (20 ml). The residue thus obtained was suspended in MeCN (20 ml) with sonication. The resulting suspension was cooled (0° C.). The solid was collected by filtration, rinsed with ice-chilled MeCN (10 ml), then dried in vacuo to afford the product as an orange solid (701 mg, 91%).

$^1$H NMR (500 MHz, DMSO-d$_6$) δ 13.55 (s, 1H), 8.99 (t, J=5.3 Hz, 1H), 8.64-8.57 (m, 1H), 8.22 (dd, J=8.7, 1.3 Hz, 1H), 8.17 (d, J=8.7 Hz, 1H), 7.78-6.44 (m, 4H), 5.01 (d, J=5.3 Hz, 2H), 4.76 (q, J=7.1 Hz, 2H), 4.69 (q, J=7.1 Hz, 2H), 1.48-1.34 (m, 6H). 5 wt % residual DMF.

LC/MS (System A): m/z (ESI$^-$)=418 [M($^{35}$Cl)$^+$], 420 [M($^{37}$Cl)$^+$], R$_t$=0.79 min, UV purity=99%.

Intermediate 10—Synthesis of 5-bromo-3-(1H-imidazole-1-carbonyl)pyrazin-2-amine

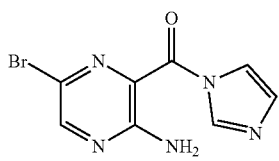

CDI (2.23 g, 13.8 mmol) was added to a suspension of 3-amino-6-bromopyrazine-2-carboxylic acid (2.00 g, 9.17 mmol) in DMF (20 ml). The reaction was stirred at RT for 16 h. The reaction mixture was cooled (0° C.) then diluted with water (20 ml). The solid was collected by filtration then washed with the minimum volume of water and cooled (0° C.) MeCN then dried under vacuum to afford the product as a yellow solid (2.23 g, 86%).

$^1$H NMR (250 MHz, DMSO-d$_6$) δ 8.58-8.52 (m, 2H), 7.96-7.82 (m, 3H), 7.15-7.07 (m, 1H).

LC/MS (System A, MeOH quench): m/z (ESI⁺)=232 [Methyl ester M(⁷⁹Br)H⁺], 234 [Methyl ester M(⁸¹Br)H⁺]), $R_t$=0.87 min, UV purity=95%.

Intermediate 11—Synthesis of 2-{[(3-amino-6-bromopyrazin-2-yl)formamido]methyl}-6-carboxy-1,3-diethyl-1H-1,3-benzodiazol-3-ium bromide

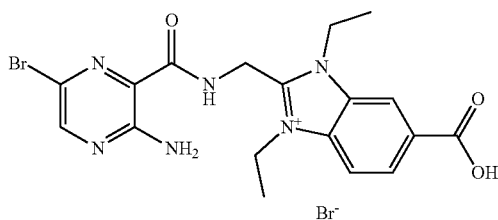 [SMILES: CCn1c(CNC(=O)c2nc(Br)cnc2N)[n+](CC)c2ccc(C(=O)O)cc21 ; [Br-]]

A solution of 5-bromo-3-(1H-imidazole-1-carbonyl)pyrazin-2-amine, Intermediate 10 (40 mg, 0.15 mmol) and 2-(aminomethyl)-6-carboxy-1,3-diethyl-1H-1,3-benzodiazol-3-ium hydrobromide bromide, Intermediate 7 (61 mg, 0.15 mmol) in DMF (1 ml) was stirred at RT for 17 h. The reaction was filtered then the solid collected was washed with MeCN and dried under vacuum to afford the product as an off-white solid (31 mg, 37%).

¹H NMR (500 MHz, DMSO-d₆) δ 13.58 (s, 1H), 9.60 (t, J=5.3 Hz, 1H), 8.62 (s, 1H), 8.42 (s, 1H), 8.26-8.16 (m, 2H), 7.67 (s, 2H), 5.10 (d, J=5.3 Hz, 2H), 4.80-4.65 (m, 4H), 1.44-1.39 (m, 6H).

LC/MS (System C): m/z (ESI⁺)=447 [M(⁷⁹Br)⁺], 449 [M(⁸¹Br)⁺], $R_t$=1.29 min, UV purity=94%.

Intermediate 12—Synthesis of (9H-fluoren-9-yl)methyl 4-{bis[(2S,3R)-2,3-dihydroxy-3-[(4R,5R)-5-hydroxy-2-phenyl-1,3-dioxan-4-yl]propyl]amino}piperidine-1-carboxylate; formic acid

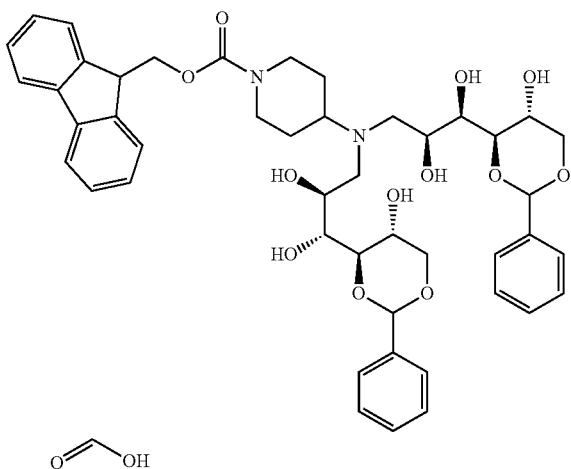

A mixture of 9H-fluoren-9-ylmethyl 4-aminopiperidine-1-carboxylate hydrochloride (7.80 g, 21.7 mmol) and 4,6-O-benzylidene-D-glucopyranose (23.3 g, 86.9 mmol) in MeOH (110 ml) was stirred at RT for 0.5 h. NaCNBH₃ (5.46 g, 86.9 mmol) was added then the reaction was heated to 60° C. The reaction was stirred at 60° C. for 18 h. The reaction was recharged with 4,6-O-benzylidene-D-glucopyranose (23.3 g, 86.9 mmol) then left to stir at 60° C. for a further 6 h. The reaction was allowed to cool to RT then added to saturated aqueous NaHCO₃ solution (200 ml) and EtOAc (200 ml). The resultant mixture was filtered through a Celite pad then the filtrate was transferred to a separating funnel. The phases were separated then the organic phase was washed with brine:water (1:1, 2×200 ml), brine (100 ml), dried over Na₂SO₄, filtered and concentrated in vacuo. The residue was suspended in MeCN (200 ml) and tBME (250 ml) the filtered. The solid obtained was suspended in MeOH then filtered. The combined filtrates were concentrated in vacuo. The crude material thus obtained was purified by flash column chromatography on C18 (400 g). The column was eluted with MeCN:water+0.1% formic acid using the following gradient (% MeCN, column volumes): 20%, 1 CV; 20-50%, 10 CV; 50-100%, 2 CV; 100%, 2 CV. The desired fractions were combined and concentrated in vacuo to remove most of the MeCN and some of the water then the residual aqueous solution was lyophilised to afford the product as an off-white solid (12.6 g, 66%).

¹H NMR (500 MHz, DMSO-d6) δ 8.16 (s, 1H), 7.90 (d, J=7.4 Hz, 2H), 7.64-7.54 (m, 2H), 7.45-7.27 (m, 14H), 5.46 (s, 2H), 5.23-5.07 (m, 2H), 4.88-4.21 (m, 6H), 4.13 (dd, J=10.5, 5.3 Hz, 2H), 4.02-3.67 (m, 9H), 3.61 (d, J=9.2 Hz, 2H), 3.50 (t, J=10.5 Hz, 2H), 2.64-2.56 (m, 3H), 2.42-2.31 (m, 2H), 1.69-1.51 (m, 2H), 1.31-0.90 (m, 2H).

LC/MS (System A): m/z (ESI⁺)=827 [MH⁺], $R_t$=1.08 min, UV purity=100%.

Intermediate 13—Synthesis of (1R,2S)-3-{[(2S,3R)-2,3-dihydroxy-3-[(4R,5R)-5-hydroxy-2-phenyl-1,3-dioxan-4-yl]propyl](piperidin-4-yl)amino}-1-[(4R,5R)-5-hydroxy-2-phenyl-1,3-dioxan-4-yl]propane-1,2-diol

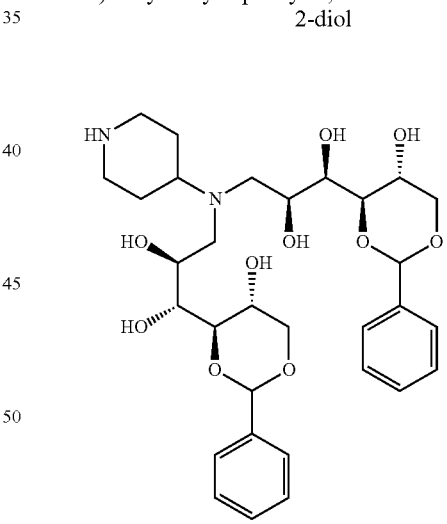

Piperidine (9.01 ml, 91.2 mmol) was added to a solution of (9H-fluoren-9-yl)methyl 4-{bis[(2S,3R)-2,3-didroxy-dihydroxy-3-[(4R,5R)-5-hydroxy-2-phenyl-1,3-dioxan-4-yl]propyl]amino}piperidine-1-carboxylate; formic acid, Intermediate 12 (12.6 g, 14.4 mmol) in THF (150 ml). The reaction was left to stir at RT for 16 h then concentrated in vacuo. The crude solid material was suspended in MeOH (100 ml) then heated to dissolve. The solution was allowed to cool then concentrated in vacuo until solid was observed. The resultant suspension was stirred at RT for 15 min then filtered. The filtrate was concentrated in vacuo until solid was observed. The resultant suspension was stirred at RT for 15 min then filtered. The filtrate was purified by flash column chromatography on C18 (400 g). The column was eluted with MeCN:H$_2$O+0.1% formic acid using the following gradient (% MeCN, column volumes): 10%, 1 CVs; 10-25%, 6 CVs; 25%, 2 CVs; 25-50%, 1 CV; 50-100%, 1 CVs; 100%, 2 CVs. The desired fractions were combined and concentrated in vacuo to remove the majority of the solvent. The residual solution thus obtained was lyophilised to afford a pale-yellow solid (6.35 g). The solid thus obtained was partitioned between EtOAc (100 ml) and saturated aqueous NaHCO$_3$ solution (100 ml). The phases were separated then the aqueous phase was extracted with CHCl$_3$:IPA (2:1, 100 ml) and n-BuOH (2×100 ml). The combined organic phases were dried over Na$_2$SO$_4$ then concentrated in vacuo. The residue was dissolved in 1:2 MeCN:water then lyophilised to afford the product as a white solid (5.81 g, 67%).

$^1$H NMR (500 MHz, CD$_3$OD) δ 7.48 (dd, J=7.5, 2.0 Hz, 4H), 7.38-7.28 (m, 6H), 5.50 (s, 2H), 4.23 (dd, J=10.6, 5.4 Hz, 2H), 4.00-3.88 (m, 4H), 3.85 (dd, J=5.5, 2.4 Hz, 2H), 3.70 (dd, J=9.3, 2.4 Hz, 2H), 3.60 (t, J=10.5 Hz, 2H), 3.09-3.02 (m, 1H), 3.00-2.91 (m, 1H), 2.78 (dd, J=13.4, 3.7 Hz, 2H), 2.75-2.65 (m, 1H), 2.59 (dd, J=13.4, 8.8 Hz, 2H), 2.54-2.47 (m, 1H), 2.37-2.28 (m, 1H), 1.81-1.70 (m, 2H), 1.55-1.49 (m, 1H), 1.42-1.35 (m, 1H).

LC/MS (System A): m/z (ESI$^+$)=605 [MH$^+$], R$_t$=0.77 min, UV purity=100%.

Intermediate 14—Synthesis of (2R,3R,4R,5S)-6-{[(2S,3R,4R,5R)-2,3,4,5,6-pentahydroxyhexyl](piperidin-4-yl)amino}hexane-1,2,3,4,5-pentol dihydrochloride

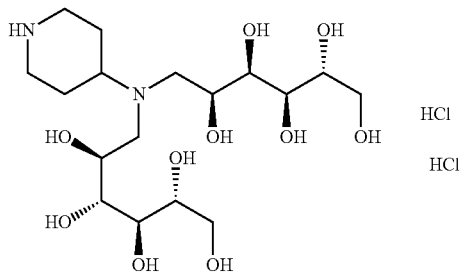 [SMILES: OC[C@@H](O)[C@@H](O)[C@H](O)[C@@H](O)CN(C[C@H](O)[C@@H](O)[C@H](O)[C@H](O)CO)C1CCNCC1 ; Cl ; Cl]

A mixture of (1R,2S)-3-{[(2S,3R)-2,3-dihydroxy-3-[(4R,5R)-5-hydroxy-2-phenyl-1,3-dioxan-4-yl]propyl](piperidin-4-yl)amino}-1-[(4R,5R)-5-hydroxy-2-phenyl-1,3-dioxan-4-yl]propane-1,2-diol, Intermediate 13 (5.81 g, 8.93 mmol) and aqueous HCl solution (2 M, 90 ml, 180 mmol) was stirred at RT for 18 h. The reaction mixture was concentrated in vacuo then re-dissolved in water and lyophilised to afford the product as a white solid (4.14 g, 92%).

$^1$H NMR (500 MHz, D$_2$O) δ 4.34-4.21 (m, 2H), 4.10-3.97 (m, 1H), 3.95-3.76 (m, 6H), 3.75-3.34 (m, 10H), 3.25-3.12 (m, 2H), 2.51-2.35 (m, 2H), 2.27-1.94 (m, 2H). LC/MS (System A): m/z (ESI$^+$)=429 [MH$^+$], R$_t$=0.12 min, ELS purity=100%.

Intermediate 15—Synthesis of (9H-fluoren-9-yl)methyl 4-({[(tert-butoxy)carbonyl]amino}methyl)piperidine-1-carboxylate

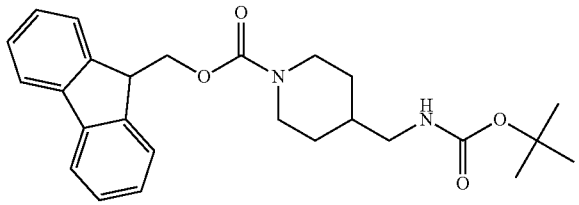 [SMILES: CC(C)(C)OC(=O)NCC1CCN(C(=O)OCC2c3ccccc3-c3ccccc32)CC1]

NaHCO$_3$ (2.35 g, 28.0 mmol) was added portionwise over 1 min to a stirred solution of tert-butyl N-(4-piperidylmethyl)carbamate (3.00 g, 14.0 mmol) in MeCN (50 ml) and water (50 ml). A solution of (2,5-dioxopyrrolidin-1-yl) 9H-fluoren-9-ylmethyl carbonate (4.72 g, 14.0 mmol) in MeCN (50 ml) was added dropwise over 1 h then the reaction was left to stir at RT for 18 h. The reaction mixture was partitioned between EtOAc (100 ml) and water (100 ml). Brine was added to aid separation of phases. The phases were separated then the aqueous phase was extracted with EtOAc (50 ml). The combined organic extracts were washed with brine (70 ml), dried over MgSO$_4$, filtered and concentrated in vacuo to afford the product as an off white solid (7.02 g, 96%).

$^1$H NMR (500 MHz, DMSO-d$_6$) δ 7.89 (d, J=7.5 Hz, 2H), 7.62 (d, J=7.4 Hz, 2H), 7.41 (t, J=7.3 Hz, 2H), 7.33 (td, J=7.4, 0.9 Hz, 2H), 6.85 (t, J=5.8 Hz, 1H), 4.53-4.29 (m, 2H), 4.26 (t, J=6.3 Hz, 1H), 3.97-3.67 (m, 2H), 2.78 (t, J=6.1 Hz, 2H), 2.75-2.61 (m, 2H), 1.60-1.44 (m, 3H), 1.38 (s, 9H), 0.93-0.73 (m, 2H). 5 wt % residual solvent.

LC/MS (System A): m/z (ESI$^+$)=459 [M+Na$^+$], R$_t$=1.40 min, UV purity=89%.

Combined estimate purity=84%.

Intermediate 16—Synthesis of (9H-fluoren-9-yl)methyl 4-(aminomethyl)piperidine-1-carboxylate hydrochloride

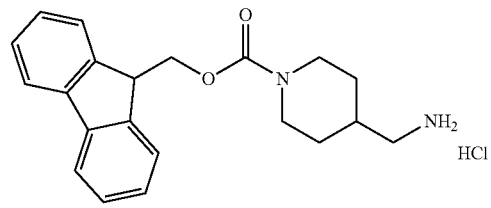 [SMILES: NCC1CCN(C(=O)OCC2c3ccccc3-c3ccccc32)CC1 ; Cl]

HCl solution in dioxane (4.0 M, 12 ml, 48 mmol) was added drop-wise over 8 min to a stirred solution of (9H-fluoren-9-yl)methyl 4-({[(tert-butoxy)carbonyl]amino}methyl)piperidine-1-carboxylate, Intermediate 15 (7.00 g, 16.0 mmol) in MeCN (100 ml). The resulting solution was stirred at RT for 17 h then concentrated in vacuo to afford the product as a white solid (5.56 g, 82%).

$^1$H NMR (500 MHz, DMSO-d$_6$) δ 8.04-7.82 (m, 5H), 7.62 (d, J=7.4 Hz, 2H), 7.42 (t, J=7.4 Hz, 2H), 7.34 (td, J=7.4, 0.9 Hz, 2H), 4.42-4.32 (m, 2H), 4.27 (t, J=6.3 Hz, 1H), 4.04-3.71 (m, 2H), 2.84-2.69 (m, 2H), 2.67 (d, J=6.8

Hz, 2H), 1.80-1.70 (m, 1H), 1.70-1.58 (m, 2H), 1.04-0.87 (m, 2H). 7 wt % residual dioxane.

LC/MS (System A): m/z (ESI$^+$)=337 [MH$^+$], R$_t$=0.86 min, UV purity=95%.

Combined estimated purity=88%.

Intermediate 17—Synthesis of (9H-fluoren-9-yl) methyl 4-({bis[(2S,3R)-2,3-dihydroxy-3-[(4R,5R)-5-hydroxy-2-phenyl-1,3-dioxan-4-yl]propyl] amino}methyl)piperidine-1-carboxylate

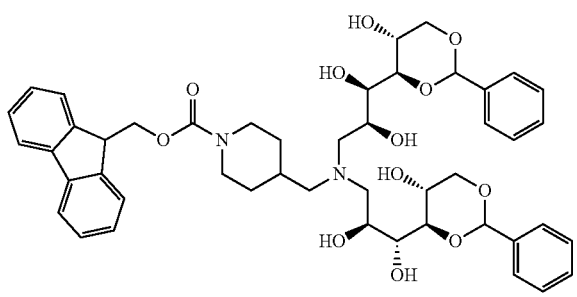

AcOH (3.11 ml, 54.3 mmol) was added to a solution of (9H-fluoren-9-yl)methyl 4-(aminomethyl)piperidine-1-carboxylate hydrochloride, Intermediate 16 (5.56 g, 14.9 mmol) and 4,6-O-benzylidene-D-glucopyranose (14.6 g, 54.3 mmol) in MeOH (100 ml). The reaction was stirred at RT for 40 min then NaCNBH$_3$ (3.41 g, 54.3 mmol) was added in portions over 50 min. The resulting solution was stirred at RT for 17 h. The reaction mixture was re-treated with 4,6-O-benzylidene-D-glucopyranose (7.29 g, 27.2 mmol) and AcOH (1.56 ml, 27.2 mmol) then stirred at RT for 30 min. NaCNBH$_3$ (1.71 g, 27.2 mmol) was added in portions over 1 h. The resulting solution was stirred at RT for a further 70 h then added onto saturated aqueous NaHCO$_3$ solution (200 ml) in portions over 30 min. The resultant suspension was stirred at RT for 1 h then filtered. The solid was washed with water (100 ml) then dried in vacuo to afford a white solid (13.8 g). A portion (5.55 g) of the crude material thus obtained was purified by flash column chromatography on C18 (400 g). The column was eluted with MeCN:H$_2$O+0.1% NH$_4$OH using the following gradient (% MeCN, column volumes): 10%, 2 CVs; 10-57%, 16 CVs; 57%, 9 CV; 59-63%, 2 CVs; 100%, 3 CVs. The desired fractions were combined and concentrated in vacuo to afford the product as a beige solid (2.99 g, 23%).

$^1$H NMR (500 MHz, CD$_3$OD-d$_4$) δ 7.86-7.75 (m, 2H), 7.65-7.55 (m, 2H), 7.53-7.44 (m, 4H), 7.43-7.37 (m, 2H), 7.36-7.27 (m, 8H), 5.51 (s, 2H), 4.64-4.36 (m, 5H), 4.27-4.20 (m, 3H), 4.04-3.92 (m, 4H), 3.86 (dd, J=5.7, 2.3 Hz, 2H), 3.71 (dd, J=9.3, 2.4 Hz, 2H), 3.64-3.57 (m, 2H), 2.73-2.58 (m, 3H), 2.54-2.44 (m, 2H), 2.36-2.23 (m, 2H), 1.81-1.42 (m, 3H), 0.89-0.58 (m, 2H). LC/MS (System B): m/z (ESI$^+$)=841 [MH$^+$], R$_t$=4.78 min, UV purity=95%.

Intermediate 18—Synthesis of (1R,2S)-3-{[(2S,3R)-2,3-dihydroxy-3-[(4R,5R)-5-hydroxy-2-phenyl-1,3-dioxan-4-yl]propyl][(piperidin-4-yl)methyl]amino}-1-[(4R,5R)-5-hydroxy-2-phenyl-1,3-dioxan-4-yl] propane-1,2-diol; bis(formic acid)

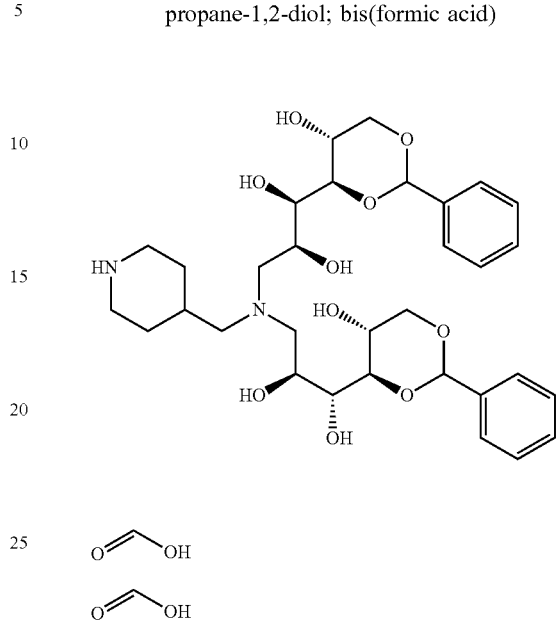

Piperidine (3.3 ml, 33.41 mmol) was added to a stirred solution of (9H-fluoren-9-yl)methyl 4-({bis[(2S,3R)-2,3-dihydroxy-3-[(4R,5R)-5-hydroxy-2-phenyl-1,3-dioxan-4-yl] propyl]amino}methyl)piperidine-1-carboxylate, Intermediate 17 (2.81 g, 3.34 mmol) in THF (40 ml). The reaction mixture was stirred at RT for 18 h then concentrated in vacuo. The residue was suspended in Et$_2$O (30 ml) with sonication then the resultant suspension was filtered. The solid collected was rinsed with Et$_2$O (20 ml) then dried under vacuum to afford a white solid (3.07 g). A sample (1.78 g) of the crude solid was purified by flash column chromatography on C18 (120 g). The column was eluted with MeCN:water+0.1% formic acid using the following gradient (% MeCN, column volumes): 10%, 2 CV; 10-16%, 1.5 CV; 16%, 2.5 CV; 16-39%, 6 CV; 39-100%, 1.5 CV; 100% 2 CV. The remaining crude solid material was purified by flash column chromatography on C18 (120 g). The column was eluted with MeCN:water+0.1% formic acid using the following gradient (% MeCN, column volumes): 10%, 2 CV; 10-14%, 2 CV; 14%, 2 CV; 14-17%, 1 CV; 17-55%, 7 CV; 55-100%, 1 CV; 100% 4 CV. The desired fractions from both columns were combined and concentrated in vacuo to afford the product as an off-white solid (1.58 g, 67%).

$^1$H NMR (500 MHz, CD$_3$OD) δ 8.33 (s, 2H), 7.53-7.45 (m, 4H), 7.41-7.31 (m, 6H), 5.53 (s, 2H), 4.25 (dd, J=10.7, 5.4 Hz, 2H), 4.02 (dt, J=8.9, 4.5 Hz, 2H), 3.96 (td, J=10.1, 5.4 Hz, 2H), 3.89 (dd, J=5.2, 2.4 Hz, 2H), 3.74 (dd, J=9.4, 2.4 Hz, 2H), 3.62 (t, J=10.5 Hz, 2H), 3.30-3.20 (m, 2H), 2.96-2.80 (m, 4H), 2.78-2.68 (m, 2H), 2.65-2.58 (m, 2H), 2.09-2.00 (m, 1H), 1.92-1.68 (m, 2H), 1.33-1.18 (m, 2H).

LC/MS (System A): m/z (ESI$^+$)=619 [MH$^+$], R$_t$=0.73 min, UV purity=100%.

Intermediate 19—Synthesis of (2R,3R,4R,5S)-6-{[(2S,3R,4R,5R)-2,3,4,5,6-pentahydroxyhexyl][(piperidin-4-yl)methyl]amino}hexane-1,2,3,4,5-pentol dihydrochloride

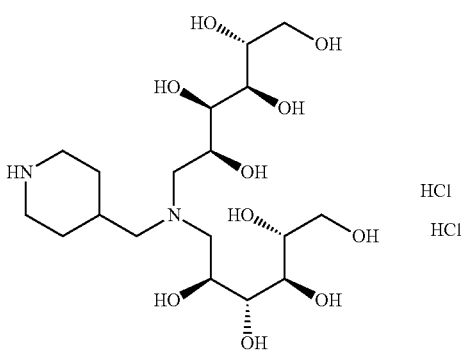 [SMILES: OC[C@@H](O)[C@@H](O)[C@H](O)[C@@H](O)CN(CC1CCNCC1)C[C@H](O)[C@@H](O)[C@H](O)[C@H](O)CO ; Cl ; Cl]

A solution of (1R,2S)-3-{[(2S,3R)-2,3-dihydroxy-3-[(4R,5R)-5-hydroxy-2-phenyl-1,3-dioxan-4-yl]propyl][(piperidin-4-yl)methyl]amino}-1-[(4R,5R)-5-hydroxy-2-phenyl-1,3-dioxan-4-yl]propane-1,2-diol; bis(formic acid), Intermediate 18 (1.52 g, 2.14 mmol) in aqueous HCl (2 M, 23 ml, 46 mmol) was stirred at RT for 4.5 h. The reaction was concentrated in vacuo to afford a viscous yellow gum (1.18 g, quantitative based on 93% estimated purity).

$^1$H NMR (500 MHz, D$_2$O) δ 4.32-4.21 (m, 2H), 3.89-3.81 (m, 4H), 3.81-3.75 (m, 2H), 3.72-3.59 (m, 4H), 3.56-3.48 (m, 6H), 3.39 (d, J=6.9 Hz, 2H), 3.09 (tt, J=13.0, 3.3 Hz, 2H), 2.40-2.27 (m, 1H), 2.21-2.13 (m, 1H), 2.06-1.99 (m, 1H), 1.66-1.53 (m, 2H).

LC/MS (System C): m/z (ESI$^+$)=443 [MH$^+$], R$_t$=0.32 min, ELS purity=100%.

Intermediate 20—Synthesis of formic acid; tert-butyl (3R)-3-{bis[(2S,3R)-2,3-dihydroxy-3-[(4R,5R)-5-hydroxy-2-phenyl-1,3-dioxan-4-yl]propyl]amino}pyrrolidine-1-carboxylate

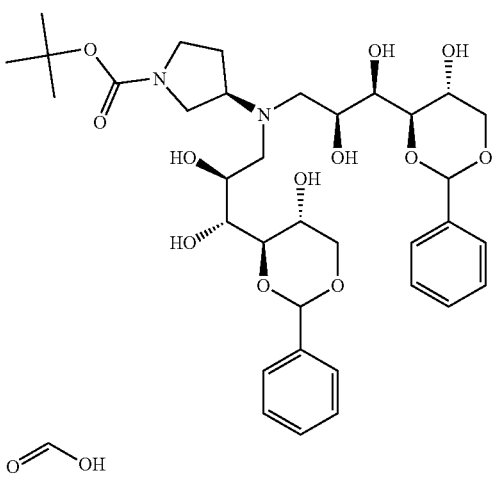

2-Picoline borane complex (0.86 g, 8.05 mmol) was added to a suspension of tert-butyl (3R)-3-aminopyrrolidine-1-carboxylate (500 mg, 2.68 mmol) and 4,6-O-benzylidene-D-glucopyranose (2.88 g, 10.7 mmol) in Methanol (5 ml). The mixture was heated at 60° C. for 17 h. The reaction mixture was allowed to cool to RT then concentrated in vacuo. The residue was partitioned between EtOAc (15 ml) and water (15 ml). The phases were separated then the organic phase was washed with water (15 ml) and brine (15 ml) then dried over Na$_2$SO$_4$ and concentrated in vacuo. The crude material was purified by flash column chromatography on C18 (60 g, Ultra). The column was eluted with MeCN:H$_2$O+0.1% formic acid using the following gradient (% MeCN, column volumes): 10%, 2 CVs; 10-40%, 10 CVs; 40-100%, 2 CVs; 100%, 2 CVs. The desired fractions were combined and concentrated in vacuo then the residual aqueous solution was lyophilised to afford the product as a white solid (1.39 g, 70%).

1H NMR (500 MHz, Methanol-d4) δ 8.29 (s, 1H), 7.53-7.44 (m, 4H), 7.42-7.30 (m, 6H), 5.53 (s, 2H), 4.26 (dd, J=10.6, 5.4 Hz, 2H), 4.10-4.01 (m, 2H), 4.01-3.92 (m, 2H), 3.91 (dd, J=5.3, 2.2 Hz, 2H), 3.77 (dd, J=9.4, 2.2 Hz, 2H), 3.74-3.67 (m, 1H), 3.66-3.54 (m, 3H), 3.26-3.17 (m, 1H), 3.09-2.80 (m, 5H), 2.04-1.86 (m, 1H), 1.86-1.68 (m, 1H), 1.47 (s, 9H). LC/MS (System A): m/z (ESI$^+$)=691 [MH$^+$], R$_t$=0.93 min, UV purity=100%.

Intermediate 21—Synthesis of (2R,3R,4R,5S)-6-{[(2S,3R,4R,5R)-2,3,4,5,6-pentahydroxyhexyl][(3R)-pyrrolidin-3-yl]amino}hexane-1,2,3,4,5-pentol dihydrochloride

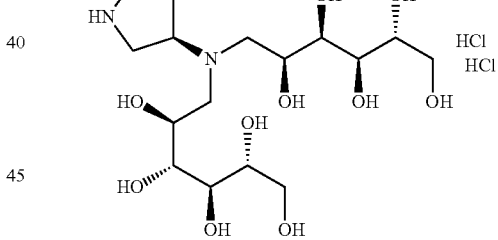

A suspension of formic acid; tert-butyl (3R)-3-{bis[(2S,3R)-2,3-dihydroxy-3-[(4R,5R)-5-hydroxy-2-phenyl-1,3-dioxan-4-yl]propyl]amino}pyrrolidine-1-carboxylate, Intermediate 20 (1.39 g, 1.89 mmol) in aqueous HCl (2 M, 30 ml, 60 mmol) was stirred at RT for 18 h.

The reaction mixture was concentrated in vacuo then re-dissolved in water (20 ml) and lyophilised to afford the product as a cream foam (1.11 g, quantitative based on 83% estimated purity).

$^1$H NMR (500 MHz, D$_2$O) δ 4.67 (p, J=8.4 Hz, 1H), 4.33-4.28 (m, 2H), 3.99-3.92 (m, 1H), 3.88 (dd, J=5.0, 2.3 Hz, 2H), 3.83 (dd, J=11.8, 3.0 Hz, 2H), 3.81-3.76 (m, 2H), 3.75-3.64 (m, 6H), 3.63-3.58 (m, 2H), 3.52-3.46 (m, 2H), 3.47-3.39 (m, 1H), 2.75-2.67 (m, 1H), 2.37-2.28 (m, 1H).

LC/MS (System A): m/z (ESI$^+$)=415 [MH$^+$], R$_t$=0.13 min, ELS purity=100%.

Intermediate 22—Synthesis of formic acid; tert-butyl N-(2-{bis[(2S,3R)-2,3-dihydroxy-3-[(4R,5R)-5-hydroxy-2-phenyl-1,3-dioxan-4-yl]propyl]amino}ethyl)carbamate

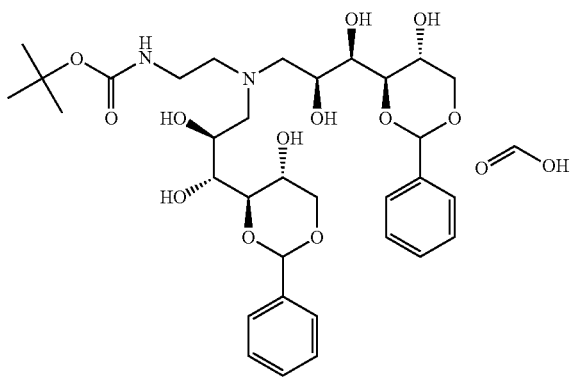

4,6-O-Benzylidene-D-glucopyranose (10.05 g, 37.45 mmol) was added to a solution of tert-butyl N-(2-aminoethyl)carbamate (1.50 g, 9.36 mmol) in MeOH (50 ml). The reaction was stirred at RT for 15 min before then AcOH (2.14 ml, 37.5 mmol) was added. The reaction was stirred at RT for a further 15 min then NaCNBH$_3$ (2.35 g, 37.5 mmol) was added portionwise over 5 min. The reaction was stirred at RT for 16 h then saturated aqueous NaHCO$_3$ solution (50 ml) was added dropwise over 15 min. Further saturated aqueous NaHCO$_3$ solution (50 ml) was added, followed by EtOAc (50 ml). The reaction was stirred at RT for 15 min then transferred to a separating funnel. More EtOAc (100 ml) was added then the phases were separated. The aqueous phase was extracted with EtOAc (150 ml), then the combined organic phases were washed with saturated aqueous NaHCO$_3$ solution (4×200 ml) and brine (50 ml), then dried over Na$_2$SO$_4$, filtered and concentrated in vacuo. The crude material was purified by flash column chromatography on C18 (400 g, Ultra). The column was eluted with MeCN:H$_2$O+0.1% formic acid using the following gradient (% MeCN, column volumes): 10%, 2 CVs; 10-49%, 8 CVs; 49-54%, 0.5 CVs; 54-100%, 1 CV. The desired fractions were combined and concentrated in vacuo then the residual aqueous solution was lyophilised to afford the product as a white solid (2.77 g, 42%).

$^1$H NMR (500 MHz, CD$_3$OD) δ 8.34 (s, 1H), 7.53-7.43 (m, 4H), 7.40-7.26 (m, 6H), 5.52 (s, 2H), 4.25 (dd, J=10.7, 5.4 Hz, 2H), 4.14 (q, J=5.7 Hz, 2H), 3.94 (td, J=10.0, 5.4 Hz, 2H), 3.89 (dd, J=5.0, 2.3 Hz, 2H), 3.75 (dd, J=9.4, 2.2 Hz, 2H), 3.61 (t, J=10.5 Hz, 2H), 3.26-2.99 (m, 8H), 1.42 (s, 9H).

LC/MS (System A): m/z (ESI$^+$)=665 [MH$^+$], R$_t$=0.94 min, UV purity=100%.

Intermediate 23—Synthesis of (2R,3R,4R,5S)-6-[(2-aminoethyl)[(2S,3R,4R,5R)-2,3,4,5,6-pentahydroxyhexyl]amino]hexane-1,2,3,4,5-pentol dihydrochloride

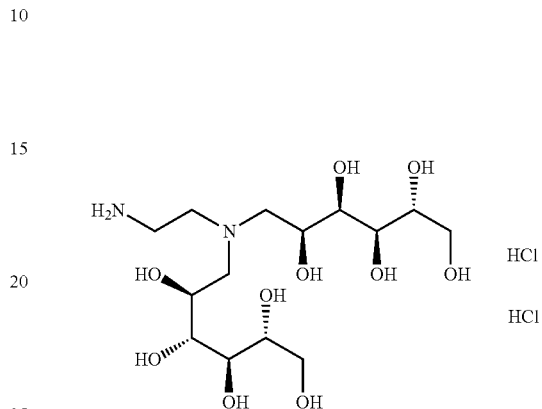

A suspension of formic acid; tert-butyl N-(2-{bis[(2S,3R)-2,3-dihydroxy-3-[(4R,5R)-5-hydroxy-2-phenyl-1,3-dioxan-4-yl]propyl]amino}ethyl)carbamate, Intermediate 22 (1.5 g, 2.11 mmol) in aqueous HCl (2 M, 21 ml, 42 mmol) was stirred at RT for 68 h. The reaction was concentrated in vacuo, then re-dissolved in MeCN/water and concentrated in vacuo. The residue was re-dissolved in MeCN/water then lyophilised to afford the product as a white solid (1.03 g, 99% based on 94% estimated purity).

$^1$H NMR (500 MHz, D$_2$O) δ 4.30 (dt, J=8.9, 4.7 Hz, 2H), 3.88 (dd, J=4.9, 2.2 Hz, 2H), 3.86-3.71 (m, 6H), 3.71-3.66 (m, 4H), 3.61-3.50 (m, 6H).

LC/MS (System A): m/z (ESI$^+$)=389 [MH$^+$], R$_t$=0.14 min, ELS purity=100%.

Intermediate 24—Synthesis of tert-butyl N-[2-(2-{2-[2-({[(9H-fluoren-9-yl)methoxy]carbonyl}amino)ethoxy]ethoxy}ethoxy)ethyl]carbamate

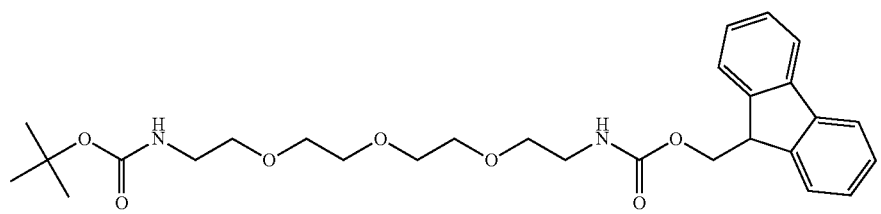 [SMILES: CC(C)(C)OC(=O)NCCOCCOCCOCCNC(=O)OCC1c2ccccc2-c2ccccc21]

NaHCO$_3$ (0.57 g, 6.84 mmol) was added portionwise over 2 min to a stirred solution of tert-butyl N-[2-[2-[2-(2-aminoethoxy)ethoxy]ethoxy]ethyl]carbamate (1.00 g, 3.42 mmol) in MeCN (15 ml) and water (15 ml) RT. A solution of (2,5-dioxopyrrolidin-1-yl) 9H-fluoren-9-ylmethyl carbonate (1.15 g, 3.42 mmol) in MeCN (15 ml) was added dropwise over 30 min. The resulting solution was stirred at RT for 18 h. EtOAc (30 ml) and brine (10 ml) were added then the phases were separated. The aqueous phase was extracted with EtOAc (20 ml). The combined organic extracts were washed with brine (45 ml), dried over MgSO4, then concentrated in vacuo to afford the product as a yellow gum (1.61 g, 76% yield).

$^{1}$H NMR (500 MHz, DMSO-$d_6$) δ 7.89 (d, J=7.5 Hz, 2H), 7.72-7.61 (m, 2H), 7.41 (t, J=7.4 Hz, 2H), 7.37-7.27 (m, 3H), 6.74 (t, J=5.4 Hz, 1H), 4.29 (d, J=6.9 Hz, 2H), 4.21 (t, J=6.9 Hz, 1H), 3.55-3.44 (m, 8H), 3.40 (t, J=6.0 Hz, 2H), 3.36 (t, J=6.1 Hz, 2H), 3.13 (q, J=5.9 Hz, 2H), 3.05 (q, J=6.0 Hz, 2H), 1.36 (s, 9H).

LC/MS (System A): m/z (ESI$^+$)=537 [M+Na$^+$], R$_t$=1.28 min, UV purity=83%.

Intermediate 25—Synthesis of (9H-fluoren-9-yl) methyl N-(2-{2-[2-(2-aminoethoxy)ethoxy] ethoxy}ethyl)carbamate hydrochloride

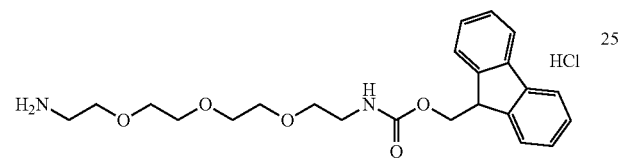

HCl solution in dioxane (4 M, 2 ml, 8 mmol) was added to a stirred solution of tert-butyl N-[2-(2-{2-[2-({[(9H-fluoren-9-yl)methoxy]carbonyl}amino)ethoxy]ethoxy}ethoxy)ethyl]carbamate, Intermediate 24 (83%, 1.61 g, 2.61 mmol) in MeCN (16 ml). The resulting solution was left to stir at RT for 22 h then concentrated in vacuo to afford the product as a yellow gum (1.57 g, quantitative based on 75% estimated purity).

$^{1}$H NMR (500 MHz, DMSO-$d_6$) δ 7.89 (d, J=7.5 Hz, 2H), 7.83 (s, 3H), 7.69 (d, J=7.4 Hz, 2H), 7.42 (t, J=7.4 Hz, 2H), 7.37-7.29 (m, 3H), 4.30 (d, J=6.9 Hz, 2H), 4.21 (t, J=6.8 Hz, 1H), 3.60-3.57 (m, 2H), 3.56-3.48 (m, 8H), 3.40 (t, J=6.0 Hz, 2H), 3.13 (q, J=5.9 Hz, 2H), 2.98-2.92 (m, 2H). 20 wt % residual solvent.

LC/MS (System A): m/z (ESI$^+$)=415 [MH$^+$], R$_t$=0.89 min, UV purity=92%.

Intermediate 26—Synthesis of (9H-fluoren-9-yl) methyl N-[(14S,15R)-12-[(2S,3R)-2,3-dihydroxy-3-[(4R,5R)-5-hydroxy-2-phenyl-1,3-dioxan-4-yl]propyl]-14,15-di hydroxy-15-[(4R,5R)-5-hydroxy-2-phenyl-1,3-dioxan-4-yl]-3,6,9-trioxa-12-azapentadecan-1-yl]carbamate; formic acid

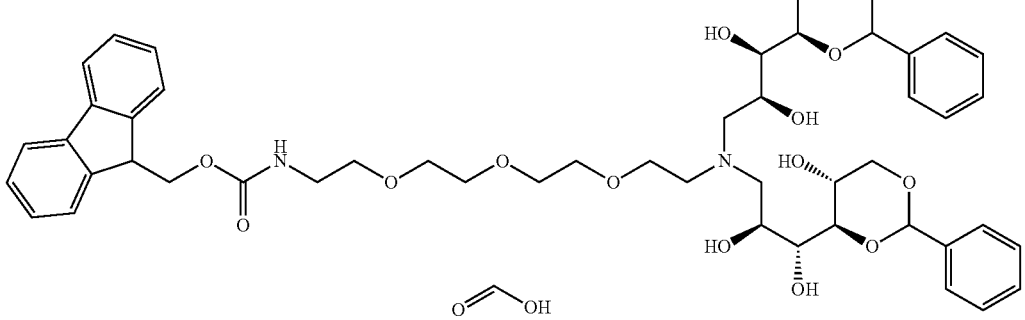

AcOH (737 μL, 12.9 mmol) was added to a solution of (9H-fluoren-9-yl)methyl N-(2-{2-[2-(2-aminoethoxy)ethoxy]ethoxy}ethyl)carbamate hydrochloride, Intermediate 25 (75%, 1.57 g, 3.22 mmol) and 4,6-O-benzylidene-D-glucopyranose (3.46 g, 12.9 mmol) in MeOH (30 ml). The reaction was stirred at RT for 45 min. NaCNBH$_3$ (809 mg, 12.9 mmol) was added portionwise over 50 min. The resultant solution was stirred at RT for 40 h. The reaction mixture was treated with 4,6-O-benzylidene-D-glucopyranose (1.73 g, 6.45 mmol), AcOH (368 μL, 6.43 mmol) and MeOH (10 ml). The reaction was stirred at RT for 1 h then NaCNBH$_3$ (403 mg, 6.41 mmol) was added portionwise over 20 min. MeOH (10 ml) was added then the reaction mixture was stirred at RT for 70 h. Saturated aqueous NaHCO$_3$ solution (100 ml) was added portionwise over 5 min then EtOAc (100 ml) was added. The phases were separated then the aqueous phase was extracted with EtOAc (3×30 ml). The combined organic phases were washed with saturated aqueous NaHCO$_3$ solution (2×50 ml), brine (50 ml), then dried over MgSO$_4$, filtered and concentrated in vacuo to afford a brown gum (3.86 g). A portion (2 g) of the crude material was purified by flash column chromatography on C18 (120 g, Ultra). The column was eluted with MeCN:H$_2$O+0.1% formic acid using the following gradient (% MeCN, column volumes): 10%, 2 CVs; 10-31%, 8 CVs; 31%, 4.5 CV; 31-35%, 1.5 CVs; 35-47%, 1 CV; 47-61%, 1.5 CV; 100% 2 CV. The remaining crude material was purified by flash column chromatography on C18 (120 g, Ultra). The column was eluted with MeCN:H$_2$O+0.1% formic acid using the following gradient (% MeCN, column volumes): 10%, 2 CVs; 10-27%, 4 CVs; 27%, 0.5 CV; 27-68%, 9 CV; 68%, 0.5 CVs; 68-78%, 2 CV; 78-100%, 1.5 CV; 100% 1 CV. The desired fractions from both columns were combined and concentrated in vacuo to afford the product as a light brown resin (1.30 g, 48%).

$^1$H NMR (500 MHz, CD$_3$OD) δ 8.44 (s, 1H), 7.81 (d, J=7.5 Hz, 2H), 7.68-7.59 (m, 2H), 7.52-7.44 (m, 4H), 7.44-7.37 (m, 2H), 7.37-7.30 (m, 8H), 5.52 (s, 2H), 4.36 (d, J=6.8 Hz, 2H), 4.28-4.15 (m, 5H), 3.98-3.88 (m, 4H), 3.75 (dd, J=9.4, 2.3 Hz, 2H), 3.67-3.44 (m, 14H), 3.40-3.33 (m, 4H), 3.31-3.21 (m, 4H). LC/MS (System A): m/z (ESI$^+$)=919 [MH$^+$], R$_t$=1.02 min, UV purity=93%.

Intermediate 27—Synthesis of (14S,15R)-1-amino-12-[(2S,3R)-2,3-dihydroxy-3-[(4R,5R)-5-hydroxy-2-phenyl-1,3-dioxan-4-yl]propyl]-15-[(4R,5R)-5-hydroxy-2-phenyl-1,3-dioxan-4-yl]-3,6,9-trioxa-12-azapentadecane-14,15-diol; bis(formic acid)

Piperidine (1.34 ml, 13.6 mmol) was added to a stirred solution of (9H-fluoren-9-yl)methyl N-[(14 S, 15R)-12-[(2S, 3R)-2,3-dihydroxy-3-[(4R,5R)-5-hydroxy-2-phenyl-1,3-dioxan-4-yl]propyl]-14,15-dihydroxy-15-[(4R,5R)-5-hydroxy-2-phenyl-1,3-dioxan-4-yl]-3,6,9-trioxa-12-azapentadecan-1-yl]carbamate; formic acid, Intermediate 26 (93%, 1.25 g, 1.20 mmol) in THF (15 ml). The resulting solution was stirred at RT for 6 h then concentrated in vacuo. The residue thus obtained was suspended in Et$_2$O (10 ml) with sonication. The supernatant was decanted off then the process was repeated with more Et$_2$O (10 ml). The residue thus obtained was purified by flash column chromatography on C18 (120 g, Ultra). The column was eluted with MeCN:H$_2$O+0.1% formic acid using the following gradient (% MeCN, column volumes): 10%, 2 CVs; 10-13%, 1.5 CVs; 13%, 2.5 CV; 13-22%, 5.5 CVs; 22-60%, 5.5 CV; 60-83%, 2 CV; 100% 2 CV. The desired fractions were combined and concentrated in vacuo to afford the product as a yellow solid (849 mg, 89%).

$^1$H NMR (500 MHz, CD$_3$OD) δ 8.40 (s, 2H), 7.54-7.43 (m, 4H), 7.41-7.28 (m, 6H), 5.53 (s, 2H), 4.26 (dd, J=10.7, 5.4 Hz, 2H), 4.20-4.12 (m, 2H), 3.97-3.87 (m, 4H), 3.74 (dd, J=9.4, 2.6 Hz, 2H), 3.70-3.54 (m, 14H), 3.29-3.19 (m, 3H), 3.16-3.08 (m, 2H), 3.07-2.99 (m, 1H), 2.98-2.86 (m, 2H).

LC/MS (System A): m/z (ESI$^+$)=697 [MH$^+$], R$_t$=0.74 min, UV purity=100%.

Intermediate 28—Synthesis of (14S,15R,16R,17R)-1-amino-12-[(2S,3R,4R,5R)-2,3,4,5,6-pentahydroxyhexyl]-3,6,9-trioxa-2-azaoctadecane-14,15,16,17,18-pentol dihydrochloride

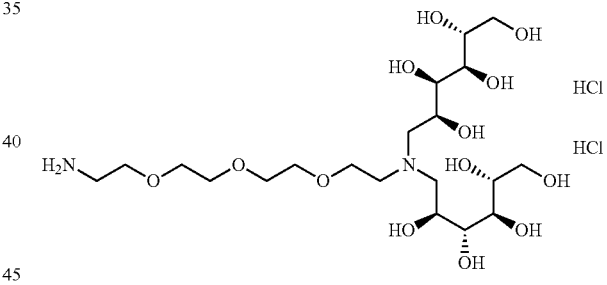

A solution of (14S,15R)-1-amino-12-[(2S,3R)-2,3-dihydroxy-3-[(4R,5R)-5-hydroxy-2-phenyl-1,3-dioxan-4-yl]propyl]-15-[(4R,5R)-5-hydroxy-2-phenyl-1,3-dioxan-4-yl]-

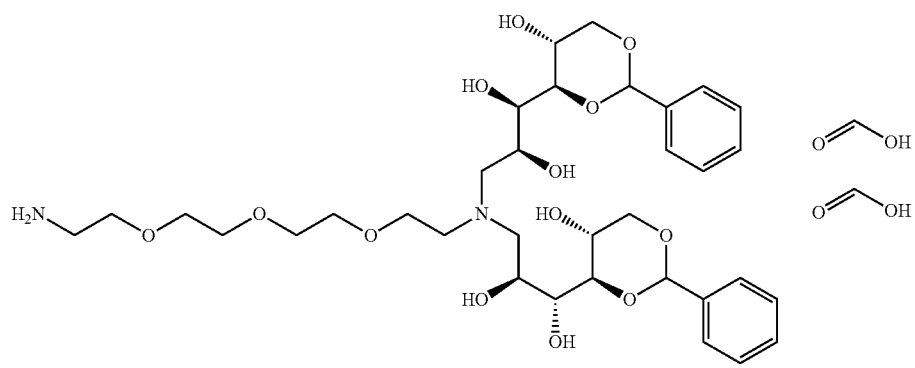

3,6,9-trioxa-12-azapentadecane-14,15-diol; bis(formic acid), Intermediate 27 (845 mg, 1.07 mmol) in aqueous HCl solution (2 M, 10 ml, 20 mmol) was stirred at RT for 5.5 h then concentrated in vacuo. The residue thus obtained was re-dissolved in water (15 ml) then lyophilised to afford a pale yellow gum (660 mg, quantitative based on 96% estimated purity).

$^1$H NMR (500 MHz, D$_2$O) δ 4.30-4.22 (m, 2H), 3.96-3.91 (m, 2H), 3.88-3.82 (m, 4H), 3.81-3.63 (m, 17H), 3.59-3.48 (m, 5H), 3.26-3.20 (m, 2H).

LC/MS (System C): m/z (ESI$^+$)=521 [MH$^+$], R$_t$=0.33 min, ELS purity=100%.

Intermediate 29—Synthesis of tert-butyl N-[2-(4-bromophenyl)ethyl]carbamate

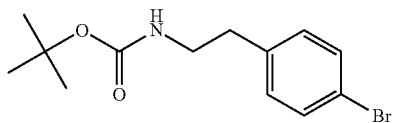 [SMILES: CC(C)(C)OC(=O)NCCc1ccc(Br)cc1]

Di-tert-butyl dicarbonate (3.93 g, 18.0 mmol) was added to a cooled (0° C.) stirred solution of 2-(4-bromophenyl) ethanamine (3.00 g, 15.0 mmol) in THF (20 ml). The resulting solution was allowed to warm to RT then stirred at RT for 18 h. The reaction mixture was partitioned between EtOAc (30 ml) and saturated aqueous NaHCO$_3$ solution (50 ml). The phases were separated then the aqueous phase was extracted with EtOAc (15 ml). The combined organic phases were washed with brine (50 ml), dried over MgSO$_4$, then concentrated in vacuo. The crude material was dissolved in the minimum volume of CH$_2$Cl$_2$, pre-adsorbed onto silica, then purified by flash column chromatography on a silica column (25 g). The column was eluted with EtOAc:heptane, using the following gradient (% EtOAc, column volumes): 0%, 1 CV; 0-8%, 2.5 CV; 8-12%, 1 CV; 12%, 3.5 CV; 12-27%, 5.5 CV; 27-30%, 0.5 CV; 30%, 2 CV; 30-90%, 4 CV; 100% 1 CV. The desired fractions were combined and concentrated in vacuo to afford the product as a white solid (3.99 g, 88%).

$^1$H NMR (500 MHz, DMSO-d$_6$) δ 7.50-7.42 (m, 2H), 7.19-7.11 (m, 2H), 6.86 (t, J=5.3 Hz, 1H), 3.12 (q, J=6.6 Hz, 2H), 2.70-2.63 (m, 2H), 1.41-1.26 (m, 9H).

LC/MS (System A): R$_t$=1.27 min, UV purity=99%.

Intermediate 30—Synthesis of tert-butyl N-{2-[4'-(cyanomethyl)-[1,1'-biphenyl]-4-yl]ethyl}carbamate

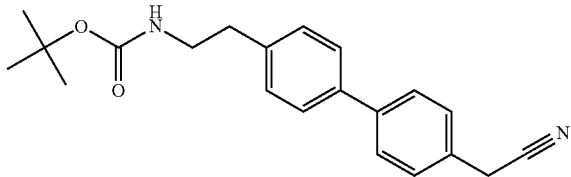 [SMILES: CC(C)(C)OC(=O)NCCc1ccc(-c2ccc(CC#N)cc2)cc1]

A mixture of tert-butyl N-[2-(4-bromophenyl)ethyl]carbamate, Intermediate 29 (4.09 g, 13.6 mmol), [4-cyanomethyl)phenyl]boronic acid (2.63 g, 16.4 mmol) and K$_2$CO$_3$ (5.65 g, 40.9 mmol) in 1,4-dioxane (105 ml) was degassed by bubbling a stream nitrogen through the mixture for 5 min. Pd(dppf)C$_2$.CH$_2$Cl$_2$ (445 mg, 0.545 mmol) was added and degassing was continued for a further 5 min. The reaction mixture was heated at 80° C. for 15 h then at 100° C. for 7 h. The reaction was allowed to cool to RT then retreated with K$_2$CO$_3$ (3.76 g, 27.2 mmol) and degassed for 5 min. Pd(dppf)Cl$_2$.CH$_2$Cl$_2$ (445 mg, 0.545 mmol) was added then the mixture was degassed for a further 5 min. The resultant mixture was heated at 100° C. for 24 h then allowed to cool to RT. The reaction was retreated with K$_2$CO$_3$ (1.88 g, 13.6 mmol) and [4-cyanomethyl)phenyl]boronic acid (0.88 g, 5.5 mmol) then degassed for 10 min. Pd(dppf)Cl$_2$.CH$_2$Cl$_2$ (445 mg, 0.545 mmol) was added then the mixture was degassed for a further 5 min. The reaction was heated at 100° C. for 18 h then allowed to cool to RT. The reaction mixture was filtered then the collected solids were washed with EtOAc (50 ml). The combined filtrate was concentrated in vacuo. The residue was re-dissolved in EtOAc:heptane (1:1) then filtered through a silica pad. The pad was rinsed with EtOAc:heptane (1:1, 200 ml). The filtrate was concentrated in vacuo to afford an off-white solid (3.94 g). The silica pad was rinsed through further with EtOAc (200 ml) to afford a brown solid (1.68 g). The brown solid from the EtOAc filtrate was pre-adsorbed onto silica, then purified by flash column chromatography on a silica column (50 g). The column was eluted with EtOAc:heptane, using the following gradient (% EtOAc, column volumes): 0%, 1 CV; 0-30%, 11 CV; 30%, 20 CV; 30-45%, 4.5 CV; 45%, 7.5 CV; 45-50%, 1 CV; 50%, 15 CV. The desired fractions were combined and concentrated in vacuo to afford an off-white solid (1.00 g, 21%).

$^1$H NMR (500 MHz, DMSO-d$_6$) δ 7.67 (d, J=8.2 Hz, 2H), 7.59 (d, J=8.2 Hz, 2H), 7.42 (d, J=8.2 Hz, 2H), 7.28 (d, J=8.1 Hz, 2H), 6.90 (t, J=5.5 Hz, 1H), 4.07 (s, 2H), 3.17 (q, J=6.5 Hz, 2H), 2.73 (t, J=7.4 Hz, 2H), 1.44-1.29 (m, 9H).

LC/MS (System A): R$_t$=1.27 min, UV purity=97%.

Intermediate 31—Synthesis of tert-butyl N-{2-[4'-(2-aminoethyl)-[1,1'-biphenyl]-4-yl]ethyl}carbamate

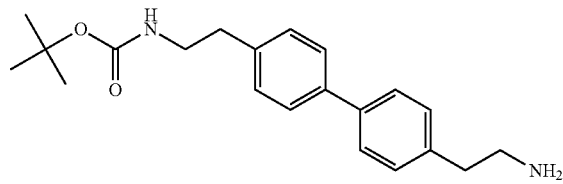 [SMILES: CC(C)(C)OC(=O)NCCc1ccc(-c2ccc(CCN)cc2)cc1]

A mixture of tert-butyl N-{2-[4'-(cyanomethyl)-[1,1'-biphenyl]-4-yl]ethyl}carbamate, Intermediate 30 (570 mg, 1.69 mmol), aqueous ammonia solution (35%, 0.5 ml) and aqueous Raney nickel slurry (50%, 2 ml) in EtOH (15 mL) and DMF (5 mL) was stirred under a hydrogen atmosphere for 18 h. The reaction mixture was filtered through a Celite pad. The pad was rinsed with EtOH (50 ml) and MeOH (100 ml) then the combined filtrate was concentrated in vacuo. The residue was azeotroped with heptane (3×100 ml) then dried in vacuo to afford the product as an off-white solid (515 mg, 84%).

$^1$H NMR (500 MHz, DMSO-d$_6$) δ 7.60-7.50 (m, 4H), 7.31-7.22 (m, 4H), 6.89 (t, J=5.3 Hz, 1H), 3.19-3.13 (m, 2H), 2.78 (t, J=7.2 Hz, 2H), 2.72 (t, J=7.4 Hz, 2H), 2.66 (t, J=7.2 Hz, 2H), 1.43-1.29 (m, 9H).

LC/MS (System A): m/z (ESI$^+$)=341 [MH$^+$], R$_t$=0.93 min, UV purity=94%.

Intermediate 32—Synthesis of tert-butyl N-{2-[4'-(2-{bis[(2S,3R)-2,3-dihydroxy-3-[(4R,5R)-5-hydroxy-2-phenyl-1,3-dioxan-4-yl]propyl]amino}ethyl)-[1,1'-biphenyl]-4-yl]ethyl}carbamate

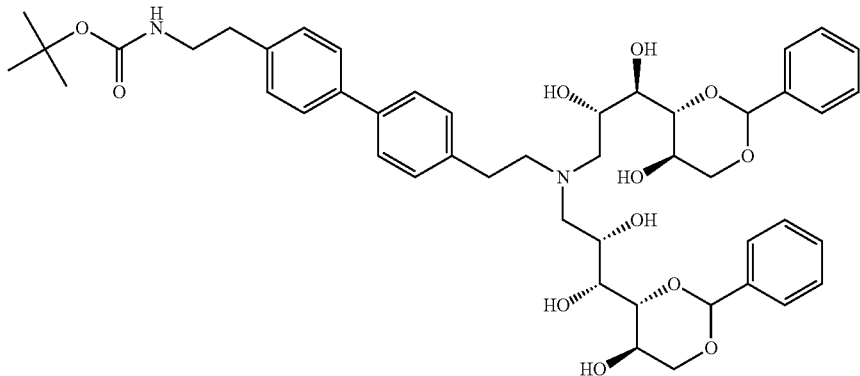

AcOH (0.33 ml, 5.8 mmol) was added to a solution of tert-butyl N-{2-[4'-(2-aminoethyl)-[1,1'-biphenyl]-4-yl]ethyl}carbamate, Intermediate 31 (94%, 515 mg, 1.42 mmol) and 4,6-O-benzylidene-D-glucopyranose (1.58 g, 5.89 mmol) in MeOH (50 ml). The reaction was left to stir at RT for 50 min then NaCNBH$_3$ (370 mg, 5.89 mmol) was added portionwise over 25 min. The resulting solution was stirred at RT for 24 h. Further 4,6-O-benzylidene-D-glucopyranose (790 mg, 2.94 mmol), AcOH (0.17 ml, 3.0 mmol) and MeOH (50 ml) were added then the reaction was left to stir at RT for 40 min. NaCNBH$_3$ (185 mg, 2.94 mmol) was added portionwise over 20 min then the reaction was left to stir at RT for 68 h. Further 4,6-O-benzylidene-D-glucopyranose (790 mg, 2.94 mmol), AcOH (0.17 ml, 3.0 mmol) and MeOH (50 ml) were added then the reaction was left to stir at RT for 30 min. NaCNBH$_3$ (185 mg, 2.94 mmol) was added portionwise over 20 min then the reaction was left to stir at RT for 18 h. Further 4,6-O-benzylidene-D-glucopyranose (790 mg, 2.94 mmol) and MeOH (25 ml) were added then the reaction heated at 40° C. for 18 h. The reaction mixture was allowed to cool to RT then saturated aqueous NaHCO$_3$ solution (40 ml) was added in portions over 15 min. The resultant mixture was stirred at RT for 30 min then the solid was collected by filtration, rinsed with water (10 ml), then dried in vacuo.

The crude solid material thus obtained was purified by flash column chromatography on C18 (120 g). The column was eluted with MeCN:H$_2$O+0.1% NH$_4$OH using the following gradient (% MeCN, column volumes): 10%, 2 CVs; 10-59%, 10 CVs; 59%, 2 CV; 59-100%, 8 CVs; 100%, 2 CVs. The desired fractions were combined and concentrated in vacuo to afford the product as a white solid (932 mg, 78%).

$^1$H NMR (500 MHz, DMSO-d$_6$) δ 7.57-7.49 (m, 2H), 7.46-7.37 (m, 6H), 7.34-7.29 (m, 6H), 7.28-7.23 (m, 2H), 7.09-7.01 (m, 2H), 6.90 (t, J=5.6 Hz, 1H), 5.48 (s, 2H), 5.14 (d, J=5.8 Hz, 2H), 4.50-4.40 (m, 4H), 4.12 (dd, J=10.5, 5.3 Hz, 2H), 3.87-3.75 (m, 4H), 3.75-3.69 (m, 2H), 3.67-3.60 (m, 2H), 3.50 (t, J=10.4 Hz, 2H), 3.21-3.10 (m, 2H), 2.82-2.65 (m, 8H), 2.57 (dd, J=12.9, 8.9 Hz, 2H), 1.43-1.29 (m, 9H).

LC/MS (System B): m/z (ESI$^+$)=845 [MH$^+$], R$_t$=4.80 min, UV purity=100%.

Intermediate 33—Synthesis of (2R,3R,4R,5S)-6-({2-[4'-(2-aminoethyl)-[1,1'-biphenyl]-4-yl]ethyl}[(2S,3R,4R,5R)-2,3,4,5,6-pentahydroxyhexyl]amino)hexane-1,2,3,4,5-pentol dihydrochloride

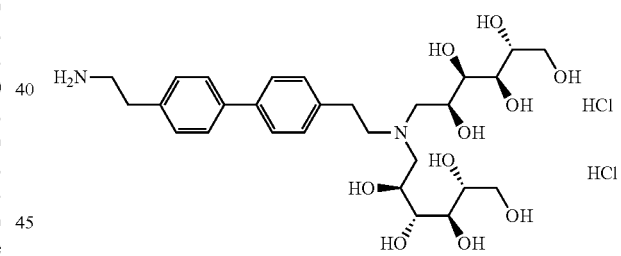

A suspension of tert-butyl N-{2-[4'-(2-{bis[(2S,3R)-2,3-dihydroxy-3-[(4R,5R)-5-hydroxy-2-phenyl-1,3-dioxan-4-yl]propyl]amino}ethyl)-[1,1'-biphenyl]-4-yl]ethyl}carbamate, Intermediate 32 (932 mg, 1.10 mmol) in aqueous HCl solution (2 M, 8.5 ml, 17 mmol) was stirred at RT for 24 h then further aqueous HCl solution (2 M, 8.5 ml, 17 mmol) was added. The reaction was left to stir at RT for a further 24 h. The reaction mixture was heated at 40° C. for 4 h the concentrated in vacuo. The residue thus obtained was dissolved in water (15 ml) then lyophilised to afford the product as a white resin (753 mg, quantitative based on 94% estimated purity).

$^1$H NMR (500 MHz, D$_2$O) δ 7.77-7.70 (m, 4H), 7.53-7.48 (m, 2H), 7.48-7.43 (m, 2H), 4.30-4.19 (m, 2H), 3.87-3.61 (m, 12H), 3.61-3.45 (m, 4H), 3.33 (t, J=7.4 Hz, 2H), 3.29-3.16 (m, 2H), 3.07 (t, J=7.4 Hz, 2H).

LC/MS (System A): m/z (ESI$^+$)=569 [MH$^+$], R$_t$=0.15 min, ELS purity=100%.

Intermediate 58—Synthesis of 6-(2-{[(tert-butoxy)carbonyl]amino}ethoxy)-1,3-diethyl-2-({[(9H-fluoren-9-yl methoxy)carbonyl]amino}methyl)-1H-1,3-benzodiazol-3-ium iodide

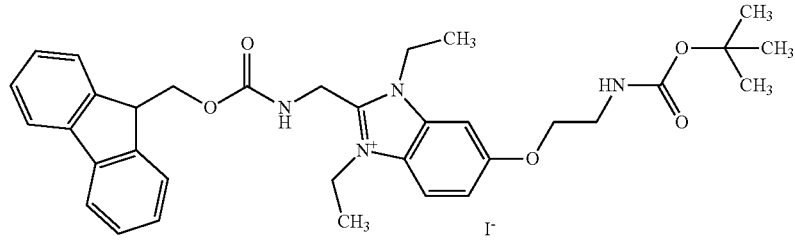 [SMILES: CCn1c(CNC(=O)OCC2c3ccccc3-c3ccccc32)[n+](CC)c2ccc(OCCNC(=O)OC(C)(C)C)cc21 ; [I-]]

Intermediate 58 was synthesised by according to literature procedures (US 2015/0018313 A1).

Intermediate 60—Synthesis tert-butyl N-[3-(3-fluoro-4-nitrophenoxy)propyl]carbamate

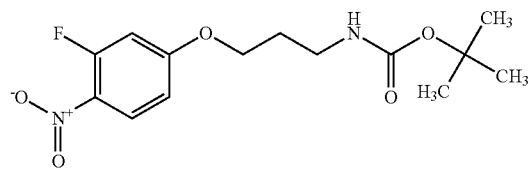

A suspension of 3-fluoro-4-nitrophenol (2.50 g, 15.9 mmol), tert-butyl (3-bromopropyl)carbamate (3.98 g, 16.7 mmol) and K$_2$CO$_3$ (2.64 g, 19.1 mmol) in acetone (15 ml) was stirred at 60° C. for 18 h. The reaction mixture was concentrated in vacuo then the residue was partitioned between EtOAc (50 ml) and water (50 ml). The phases were separated then the organic phase was extracted with water (2×50 ml) and brine (50 ml) then dried over Na$_2$SO$_4$ and concentrated in vacuo to afford the product as a viscous orange oil (4.65 g, 84%).

$^1$H NMR (500 MHz, Acetone-d6) δ 8.14 (t, J=9.2 Hz, 1H), 7.16 (dd, J=13.7, 2.5 Hz, 1H), 6.96 (dd, J=9.3, 2.6 Hz, 1H), 6.92 (t, J=5.5 Hz, 1H), 4.13 (t, J=6.2 Hz, 2H), 3.07 (q, J=6.6 Hz, 2H), 1.84 (p, J=6.5 Hz, 2H), 1.37 (s, 9H).

LC/MS (System A): m/z (ESI$^+$)=R$_t$=1.22 min, UV purity=90%.

Intermediate 61—Synthesis of tert-butyl N-{3-[3-(ethylamino)-4-nitrophenoxy]propyl}carbamate

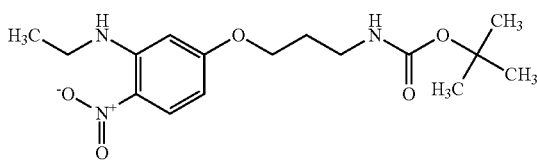

Ethylamine solution in THF (2.0 M, 10 ml, 20 mmol) was added to a mixture of tert-butyl N-[3-(3-fluoro-4-nitrophenoxy)propyl]carbamate, Intermediate 60 (90%, 4.65 g, 13.3 mmol) and K$_2$CO$_3$ (2.20 g, 16.0 mmol) in THF (30 ml). The reaction mixture was stirred at RT for 16 h then additional ethylamine solution in THF (2.0 M, 3.0 ml, 6.0 mmol) was added. The reaction mixture was left to stir at RT for a further 70 h then filtered. The filter pad was rinsed with EtOAc then the combined filtrate was extracted with water (150 ml). The organic phase was washed with water (150 ml) and brine (150 ml) then dried over Na$_2$SO$_4$ and concentrated in vacuo to afford the product as a viscous yellow/orange oil (4.69 g, 93%).

$^1$H NMR (500 MHz, DMSO-d$_6$) δ 8.26 (t, J=5.0 Hz, 1H), 8.02 (d, J=10.0 Hz, 1H), 6.92-6.86 (m, 1H), 6.30-6.27 (m, 2H), 4.09 (t, J=6.3 Hz, 2H), 3.40-3.35 (m, 2H), 3.08 (q, J=6.7 Hz, 2H), 1.84 (p, J=6.5 Hz, 2H), 1.37 (s, 9H), 1.24 (t, J=7.1 Hz, 3H).

LC/MS (System A): m/z (ESI$^+$)=R$_t$=1.30 min, m/z=340 [MH$^+$], UV purity=90%.

Intermediate 62—Synthesis of (9H-fluoren-9-yl) methyl N-{[6-(3-{[(tert-butoxy)carbonyl]amino}propoxy)-1-ethyl-1H-1,3-benzodiazol-2-yl]methyl}carbamate

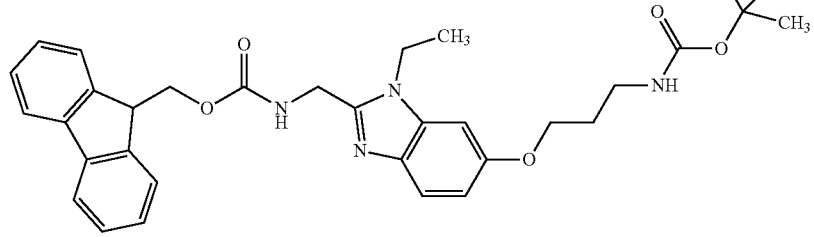

Palladium on carbon (10 wt %, 662 mg) was added to a solution of tert-butyl N-{3-[3-(ethylamino)-4-nitrophenoxy]propyl}carbamate, Intermediate 61 (90%, 4.69 g, 12.4 mmol) in EtOH (60 ml). The resulting mixture was stirred under a hydrogen atmosphere for 20 h. The reaction mixture was filtered through a Celite pad then the filtrate was concentrated in vacuo. The residue was dissolved in DMF (10 ml) to give a solution of the phenylenediamine intermediate. A solution of FMOC-glycine (3.88 g, 13.1 mmol), HATU (5.20 g, 13.7 mmol) and DIPEA (4.3 ml, 25 mmol) in DMF (20 ml) was stirred at RT for 0.5 h. The phenylenediamine DMF solution was then added and the resulting solution was stirred at RT for 1 h. Additional FMOC-glycine (2.00 g, 6.73 mmol and HATU (2.50 g, 6.57 mmol) were added then the reaction was left to stir at RT for a further 45 min. The reaction mixture was partitioned between EtOAc (100 ml) and water (100 ml). The phases were separated then the organic phase was washed with water (2×100 ml) and brine (100 ml) then dried over $Na_2SO_4$ and concentrated in vacuo to afford a red solid. The solid thus obtained was dissolved in AcOH (20 ml) then heated at 60° C. for 16 h. The reaction was allowed to cool to RT then concentrated in vacuo. The residue thus obtained was treated with saturated aqueous $NaHCO_3$ solution until pH 9 then partitioned between EtOAc (250 ml) and water (250 ml). The phases were separated then the organic phase was dried over $Na_2SO_4$ and concentrated in vacuo.

The crude material was purified by flash column chromatography on a silica column (340 g). The column was eluted with $CH_2Cl_2$:MeOH, using the following gradient (% MeOH, column volumes): 0%, 1 CV; 0-3.3%, 7 CV; 3.3%, 1 CV; 3.3-4.5%, 2 CV. The desired fractions were combined and evaporated to afford the product as a pale orange solid (4.73 g, 53%).

$^1$H NMR (500 MHz, DMSO-$d_6$) δ 7.97 (d, J=5.8 Hz, 1H), 7.91-7.87 (m, 2H), 7.72 (d, J=7.7 Hz, 2H), 7.42 (dt, J=13.6, 8.0 Hz, 3H), 7.35-7.27 (m, 3H), 7.06 (s, 1H), 6.93-6.85 (m, 1H), 6.79 (d, J=8.6 Hz, 1H), 4.46 (d, J=5.6 Hz, 2H), 4.32 (t, J=6.8 Hz, 2H), 4.24-4.16 (m, 3H), 4.01 (t, J=6.1 Hz, 2H), 3.11 (q, J=6.6 Hz, 2H), 1.89-1.82 (m, 2H), 1.37 (s, 9H), 1.25 (t, J=7.0 Hz, 3H).

LC/MS (System A): m/z (ESI$^+$)=R$_t$=1.18 min, m/z=571 [MH$^+$], UV purity=80%.

Intermediate 63—Synthesis of 6-(3-{[(tert-butoxy)carbonyl]amino}propoxy)-1,3-diethyl-2-[({[(9H-fluoren-9-yl)methoxy]carbonyl}amino)methyl]-1H-1,3-benzodiazol-3-ium iodide

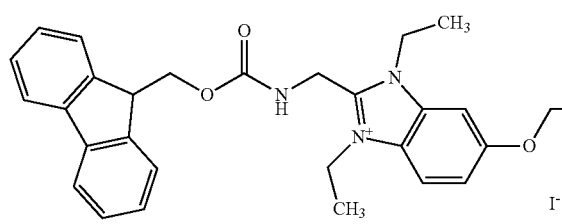

A mixture of (9H-fluoren-9-yl)methyl N-{[6-(3-{[(tert-butoxy)carbonyl]amino}propoxy)-1-ethyl-1H-1,3-benzodiazol-2-yl]methyl}carbamate, Intermediate 62 (80%, 1.50 g, 2.10 mmol) and iodoethane (1.69 ml, 21.0 mmol) in THF (15 ml) was heated under microwave irradiation for 1.5 h at 120° C. The reaction mixture was concentrated in vacuo then the crude material was purified by flash column chromatography on a silica column (100 g). The column was eluted with $CH_2Cl_2$:MeOH, using the following gradient (% MeOH, column volumes): 0%, 1 CV; 0-3.4%, 7 CV; 3.4-4.3%, 2 CV, 4.3-6.0%, 2 CV. The desired fractions were combined and evaporated to afford the product as a pale orange foam (1.03 g, 61%).

$^1$H NMR (500 MHz, DMSO-$d_6$) δ 8.24 (t, J=5.1 Hz, 1H), 7.95 (d, J=9.1 Hz, 1H), 7.86 (d, J=7.5 Hz, 2H), 7.62 (d, J=7.5 Hz, 2H), 7.56 (s, 1H), 7.36 (t, J=7.4 Hz, 2H), 7.30-7.22 (m, 3H), 6.93-6.88 (m, 1H), 4.74 (d, J=5.1 Hz, 2H), 4.55-4.47 (m, 6H), 4.22 (t, J=5.8 Hz, 1H), 4.13 (t, J=6.0 Hz, 2H), 3.12 (q, J=6.4 Hz, 2H), 1.94-1.85 (m, 2H), 1.37-1.31 (m, 15H).

LC/MS (System A): m/z (ESI$^+$)=R$_t$=1.15 min, m/z=599 [M$^+$], UV purity=90%.

Intermediate 65—Synthesis of 2-[(6-bromo-1-ethyl-1H-1,3-benzodiazol-2-yl)methyl]-2,3-dihydro-1H-isoindole-1,3-dione

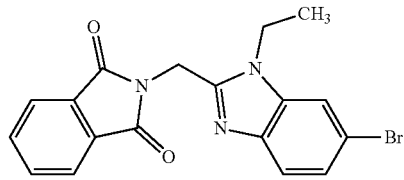 [SMILES: CCn1c(CN2C(=O)c3ccccc3C2=O)nc2ccc(Br)cc21]

A mixture of N-phthaloylglycine (13.1 g, 63.8 mmol), TBTU (21.5 g, 67.0 mmol) and triethylamine (14.1 ml, 79.1 mmol) in DMF (150 ml) was stirred at RT for 45 min. A solution of 5-bromo-1-N-ethylbenzene-1,2-diamine (13.1 g, 60.9 mmol) in THF (50 ml) was added and the resulting mixture was stirred at RT for 18 h. The reaction mixture was added onto saturated aqueous $NaHCO_3$ solution (400 ml). The resulting precipitate was collected by filtration then washed with water and dried under vacuum to afford the intermediate as a light grey solid. The solid thus obtained was added portionwise to acetic acid (150 ml). The resulting suspension was heated at 100° C. for 2.5 h then allowed to cool to RT. The reaction mixture was concentrated in vacuo then the residue was partitioned between EtOAc (300 ml) and water (300 ml). The resulting precipitate was collected by filtration and washed with EtOAc (200 ml) and water (200 ml) then dried under vacuum to afford the product as a pink solid (17.9 g, 76%).

$^1$H NMR (500 MHz, DMSO-$d_6$) δ 7.96 (dd, J=5.6, 3.0 Hz, 2H), 7.93-7.88 (m, 3H), 7.44 (d, J=8.5 Hz, 1H), 7.27 (dd, J=8.5, 1.9 Hz, 1H), 5.12 (s, 2H), 4.39 (q, J=7.2 Hz, 2H), 1.37 (t, J=7.2 Hz, 3H).

LC/MS (System A): m/z (ESI⁺)=384 [M(⁷⁹Br)H⁺], 386 [M(⁸¹Br)H⁺], $R_t$=1.12 min, UV purity=100%.

Intermediate 66—Synthesis of tert-butyl N-(3-{2-[(1,3-dioxo-2,3-dihydro-1H-isoindol-2-yl)methyl]-1-ethyl-1H-1,3-benzodiazol-6-yl}prop-2-yn-1-yl)carbamate

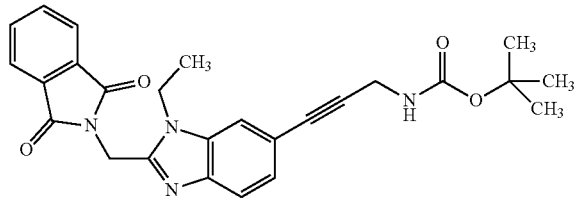 [SMILES: CCn1c(CN2C(=O)c3ccccc3C2=O)nc2ccc(C#CCNC(=O)OC(C)(C)C)cc21]

CuI (0.25 g, 1.29 mmol) was added to a solution of 2-[(6-bromo-1-ethyl-1H-1,3-benzodiazol-2-yl)methyl]-2,3-dihydro-1H-isoindole-1,3-dione, Intermediate 65 (5.00 g, 13.0 mmol) and tert-butyl N-(prop-2-yn-1-yl)carbamate (2.40 g, 15.5 mmol) in DMF (60 ml). Nitrogen was bubbled through the reaction mixture for 5 min then Pd(PPh₃)₄ (0.74 g, 0.64 mmol) was added, followed by triethylamine (2.92 ml, 19.3 mmol). The reaction mixture was heated at 65° C. for 24 h then concentrated in vacuo. The crude material was purified by flash column chromatography on a silica column (100 g). The column was eluted with EtOAc:heptane, increasing the gradient linearly from 0:100 to 50:50 over 10 column volumes. The desired fractions were combined and evaporated to afford the product as a yellow foam (2.45 g, 39%).

¹H NMR (250 MHz, DMSO-d₆) δ 7.99-7.88 (m, 4H), 7.71 (s, 1H), 7.46 (d, J=8.3 Hz, 1H), 7.35 (s, 1H), 7.16 (dd, J=8.3, 1.3 Hz, 1H), 5.13 (s, 2H), 4.40 (q, J=7.1 Hz, 2H), 4.02-3.97 (m, 2H), 1.41 (s, 9H), 1.36 (t, J=7.1 Hz, 3H).

LC/MS (System A): m/z (ESI⁺)=459 [MH⁺], $R_t$=1.17 min, UV purity=95%.

Intermediate 67—Synthesis of tert-butyl N-(3-{2-[(1,3-dioxo-2,3-dihydro-1H-isoindol-2-yl)methyl]-1-ethyl-1H-1,3-benzodiazol-6-yl}propyl)carbamate

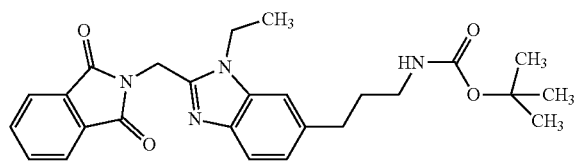 [SMILES: CCn1c(CN2C(=O)c3ccccc3C2=O)nc2ccc(CCCNC(=O)OC(C)(C)C)cc21]

Palladium on carbon (10 wt %, 557 mg) was added to a solution of tert-butyl N-(3-{2-[(1,3-dioxo-2,3-dihydro-1H-isoindol-2-yl)methyl]-1-ethyl-1H-1,3-benzodiazol-6-yl}prop-2-yn-1-yl)carbamate, Intermediate 66 (2.4 g, 5.23 mmol) in EtOH (120 ml). The reaction mixture was stirred at RT under a hydrogen atmosphere for 48 h. The reaction was recharged with palladium on carbon (10 wt %, 278 mg) and stirred at RT under a hydrogen atmosphere for a further 24 h. The reaction was re-charged with palladium on carbon (10 wt %, 278 mg) and stirred at RT under a hydrogen atmosphere for a further 24 h. The reaction mixture was filtered through a Celite pad. The Celite pad was rinsed with EtOH (100 ml), MeOH (100 ml), EtOAc (100 ml), and DMF (5 ml). The combined filtrate was concentrated in vacuo then the crude material was purified by flash column chromatography on a silica column (25 g). The column was eluted with EtOAc:heptane, increasing the gradient linearly from 0:100 to 75:25 over 10 column volumes. The desired fractions were combined and evaporated to afford the product as a light yellow solid (1.20 g, 43%).

¹H NMR (500 MHz, DMSO-d₆) δ 7.98-7.93 (m, 2H), 7.92-7.88 (m, 2H), 7.37-7.34 (m, 2H), 6.97 (dd, J=8.2, 1.5 Hz, 1H), 6.84 (t, J=5.3 Hz, 1H), 5.09 (s, 2H), 4.35 (q, J=7.2 Hz, 2H), 2.96-2.90 (m, 2H), 2.69-2.63 (m, 2H), 1.71 (p, J=7.3 Hz, 2H), 1.40-1.35 (m, 12H).

LC/MS (System A): m/z (ESI⁺)=463 [MH⁺], $R_t$=1.07 min, UV purity=86%.

Intermediate 68—Synthesis of 6-(3-{[(tert-butoxy)carbonyl]amino}propyl)-2-[(1,3-dioxo-2,3-dihydro-1H-isoindol-2-yl)methyl]-1,3-diethyl-1H-1,3-benzodiazol-3-ium iodide

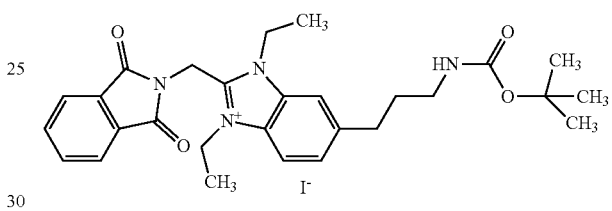

Iodoethane (1.04 ml, 13.0 mmol) was added to a solution of tert-butyl N-(3-{2-[(1,3-dioxo-2,3-dihydro-1H-isoindol-2-yl)methyl]-1-ethyl-1H-1,3-benzodiazol-6-yl}propyl)carbamate, Intermediate 67 (86%, 1.20 g, 2.23 mmol) in MeCN (18 ml) in a pressure tube. The tube was sealed and heated at 110° C. for 4 h. The reaction was allowed to cool to RT then iodoethane (1.04 ml, 13.0 mmol) was added then the reaction was heated at 110° C. for a further 4 h. The reaction mixture was allowed to cool to RT then concentrated in vacuo to afford the product as a brown solid (1.52 g, >99%).

¹H NMR (500 MHz, DMSO-d₆) δ 8.02 (d, J=8.6 Hz, 1H), 7.97-7.93 (m, 3H), 7.92-7.88 (m, 2H), 7.58 (d, J=8.6 Hz, 1H), 6.89 (s, 1H), 5.42 (s, 2H), 4.70-4.66 (m, 4H), 2.93 (q, J=6.2 Hz, 2H), 2.79 (t, J=7.4 Hz, 2H), 1.81-1.72 (m, 2H), 1.44-1.40 (m, 6H), 1.37 (s, 9H).

LC/MS (System A): m/z (ESI⁺)=491 [M⁺], $R_t$=1.08 min, UV purity=91%.

Intermediate 69—Synthesis of 2-(aminomethyl)-6-(3-{[(tert-butoxy)carbonyl]amino}propyl)-1,3-diethyl-1H-1,3-benzodiazol-3-ium iodide

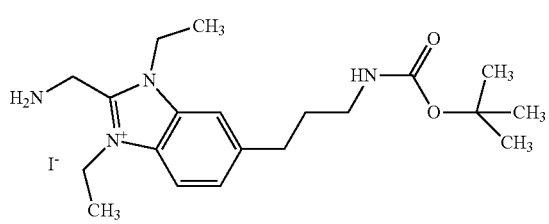 [SMILES: CCn1c(CN)[n+](CC)c2ccc(CCCNC(=O)OC(C)(C)C)cc21 ; [I-]]

Hydrazine hydrate (609 μl, 12.5 mmol) was added to a solution of 6-(3-{[(tert-butoxy)carbonyl]amino}propyl)-2-[(1,3-dioxo-2,3-dihydro-1H-isoindol-2-yl)methyl]-1,3-diethyl-1H-1,3-benzodiazol-3-ium iodide, Intermediate 68 (91%, 1.52 g, 2.23 mmol) in MeOH (20 ml) in a pressure tube. The tube was sealed then heated at 75° C. for 3 h. The reaction mixture was allowed to cool to RT then concentrated in vacuo. The residue was suspended in CH$_2$Cl$_2$: MeOH (9:1, 20 ml) then filtered. The filtrate was concentrated in vacuo to afford the product as a yellow foam (1.21 g, 89%).

$^1$H NMR (500 MHz, DMSO-d$_6$) δ 7.95 (d, J=8.5 Hz, 1H), 7.88 (s, 1H), 7.51 (dd, J=8.5, 1.3 Hz, 1H), 6.91 (t, J=5.5 Hz, 1H), 4.60-4.52 (m, 4H), 4.26 (s, 2H), 2.93 (app. q, J=6.6 Hz, 2H), 2.78 (t, J=7.5 Hz, 2H), 1.80-1.70 (m, 2H), 1.46-1.40 (m, 6H), 1.37 (s, 9H).

LC/MS (System A): m/z (ESI$^+$)=361 [M$^+$], R$_t$=0.81 min, UV purity=80%.

Intermediate 69 may be reacted with a compound of general formula (IV) to give a compound of formula:

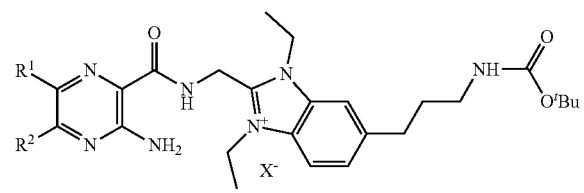

This compound may be treated with HCl solution in dioxane to remove the protecting group, yielding a compound of the formula:

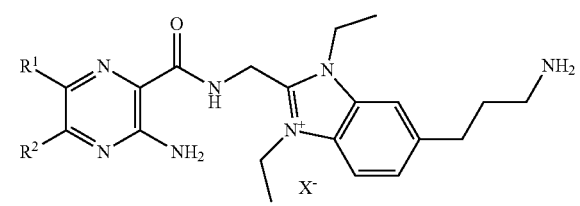

This compound may then be stirred at room temperature with 4,6-O-benzylidene-D-glucopyranose and acetic acid in methanol, followed by the addition of NaCNBH$_3$. After further stirring, a benzylidene protected intermediate will be obtained. This can then be treated with aqueous HCl to give a product of formula:

An analogous process is described in our co-pending application WO 2018/096325 (see Example 45).

Intermediate 86—Synthesis of 5-(2-aminoethoxy)-1,3-diethyl-2-[({[(9H-fluoren-9-yl)methoxy]carbonyl}amino)methyl]-1H-1,3-benzodiazol-3-ium hydrochloride chloride

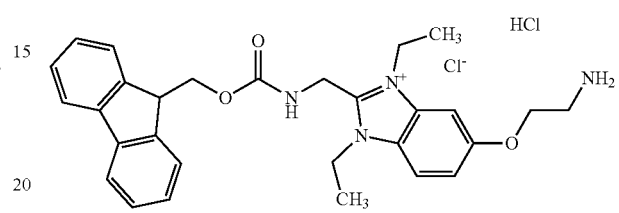

HCl solution in dioxane (4.0 M, 14 ml, 56 mmol) was added to a mixture of 6-(2-{[(tert-butoxy)carbonyl]amino}ethoxy)-1,3-diethyl-2-({[(9H-fluoren-9-ylmethoxy)carbonyl]amino}methyl)-1H-1,3-benzodiazol-3-ium iodide, Intermediate 58 (4.28 g, 6.01 mmol) in MeCN (50 ml). The resulting mixture was stirred at RT for 20 min then concentrated in vacuo to afford the product as a brown/orange foam (3.87 g, 98%).

$^1$H NMR (500 MHz, DMSO-d$_6$) δ 8.30 (t, J=5.3 Hz, 1H), 8.15 (s (br), 3H), 7.99 (d, J=9.1 Hz, 1H), 7.86 (d, J=7.5 Hz, 2H), 7.69-7.60 (m, 3H), 7.38-7.30 (m, 3H), 7.25 (t, J=7.3 Hz, 2H), 4.75 (d, J=5.2 Hz, 2H), 4.58-4.45 (m, 6H), 4.34 (t, J=4.9 Hz, 2H), 4.22 (t, J=6.0 Hz, 1H), 1.37-1.30 (m, 6H).

LC/MS (System A): m/z (ESI$^+$)=485 [M$^+$], R$_t$=0.84 min, UV purity=85%.

Intermediate 87—Synthesis of 5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-2-[({[(9H-fluoren-9-yl)methoxy]carbonyl}amino)methyl]-1H-1,3-benzodiazol-3-ium chloride

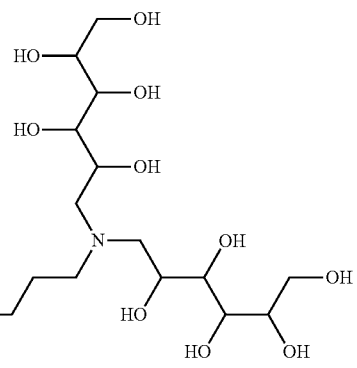
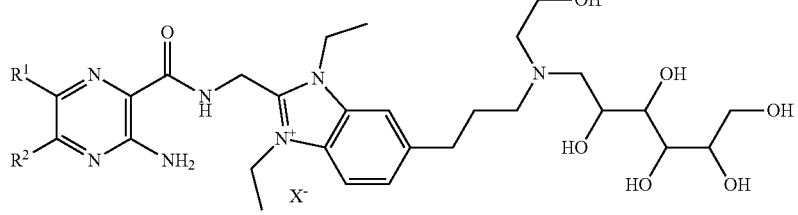

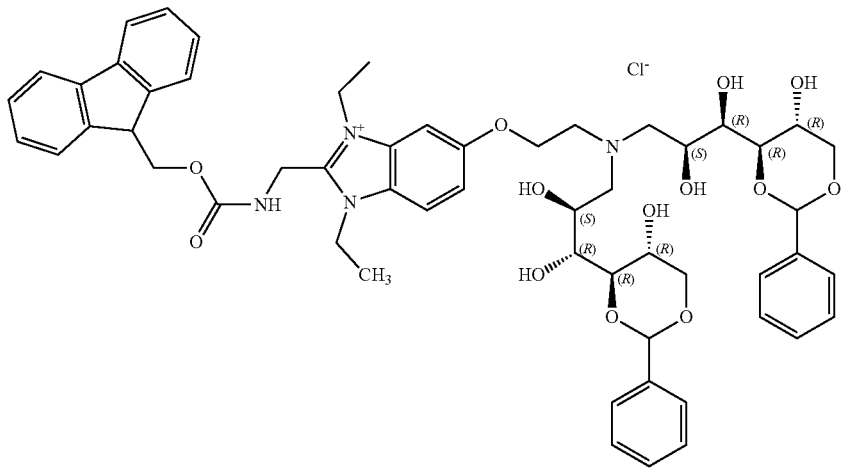

A mixture of 4,6-O-benzylidene-D-glucopyranose (95%, 6.67 g, 23.6 mmol), 5-(2-aminoethoxy)-1,3-diethyl-2-[({[(9H-fluoren-9-yl)methoxy]carbonyl}amino)methyl]-1H-1,3-benzodiazol-3-ium hydrochloride chloride, Intermediate 86 (85%, 3.87 g, 5.91 mmol) and AcOH (1.35 ml, 23.6 mmol) in MeOH (100 ml) was stirred at RT for 0.5 h. NaCNBH$_3$ (1.48 g, 23.6 mmol) was added then the resulting mixture was stirred at RT for 20 h. More MeOH (40 ml) was added then the reaction was left to stir at RT for a further 24 h. More MeOH (80 ml) was added, then the reaction was retreated with 4,6-O-benzylidene-D-glucopyranose (95%, 1.60 g, 5.67 mmol), AcOH (0.34 ml, 5.94 mmol) and NaCNBH$_3$ (0.38 g, 6.05 mmol). The reaction was left to stir at RT for a further 92 h then added to saturated aqueous NaHCO$_3$ solution (250 ml). The resultant suspension was stirred at RT for 20 min. The solid was collected by filtration then washed with water and dried under vacuum to afford the product as a pale pink solid (6.43 g, 89%).

$^1$H NMR (500 MHz, CD$_3$OD) δ 7.76 (d, J=8.5 Hz, 3H), 7.59 (d, J=8.0 Hz, 2H), 7.53-7.49 (m, 2H), 7.47-7.43 (m, 4H), 7.37-7.34 (m, 3H), 7.33-7.25 (m, 10H), 7.24-7.20 (m, 2H), 5.50 (s, 2H), 4.63-4.48 (m, 7H), 4.30-4.16 (m, 6H), 4.08-4.03 (m, 2H), 3.99-3.93 (m, 5H), 3.91-3.86 (m, 1H), 3.78-3.73 (m, 3H), 3.67-3.56 (m, 4H), 3.16-3.06 (m, 2H), 3.00-2.93 (m, 2H), 2.85-2.77 (m, 2H), 1.49-1.37 (m, 6H).

LC/MS (System A): m/z (ESI$^+$)=990 [M$^+$], 496 [(M$^+$)+H$^+$], R$_t$=0.93 min, UV purity=84%.

Intermediate 88—2-(aminomethyl)-5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-1H-1,3-benzodiazol-3-ium chloride

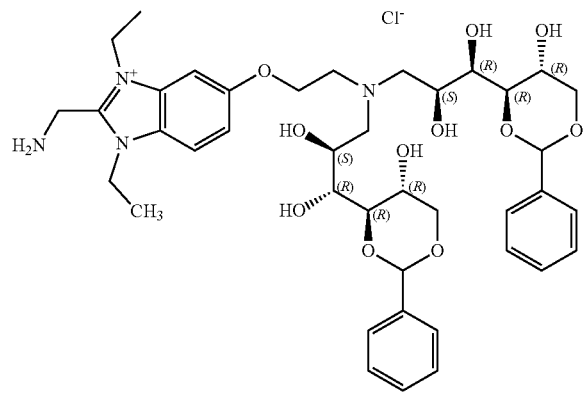

Morpholine (4.77 ml, 55.1 mmol) was added to a stirred mixture of 5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-2-[({[(9H-fluoren-9-yl)methoxy]carbonyl}amino)methyl]-1H-1,3-benzodiazol-3-ium chloride, Intermediate 87 (84% 6.42 g, 5.26 mmol) in THF (60 ml). The resulting mixture was stirred at RT for 4 h. The reaction mixture was diluted with diethyl ether (150 ml).

The resulting suspension was agitated then the suspension was decanted off, leaving behind a viscous oil. More diethyl ether (80 ml) was added to the oil residue then the mixture was sonicated. The resulting suspension was again decanted off to leave behind a viscous oil. The process was repeated once more with diethyl ether (80 ml) then the resulting viscous oil was dried under vacuum to afford the product as a pale purple foam (4.39 g, 85%).

$^1$H NMR (500 MHz, CD$_3$OD) δ 7.81-7.66 (m, 1H), 7.51-7.14 (m, 14H), 5.52-5.43 (m, 2H), 4.65-4.48 (m, 5H), 4.35-4.30 (m, 2H), 4.27-4.11 (m, 4H), 4.08-3.85 (m, 7H), 3.81-3.72 (m, 4H), 3.68-3.63 (m, 6H), 3.63-3.53 (m, 3H), 3.16-3.01 (m, 2H), 2.98-2.90 (m, 1H), 2.84-2.80 (m, 6H), 1.57-1.45 (m, 6H).

LC/MS (System A): m/z (ESI$^+$)=767 [M$^+$], R$_t$=0.75 min, UV purity=82%.

Intermediate 89—Synthesis of 2-(aminomethyl)-5-(2-{bis[(2S,3R,4R,5R)-2,3,4,5,6-pentahydroxyhexyl]amino}ethoxy)-1,3-diethyl-1H-1,3-benzodiazol-3-ium dihydrochloride chloride

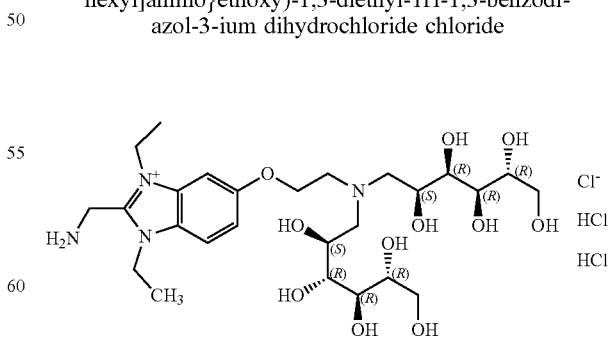

A mixture of 2-(aminomethyl)-5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-1H-1,3-benzodiazol-3-ium chloride, Intermediate 88 (82%, 1.50 g, 1.53 mmol) and aqueous HCl solution (2.0 M, 25 ml, 50 mmol) was stirred at RT for 1 h. The reaction mixture was concentrated in vacuo then the residue was dissolved in water (10 ml) and lyophilised to afford the product as a pale purple foam (1.53 g, >99%).

$^1$H NMR (500 MHz, CD$_3$OD) δ 8.01 (d, J=9.2 Hz, 1H), 7.73 (d, J=2.2 Hz, 1H), 7.55-7.51 (m, 1H), 4.93 (s, 2H), 4.79-4.69 (m, 4H), 4.68-4.62 (m, 3H), 4.32-4.19 (m, 2H), 4.07-3.94 (m, 2H), 3.92-3.84 (m, 10H), 3.81-3.58 (m, 16H), 3.33-3.29 (m, 8H), 3.26-3.21 (m, 6H), 1.65-1.59 (m, 6H).

LC/MS (System A): m/z (ESI$^+$)=591 [M$^+$], R$_t$=0.13 min, UV purity=70%.

Intermediate 89 may be reacted with a compound of general formula (IV) to give a compound of general formula (I). An analogous process is described in our co-pending application WO 2018/096325 (see Example 43).

Intermediate 90—Synthesis of 5-(3-aminopropoxy)-1,3-diethyl-2-[({[(9H-fluoren-9-yl)methoxy] carbonyl}amino)methyl]-1H-1,3-benzodiazol-3-ium hydrochloride chloride

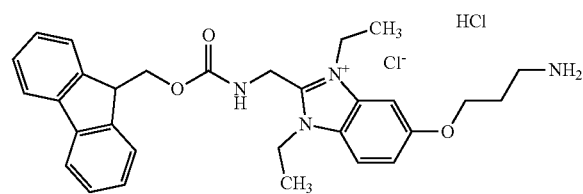 [SMILES: Cl ; CCn1c(CNC(=O)OCC2c3ccccc3-c3ccccc32)[n+](CC)c2cc(OCCCN)ccc21 ; [Cl-]]

HCl solution in dioxane (4.0 M, 3.3 ml, 13 mmol) was added to a mixture of 6-(3-{[(tert-butoxy)carbonyl] amino}propoxy)-1,3-diethyl-2-({[(9H-fluoren-9-yl-methoxy)carbonyl]amino}methyl)-1H-1,3-benzodiazol-3-ium iodide, Intermediate 63 (95%, 1.00 g, 1.31 mmol) in MeCN (15 ml). The reaction mixture was stirred at RT for 0.5 h then concentrated in vacuo to afford the product as a viscous yellow oil (875 mg, >99%—yield corrected for 15 wt % residual dioxane observed in NMR).

$^1$H NMR (500 MHz, DMSO-d$_6$) δ 8.30 (t, J=5.3 Hz, 1H), 8.00-7.85 (m, 6H), 7.65-7.59 (m, 3H), 7.37 (t, J=7.4 Hz, 2H), 7.31 (dd, J=9.1, 2.1 Hz, 1H), 7.27 (t, J=7.4 Hz, 2H), 4.76 (d, J=5.4 Hz, 2H), 4.58-4.46 (m, 6H), 4.27-4.19 (m, 3H), 3.05-2.95 (m, 2H), 2.12-2.06 (m, 2H), 1.34 (t, J=7.1 Hz, 6H).

LC/MS (System A): m/z (ESI$^+$)=499 [M$^+$], R$_t$=0.89 min, UV purity=98%.

Intermediate 91—Synthesis of 5-(3-{bis[(2S,3R)-2, 3-dihydroxy-3-[(4R,5R)-5-hydroxy-2-phenyl-1,3-dioxan-4-yl]propyl]amino}propoxy)-1,3-diethyl-2-[({[(9H-fluoren-9-yl)methoxy]carbonyl}amino) methyl]-1H-1,3-benzodiazol-3-ium hydrochloride chloride

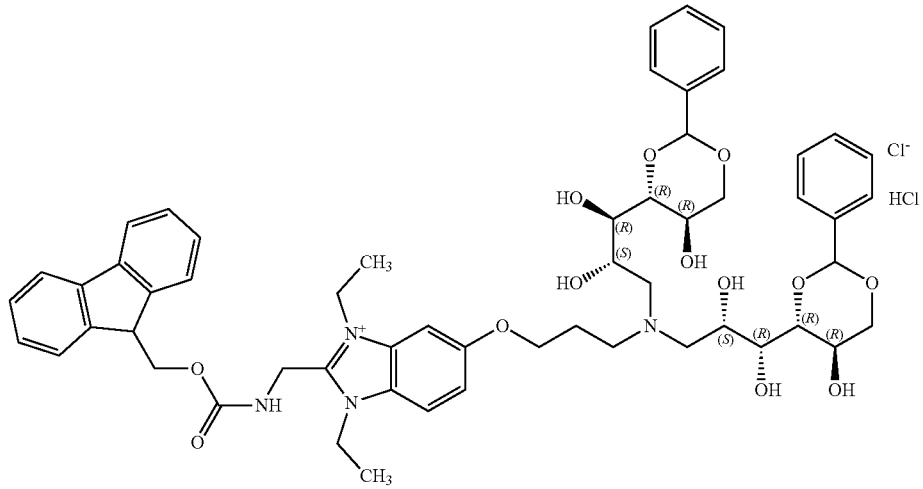

A mixture of 4,6-O-benzylidene-D-glucopyranose (1.43 g, 5.32 mmol), 5-(3-aminopropoxy)-1,3-diethyl-2-[({[(9H-fluoren-9-yl)methoxy]carbonyl}amino)methyl]-1H-1,3-benzodiazol-3-ium hydrochloride chloride, Intermediate 90 (85%, 875 mg, 1.30 mmol) and AcOH (305 µl, 5.32 mmol) in MeOH (25 ml) was stirred at RT for 0.5 h. NaCNBH$_3$ (334 mg, 5.32 mmol) was added then the resulting mixture was stirred at RT for 64 h. Additional 4,6-O-benzylidene-D-glucopyranose (500 mg, 1.86 mmol) and AcOH (110 µl, 1.92 mmol) was added. The mixture was stirred for 0.5 h then NaCNBH$_3$ (115 mg, 1.83 mmol) was added. The resulting mixture was stirred at RT for a further 16 h. Saturated aqueous NaHCO$_3$ solution (40 ml) was added over 5 min whereupon a white precipitate formed. The resultant suspension was filtered and the collected solid was washed with water then dried under vacuum to afford the product as a white solid (1.39 g, 60%).

$^1$H NMR (500 MHz, DMSO-d$_6$) δ 8.24 (s, 1H), 7.88-7.80 (m, 3H), 7.64-7.57 (m, 3H), 7.48-7.19 (m, 26H), 5.46 (dd, J=15.4, 7.6 Hz, 2H), 4.73 (s, 2H), 4.48 (s, 9H), 4.21 (d, J=5.4 Hz, 3H), 4.10 (s, 5H), 3.82-3.67 (m, 4H), 1.91 (s, 2H), 1.32 (s, 6H).

LC/MS (System A): m/z (ESI$^+$)=503 [(M$^+$)+H$^+$], R$_t$=1.00 min, UV purity=60%.

Intermediate 92—Synthesis of 2-(aminomethyl)-5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-1H-1,3-benzodiazol-3-ium hydrochloride chloride

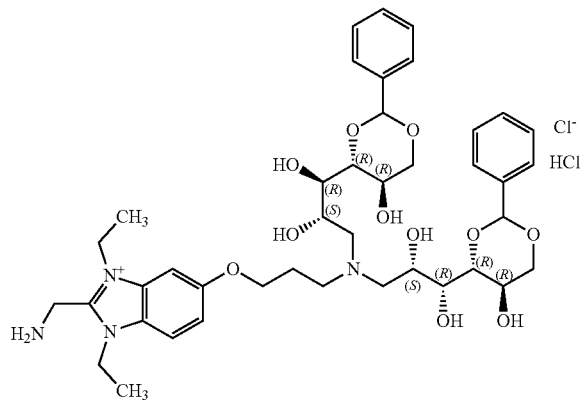

Morpholine (659 μl, 7.62 mmol) was added to a mixture of 5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-2-[({[(9H-fluoren-9-yl)methoxy]carbonyl}amino)methyl]-1H-1,3-benzodiazol-3-ium hydrochloride chloride, Intermediate 91 (60%, 1.32 g, 0.762 mmol) in THF (10 ml). The mixture was stirred at RT for 2.5 h. The reaction mixture was diluted with diethyl ether (20 ml). The resulting suspension was sonicated then the suspension was decanted off, leaving behind a viscous oil. More diethyl ether (20 ml) was added to the oil residue then the mixture was sonicated. The resulting suspension was again decanted off to leave behind a viscous oil. The process was repeated once more with diethyl ether (20 ml) then the resulting viscous oil was dried under vacuum to afford the product as a pale orange solid (639 mg, 79%).

$^1$H NMR (500 MHz, CD$_3$OD) δ 7.83-7.77 (m, 1H), 7.54-7.44 (m, 5H), 7.39-7.21 (m, 10H), 5.54-5.44 (m, 2H), 4.68-4.55 (m, 6H), 4.40-4.32 (m, 2H), 4.31-4.07 (m, 6H), 4.04-3.87 (m, 6H), 3.79-3.74 (m, 2H), 3.61-3.55 (m, 2H), 2.83-2.76 (m, 2H), 2.74-2.65 (m, 2H), 2.03-1.96 (m, 1H), 1.60-1.52 (m, 6H).

LC/MS (System A): m/z (ESI$^+$)=781 [M$^+$], 391 [(M$^+$)+H$^+$], R$_t$=0.78 min, UV purity=80%.

Intermediate 93—Synthesis of 2-(aminomethyl)-5-(3-{bis[(2S,3R,4R,5R)-2,3,4,5,6-pentahydroxyhexyl]amino}propoxy)-1,3-diethyl-1H-1,3-benzodiazol-3-ium hydrochloride chloride

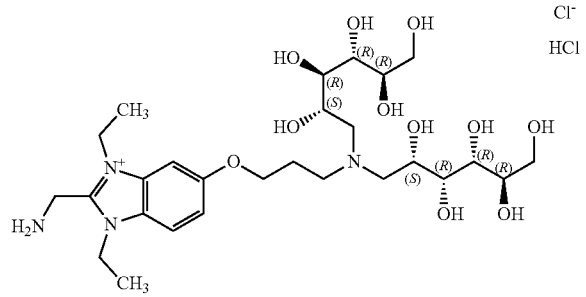

A mixture of 2-(aminomethyl)-5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-1H-1,3-benzodiazol-3-ium hydrochloride chloride, Intermediate 92 (80%, 375 mg, 0.367 mmol) and aqueous HCl solution (2.0 M, 8.0 ml, 16 mmol) was stirred at RT for 40 min. The reaction mixture was concentrated in vacuo then diluted with water and lyophilised (note to afford the product as a pale orange solid (305 mg, 98%).

$^1$H NMR (500 MHz, CD$_3$OD) δ 7.98 (d, J=9.2 Hz, 1H), 7.62 (d, J=2.1 Hz, 1H), 7.49 (dd, J=9.2, 2.2 Hz, 1H), 4.92 (s, 2H), 4.76-4.69 (m, 4H), 4.37 (t, J=5.7 Hz, 2H), 4.25 (dd, J=9.0, 4.1 Hz, 2H), 3.89-3.82 (m, 7H), 3.80-3.73 (m, 4H), 3.72-3.53 (m, 13H), 3.50-3.43 (m, 2H), 3.24-3.21 (m, 4H), 2.49-2.33 (m, 2H), 1.61 (t, J=7.3 Hz, 6H).

LC/MS (System A): m/z (ESI$^+$)=605 [M$^+$], 303 [(M$^+$)+H$^+$], R$_t$=0.13 min, UV purity=80%.

Intermediate 93 may be reacted with a compound of general formula (IV) to give a compound of general formula (I). An analogous process is described in our co-pending application WO 2018/096325 (see Example 44).

Intermediate 100—Synthesis of tert-butyl N-[3-({[(9H-fluoren-9-yl)methoxy]carbonyl}amino)propyl]carbamate

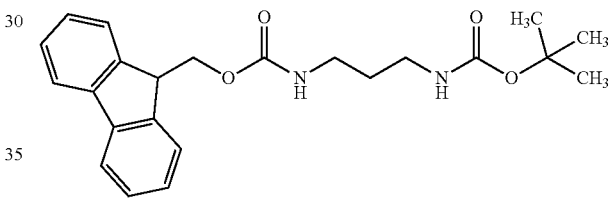

A solution of 2,5-dioxopyrrolidin-1-yl 9H-fluoren-9-ylmethyl carbonate (3.87 g, 11.5 mmol) in MeCN (30 ml) was added dropwise over 20 min to a mixture of NaHCO$_3$ (1.93 g, 23.0 mmol) and tert-butyl N-(3-aminopropyl)carbamate (2.00 g, 11.5 mmol) in MeCN (40 ml) and water (40 ml). The resultant mixture was stirred at RT for 1 h then filtered. The collected solid was washed with water (2×20 ml) then MeCN (2×20 ml), then dried under vacuum to afford a white solid (1.28 g). The solid thus obtained was suspended in EtOAc (10 ml) then filtered. The solid collected was dried under vacuum to afford a first batch of the product as a white solid (1.24 g). The MeCN/water filtrate was concentrated in vacuo then the resulting residue was partitioned between EtOAc (100 ml) and water (50 ml). The phases were separated then the organic phase was washed with water (2×50 ml), brine (20 ml), then dried over Na$_2$SO$_4$, filtered and concentrated in vacuo to afford a white solid (2.30 g). The solid thus obtained was combined with the filtrate from the EtOAc trituration then the combined material was purified by flash column chromatography on a silica column (25 g). The column was eluted with heptane:EtOAc:MeOH using the following gradient: 100:0:0, 3 CV; 100:0:0-81:19:0, 3 CV; 81:19:0%, 2 CV; 81:19:0-61:39:0, 3 CV; 61:39:0, 5 CV; 61:39:0-12:88:0, 8 CV; 12:88:0-0:100:0, 2 CV; 0:100:0, 1 CV; 0:100:0-0:93:7, 4 CV; 0:93:7, 3 CV; 0:93:7-0:91:9, 1 CV. The desired fractions were combined and evaporated to afford a second batch of the product as a white solid (2.60 g), which was analytically identical to the first batch. Overall yield=3.84 g (84%).

¹H NMR (500 MHz, DMSO-d₆) δ 7.89 (d, J=7.5 Hz, 2H), 7.73-7.59 (m, 2H), 7.41 (t, J=7.4 Hz, 2H), 7.36-7.29 (m, 2H), 7.22 (t, J=5.6 Hz, 1H), 6.74 (s, 1H), 4.29 (d, J=6.9 Hz, 2H), 4.21 (t, J=6.8 Hz, 1H), 3.04-2.78 (m, 4H), 1.56-1.43 (m, 2H), 1.37 (s, 9H).

LC/MS (System A): m/z (ESI⁺)=419 [(M⁺Na⁺)⁺], R$_t$=1.25 min, UV purity=99%.

Intermediate 101—Synthesis of (9H-fluoren-9-yl)methyl N-(3-aminopropyl)carbamate hydrochloride

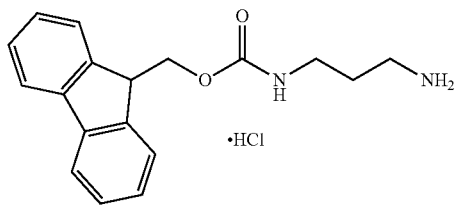 [SMILES: NCCCNC(=O)OCC1c2ccccc2-c2ccccc21 ; Cl]

HCl solution in dioxane (4.0 M, 8.0 ml, 32 mmol) was added to a suspension of tert-butyl N-[3-({[(9H-fluoren-9-yl)methoxy]carbonyl}amino)propyl]carbamate, Intermediate 100 (2.60 g, 6.56 mmol) in MeCN (40 ml). The reaction mixture was stirred at RT for 1 h then filtered. The collected solid was rinsed with MeCN then dried under vacuum to afford the product as a white solid (1.89 g, 87%).

¹H NMR (500 MHz, DMSO-d₆) δ 7.95-7.77 (m, 5H), 7.68 (d, J=7.4 Hz, 2H), 7.48-7.38 (m, 3H), 7.37-7.29 (m, 2H), 4.33 (d, J=6.8 Hz, 2H), 4.26-4.17 (m, 1H), 3.10-2.99 (m, 2H), 2.81-2.71 (m, 2H), 1.76-1.64 (m, 2H).

LC/MS (System A): m/z (ESI⁺)=297 [MH⁺], R$_t$=0.91 min, UV purity=100%.

Intermediate 102—Synthesis of (9H-fluoren-9-yl) methyl N-(3-{bis[(2S,3R)-2,3-dihydroxy-3-[(4R,5R)-5-hydroxy-2-phenyl-1,3-dioxan-4-yl]propyl]amino}propyl)carbamate; bis(formic acid)

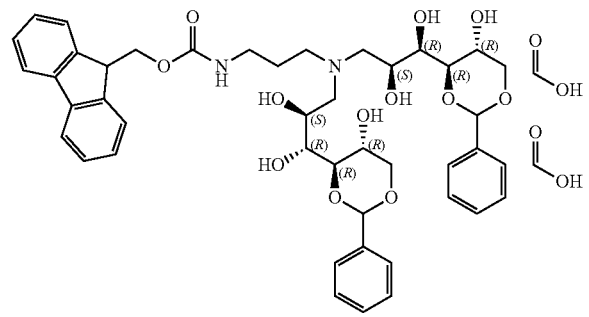

A mixture of (9H-fluoren-9-yl)methyl N-(3-aminopropyl) carbamate hydrochloride, Intermediate 101 (900 mg, 2.70 mmol) and 4,6-O-benzylidene-D-glucopyranose (1.45 g, 5.41 mmol) in MeOH (40 ml) was stirred at RT for 1.5 h. AcOH (0.31 ml, 5.4 mmol) and NaCNBH₃ (340 mg, 5.41 mmol) were added then the reaction was stirred at RT for 18 h. The reaction was recharged with 4,6-O-benzylidene-D-glucopyranose (1.45 g, 5.41 mmol) then the reaction was stirred at RT for 1 h. NaCNBH₃ (340 mg, 5.41 mmol) was added then the reaction was left to stir at RT for a further 114 h. Saturated aqueous NaHCO₃ solution (50 ml) was added dropwise over 10 min then the resultant mixture was partitioned between EtOAc (50 ml) and water (50 ml). The phases were separated then the organic phase was washed with saturated aqueous NaHCO₃ solution (2×50 ml), water (50 ml) and brine (20 ml), then dried using NaSO₄, filtered and concentrated in vacuo dryness to afford a white solid (2.25 g). The crude material thus obtained was purified by flash column chromatography on C18 (120 g). The column was eluted with MeCN:water+0.1% formic acid using the following gradient (% MeCN, column volumes): 10%, 2 CV; 10-29%, 4 CV; 29-39%, 2 CV; 39%, 2 CV; 39-47%, 1 CV; 47-73%, 1 CV; 73-100%, 1 CV; 100% 1 CV. The desired fractions were combined and concentrated in vacuo to afford the product as a white solid (1.12 g, 46%).

¹H NMR (500 MHz, DMSO-d₆) δ 7.88 (d, J=7.5 Hz, 2H), 7.67 (d, J=7.4 Hz, 2H), 7.45-7.37 (m, 6H), 7.36-7.25 (m, 8H), 7.24-7.16 (m, 1H), 5.49-5.39 (m, 2tH), 5.27-5.01 (m, 2H), 4.32-4.25 (m, 2H), 4.23-4.16 (m, 1H), 4.16-4.09 (m, 2H), 3.84-3.74 (m, 4H), 3.73-3.66 (m, 2H), 3.64-3.56 (partially obscured m, 2H), 3.53-3.45 (obscured m, 2H), 2.99-2.89 (obscured m, 2H), 2.68-2.54 (obscured m, 6H), 1.60-1.48 (m, 2H).

LC/MS (System A): m/z (ESI⁺)=801 [MH⁺], R$_t$=1.01 min, UV purity=100%.

Intermediate 103—Synthesis of (1R,2S)-3-[(3-aminopropyl)[(2S,3R)-2,3-dihydroxy-3-[(4R,5R)-5-hydroxy-2-phenyl-1,3-dioxan-4-yl]propyl]amino]-1-[(4R,5R)-5-hydroxy-2-phenyl-1,3-dioxan-4-yl] propane-1,2-diol; bis(formic acid)

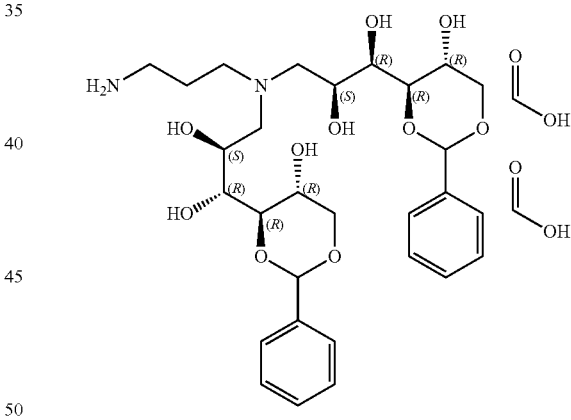

Diethylamine (1.44 ml, 14.0 mmol) was added to a solution of (9H-fluoren-9-yl)methyl N-(3-{bis[(2S,3R)-2,3-dihydroxy-3-[(4R,5R)-5-hydroxy-2-phenyl-1,3-dioxan-4-yl]propyl]amino}propyl)carbamate; bis(formic acid), Intermediate 102 (1.12 g, 1.40 mmol) in THF (20 ml). The reaction mixture was stirred at RT for 16 h then concentrated in vacuo. The crude material thus obtained was purified by flash column chromatography on C18 (60 g). The column was eluted with MeCN:water+0.1% formic acid using the following gradient (% MeCN, column volumes): 5%, 2 CV; 5-18%, 3 CV; 18%, 2 CV; 18-26%, 2 CV; 26-100%, 2 CV; 100% 1 CV. The desired fractions were combined and concentrated in vacuo to afford the product as a white solid (710 mg, 76%).

¹H NMR (500 MHz, DMSO-d₆) δ 8.36-8.24 (m, 2H), 7.44-7.38 (m, 4H), 7.38-7.29 (m, 6H), 5.44 (s, 2H), 4.18-

4.08 (obscured m, 2H), 3.87-3.75 (obscured m, 4H), 3.73-3.65 (obscured m, 2H), 3.63-3.56 (obscured m, 2H), 3.53-3.44 (obscured m, 2H), 2.90-2.78 (m, 2H), 2.75-2.55 (obscured m, 6H), 1.78-1.65 (m, 1H), 1.55 (m, 1H).

LC/MS (System A): m/z (ESI+)=579 [MH+], $R_t$=0.74 min, UV purity=100%.

Intermediate 104—Synthesis of (2R,3R,4R,5S)-6-[(3-aminopropyl)[(2S,3R,4R,5R)-2,3,4,5,6-pentahydroxyhexyl]amino]hexane-1,2,3,4,5-pentol dihydrochloride

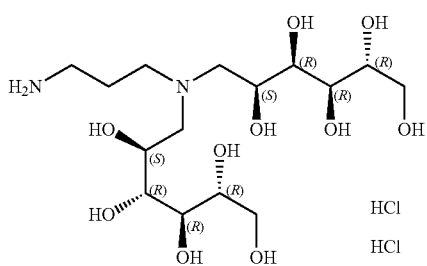

A mixture of (1R,2S)-3-[(3-aminopropyl)[(2S,3R)-2,3-dihydroxy-3-[(4R,5R)-5-hydroxy-2-phenyl-1,3-dioxan-4-yl]propyl]amino]-1-[(4R,5R)-5-hydroxy-2-phenyl-1,3-dioxan-4-yl]propane-1,2-diol; bis(formic acid), Intermediate 103 (335 mg, 0.50 mmol) and aqueous HCl solution (2 M, 5 ml, 10 mmol) was stirred at RT for 3 h. The reaction mixture was concentrated in vacuo then the residue was azeotroped with MeCN (3×10 ml) to afford the product as a colourless viscous oil (235 mg, 99%).

$^1$H NMR (500 MHz, CD$_3$OD) δ 4.25-4.18 (m, 2H), 3.91-3.83 (m, 2H), 3.81-3.76 (m, 2H), 3.74-3.64 (m, 6H), 3.62-3.51 (m, 2H), 3.50-3.39 (m, 4H), 3.10-3.03 (m, 2H), 2.22-2.13 (m, 2H).

LC/MS (System A): m/z (ESI+)=404 [MH+], $R_t$=0.12 min, ELS purity=100%.

Intermediate 104 may be reacted with a compound of general formula (II) using a similar method to that described in Examples 1-7 below to obtain a compound of general formula (I).

Intermediate 113—Synthesis of benzyl N-[1-(2-{[(tert-butoxy)carbonyl]amino}ethyl)piperidin-4-yl]carbamate

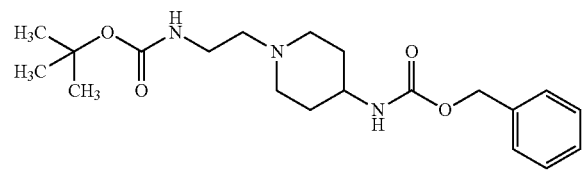 [SMILES: CC(C)(C)OC(=O)NCCN1CCC(NC(=O)OCc2ccccc2)CC1]

Triethylamine (515 µl, 3.69 mmol) was added to a solution of benzyl N-(4-piperidyl)carbamate hydrochloride (500 mg, 1.85 mmol) and tert-butyl N-(2-bromoethyl)carbamate (500 mg, 2.22 mmol) in MeCN (4 ml) in a pressure tube. The tube was sealed then the reaction mixture was heated at 85° C. for 16 h. Additional tert-butyl N-(2-bromoethyl)carbamate (150 mg, 0.67 mmol) was added then the reaction was left to heat at 85° C. for a further 1 h. The reaction mixture was concentrated in vacuo then the solid thus obtained was dissolved in the minimum of refluxing MeCN then allowed to cool to RT. The resultant suspension was filtered then the filtrate was concentrated in vacuo. The crude material was purified by flash column chromatography on a silica column (25 g). The column was eluted with CH$_2$Cl$_2$:MeOH, increasing the gradient linearly from 0-15% MeOH over 10 column volumes. The desired fractions were combined and evaporated to afford a viscous red oil (254 mg). The material thus obtained was partitioned between EtOAc (15 ml) and saturated aqueous NaHCO$_3$ solution (15 ml). The phases were separated then the organic phase was washed with water (2×15 ml) and brine (15 ml) then dried over Na$_2$SO$_4$ and concentrated in vacuo to afford the product as a pale red solid (140 mg, 20%).

$^1$H NMR (500 MHz, DMSO-d$_6$) δ 7.39-7.28 (m, 5H), 7.21 (d, J=7.6 Hz, 1H), 6.59 (t, J=5.3 Hz, 1H), 5.00 (s, 2H), 3.29-3.22 (m, 1H), 3.00 (q, J=6.4 Hz, 2H), 2.76 (d, J=11.5 Hz, 2H), 2.28 (t, J=6.9 Hz, 2H), 1.95 (t, J=11.0 Hz, 2H), 1.69 (d, J=10.5 Hz, 2H), 1.43-1.32 (m, 11H).

LC/MS (System A): m/z (ESI+)=378 [MH+], $R_t$=0.85 min, UV purity=100%.

Intermediate 114—Synthesis of tert-butyl N-[2-(4-aminopiperidin-1-yl)ethyl]carbamate

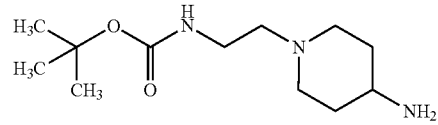 [SMILES: CC(C)(C)OC(=O)NCCN1CCC(N)CC1]

A mixture of benzyl N-[1-(2-{[(tert-butoxy)carbonyl]amino}ethyl)piperidin-4-yl]carbamate, Intermediate 113 (140 mg, 0.370 mmol) and palladium on carbon (10 wt %, 20 mg) in EtOH (5 ml) was stirred under a hydrogen atmosphere at RT for 2 h. The reaction mixture was filtered through a Celite pad then the filtrate was concentrated in vacuo to afford the product as a colourless oil (124 mg, 96%—yield corrected for 70% purity determined by NMR).

$^1$H NMR (500 MHz, DMSO-d$_6$) δ 6.61-6.53 (m, 1H), 4.37 (s, 2H), 3.00 (q, J=6.5 Hz, 2H), 2.76-2.71 (m, 2H), 2.49-2.45 (m, 1H), 2.27 (t, J=7.0 Hz, 2H), 1.91 (t, J=10.6 Hz, 2H), 1.67-1.60 (m, 2H), 1.37 (s, 9H), 1.22-1.15 (m, 2H).

LC/MS (System A): m/z (ESI+)=244 [MH+], $R_t$=0.14 min, ELS purity=100%.

Intermediate 115—Synthesis of bis(formic acid); tert-butyl N-[2-(4-{bis[(2S,3R)-2,3-dihydroxy-3-[(4R,5R)-5-hydroxy-2-phenyl-1,3-dioxan-4-yl]propyl]amino}piperidin-1-yl)ethyl]carbamate

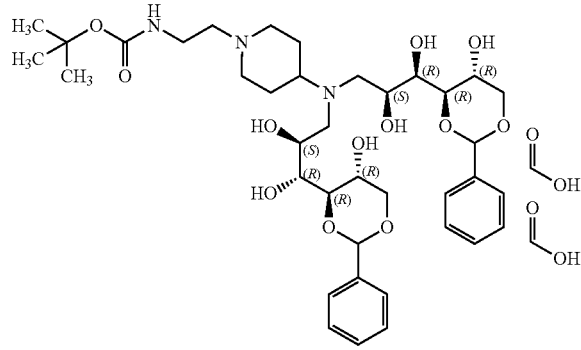

A mixture of tert-butyl N-[2-(4-aminopiperidin-1-yl)ethyl]carbamate, Intermediate 114 (70%, 725 mg, 2.08 mmol), 4,6-O-benzylidene-D-glucopyranose (3.57 g, 12.7 mmol) and AcOH (725 uL, 12.7 mmol) in MeOH (20 ml) was stirred at RT for 0.5 h. NaCNBH$_3$ (795 mg, 12.7 mmol) was added then the resulting mixture was stirred at RT for 5 days. The reaction was retreated with 4,6-O-benzylidene-D-glucopyranose (1.80 g, 6.29 mmol) and AcOH (362 uL, 6.32 mmol) then the reaction was left to stir at RT for 0.5 h. NaCNBH$_3$ (396 mg, 6.30 mmol) was added then the reaction was left to stir at RT for a further 18 h. The reaction was retreated with 4,6-O-benzylidene-D-glucopyranose (1.80 g, 6.29 mmol) and AcOH (362 uL, 6.32 mmol) then the reaction was left to stir at RT for 0.5 h. NaCNBH$_3$ (396 mg, 6.30 mmol) was added then the reaction was left to stir at RT for a further 18 h. The reaction mixture was concentrated under a stream of nitrogen then saturated aqueous NaHCO$_3$ solution was added dropwise until effervescence ceased. The resulting mixture was partitioned between saturated aqueous NaHCO$_3$ solution (150 ml) and EtOAc (150 ml). The phases were separated then the organic phase was washed with NaHCO$_3$ (150 ml), water (2×150 ml) and brine (150 ml), then dried over Na$_2$SO$_4$ and concentrated in vacuo to afford a pale yellow solid. The crude material was purified by flash column chromatography on C18 (120 g). The column was eluted with MeCN:water+0.1% formic acid using the following gradient (% MeCN, column volumes): 10%, 2 CV; 10-16%, 11 CV; 16%-100%, 4 CV; 100%, 1 CV. The desired fractions were combined and concentrated in vacuo to afford the product as a colourless oil (383 mg, 18%).

$^1$H NMR (500 MHz, CD$_3$OD) δ 8.38 (s, 2H), 7.52-7.48 (m, 4H), 7.39-7.35 (m, 6H), 5.54 (s, 2H), 4.26 (dd, J=10.7, 5.4 Hz, 2H), 4.07 (s (br), 2H), 4.02-3.94 (m, 2H), 3.93-3.90 (m, 2H), 3.79-3.73 (m, 2H), 3.63 (t, J=10.5 Hz, 2H), 3.27-3.20 (m, 3H), 3.17-2.92 (m, 6H), 2.69 (s (br), 1H), 2.38 (s (br), 1H), 2.23-2.08 (m, 1H), 1.94-1.85 (m, 2H), 1.83-1.72 (m, 1H), 1.67-1.57 (m, 1H), 1.46 (s, 9H).

LC/MS (System A): m/z (ESI$^+$)=375 [(M$^+$)+H$^+$], 748 [MH$^+$], R$_t$=0.82 min, UV purity=83%.

Intermediate 116—Synthesis of (2R,3R,4R,5S)-6-{[1-(2-aminoethyl)piperidin-4-yl][(2S,3R,4R,5R)-2,3,4,5,6-pentahydroxyhexyl]amino}hexane-1,2,3,4,5-pentol trihydrochloride

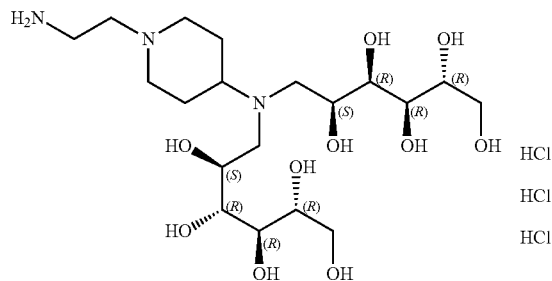

A mixture of bis(formic acid); tert-butyl N-[2-(4-{bis[(2S,3R)-2,3-dihydroxy-3-[(4R,5R)-5-hydroxy-2-phenyl-1,3-dioxan-4-yl]propyl]amino}piperidin-1-yl)ethyl]carbamate, Intermediate 115 (83%, 360 mg, 0.356 mmol) and aqueous HCl solution (4.0 M, 3.6 ml, 14.4 mmol) was stirred at RT for 0.5 h then concentrated in vacuo. The residue was dissolved in water:MeCN (9:1, 12 ml) then lyophilised to afford the product as a white foam (220 mg, 94%).

$^1$H NMR (500 MHz, Deuterium Oxide) δ 4.34-4.26 (m, 2H), 4.16-4.05 (m, 1H), 3.95-3.88 (m, 4H), 3.87 (d, J=2.9 Hz, 1H), 3.84 (d, J=3.0 Hz, 1H), 3.83-3.78 (m, 2H), 3.73-3.67 (m, 4H), 3.64-3.46 (m, 8H), 3.40-3.31 (m, 2H), 2.58 (d, J=14.0 Hz, 1H), 2.51 (d, J=13.7 Hz, 1H), 2.35-2.24 (m, 1H), 2.23-2.12 (m, 1H).

LC/MS (System B): m/z (ESI$^+$)=472 [MH$^+$], R$_t$=0.29 min, ELS purity=88%.

Intermediate 116 may be reacted with a compound of general formula (II) using a similar method to that described in Examples 1-7 below to obtain a compound of general formula (I).

Example 1—Synthesis of 6-(4-{bis[(2S,3R,4R,5R)-2,3,4,5,6-pentahydroxyhexyl]amino}piperidine-1-carbonyl)-2-{[(3,5-diamino-6-chloropyrazin-2-yl)formamido]methyl}-1,3-diethyl-1H-1,3-benzodiazol-3-ium trifluoroacetic acid trifluoroacetate

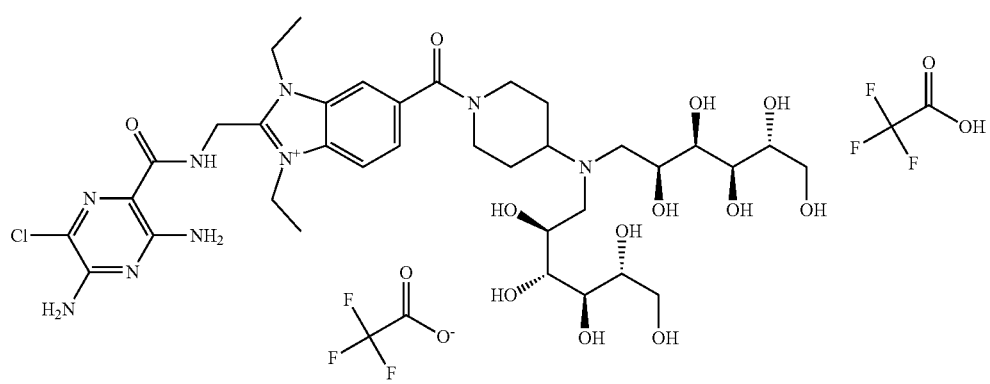 [SMILES: CCn1c(CNC(=O)c2nc(Cl)c(N)nc2N)[n+](CC)c2ccc(C(=O)N3CCC(N(C[C@H](O)[C@@H](O)[C@H](O)[C@H](O)CO)C[C@H](O)[C@@H](O)[C@H](O)[C@H](O)CO)CC3)cc21 ; O=C([O-])C(F)(F)F ; O=C(O)C(F)(F)F]

A suspension of 6-carboxy-2-{[(3,5-diamino-6-chloropyrazin-2-yl)formamido]methyl}-1,3-diethyl-1H-1,3-benzodiazol-3-ium bromide, Intermediate 9 (322 mg, 0.646 mmol) and CDI (157 mg, 0.968 mmol) in DMF (3 ml) was stirred at RT for 4 h. The resultant solution was added to (2R,3R,4R,5S)-6-{[(2S,3R,4R,5R)-2,3,4,5,6-pentahydroxyhexyl](piperidin-4-yl)amino}hexane-1,2,3,4,5-pentol dihydrochloride, Intermediate 14 (388 mg, 0.775 mmol) and rinsed in with further DMF (1 ml). The reaction was left to stir at RT for 16 h then concentrated in vacuo. The crude material was purified by flash column chromatography on C18 (30 g). The column was eluted with MeCN:H$_2$O+0.1% TFA using the following gradient (% MeCN, column volumes): 2%, 2 CVs; 2-20%, 15 CVs; 20%, 3 CV; 20-100%, 2 CVs; 100%, 2 CVs. The desired fractions were combined and concentrated in vacuo at RT. The residual material was diluted with water then lyophilised to afford the product as a white solid (300 mg, 44%).

$^1$H NMR (500 MHz, DMSO-d$_6$+D$_2$O) δ 8.13-8.04 (m, 2H), 7.69 (d, J=8.6 Hz, 1H), 4.97 (s, 2H), 4.74-4.55 (m, 5H), 4.09-3.92 (m, 2H), 3.85-3.75 (m, 1H), 3.64-3.56 (m, 4H), 3.52-3.07 (m, 13H), 2.94-2.77 (m, 1H), 2.24-1.56 (m, 3H), 1.42-1.34 (m, 6H). LC/MS (System D): m/z (ESI$^+$)=828 [M($^{35}$Cl)$^+$], 830 [M($^{37}$Cl)$^+$], R$_t$=1.34 min, UV purity=99%.

Example 2—Synthesis of 2-{[(3-amino-6-bromopyrazin-2-yl)formamido]methyl}-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium trifluoroacetic acid trifluoroacetate

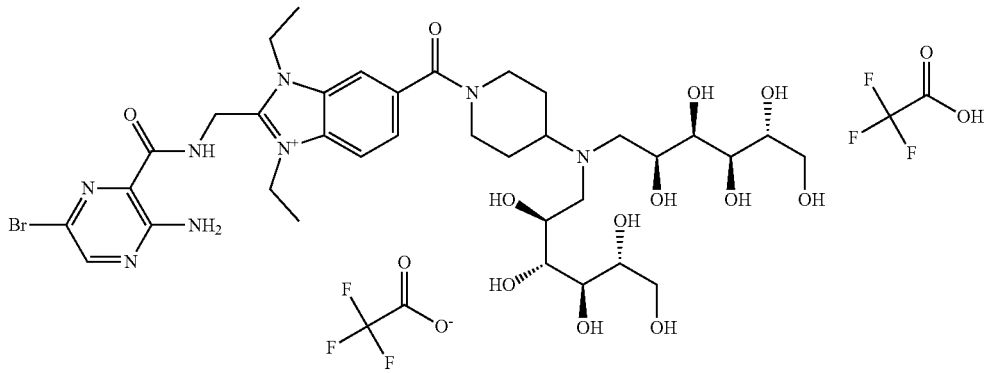 [SMILES: CCn1c(CNC(=O)c2nc(Br)cnc2N)[n+](CC)c2ccc(C(=O)N3CCC(N(C[C@H](O)[C@@H](O)[C@H](O)[C@H](O)CO)C[C@H](O)[C@@H](O)[C@H](O)[C@H](O)CO)CC3)cc21 ; O=C([O-])C(F)(F)F ; O=C(O)C(F)(F)F]

A solution of 2-{[(3-amino-6-bromopyrazin-2-yl)formamido]methyl}-6-carboxy-1,3-diethyl-1H-1,3-benzodiazol-3-ium bromide, Intermediate 11 (200 mg, 0.379 mmol), HBTU (144 mg, 0.379 mmol) and 4-methylmorpholine (83 µL, 0.76 mmol) in DMF (4 ml) was stirred at RT for 2 h. (2R,3R,4R,5S)-6-{[(2S,3R,4R,5R)-2,3,4,5,6-Pentahydroxyhexyl](piperidin-4-yl)amino}hexane-1,2,3,4,5-pentol dihydrochloride, Intermediate 14 (223 mg, 0.454 mmol) was added then the reaction was left to stir at RT for 16 h. The reaction mixture was concentrated in vacuo then the crude material was purified by flash column chromatography on C18 (30 g). The column was eluted with MeCN:H$_2$O+0.1% TFA using the following gradient (% MeCN, column volumes): 5%, 1.5 CVs; 5-13%, 4 CVs; 13%, 0.5 CV; 13-17%, 2.5 CVs; 17%, 11 CV; 17-25%, 2 CV; 25%, 2.5 CV; 25-30%, 0.5 CV; 30% 1 CV; 30-33%, 0.5 CV; 33%, 3 CV; 36-100%, 2 CV; 100%, 3 CVs. The desired fractions were combined and concentrated in vacuo at RT. The residual material was diluted with water/MeCN then lyophilised to afford the product as a yellow solid (67 mg, 16%).

$^1$H NMR (500 MHz, DMSO-d$_6$+D$_2$O) δ 9.64 (t, J=5.4 Hz, 1H), 8.39 (s, 1H), 8.17-8.04 (m, 2H), 7.76-7.65 (m, 1H), 5.06 (d, J=5.1 Hz, 2H), 4.76-4.53 (m, 5H), 4.12-3.89 (m, 2H), 3.72-3.06 (m, 17H), 2.95-2.79 (m, 1H), 2.28-1.51 (m, 4H), 1.50-1.28 (m, 6H).

LC/MS (System D): m/z (ESI$^+$)=429 [(M($^{79}$Br)+H)$^{2+}$], 430 [(M($^{81}$Br)+H)$^{2+}$], R$_t$=1.58 min, UV purity=100%.

Example 3—Synthesis of 6-[4-({bis[(2S,3R,4R,5R)-2,3,4,5,6-pentahydroxyhexyl]amino}methyl)piperidine-1-carbonyl]-2-{[(3,5-diamino-6-chloropyrazin-2-yl)formamido]methyl}-1,3-diethyl-1H-1,3-benzodiazol-3-ium trifluoroacetic acid trifluoroacetate

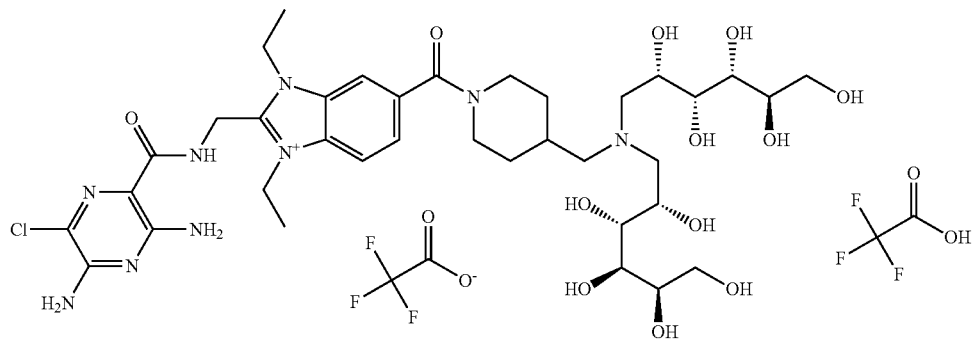 [SMILES: CCn1c(CNC(=O)c2nc(Cl)c(N)nc2N)[n+](CC)c2ccc(C(=O)N3CCC(CN(C[C@H](O)[C@@H](O)[C@H](O)[C@H](O)CO)C[C@H](O)[C@@H](O)[C@H](O)[C@H](O)CO)CC3)cc21 ; O=C([O-])C(F)(F)F ; O=C(O)C(F)(F)F]

A mixture of 6-carboxy-2-{[(3,5-diamino-6-chloropyrazin-2-yl)formamido]methyl}-1,3-diethyl-1H-1,3-benzodiazol-3-ium bromide, Intermediate 9 (150 mg, 0.301 mmol) and CDI (73 mg, 0.45 mmol) in DMF (1.5 ml) was stirred at RT for 3 h. Additional CDI (45 mg, 0.28) was added then the reaction was left to stir at RT for 16 h. (2R,3R,4R,5S)-6-{[(2S,3R,4R,5R)-2,3,4,5,6-Pentahydroxyhexyl][(piperidin-4-yl)methyl]amino}hexane-1,2,3,4,5-pentol dihydrochloride, Intermediate 19 (93%, 186 mg, 0.336 mmol) was added, followed by DMF (0.5 ml). The reaction mixture was stirred at RT for 25 h then concentrated in vacuo. The crude material was purified by flash column chromatography on C18 (30 g). The column was eluted with MeCN:H$_2$O+0.1% TFA using the following gradient (% MeCN, column volumes): 2%, 2 CVs; 2-10%, 7 CVs; 10-11%, 1 CV; 11%, 5 CVs; 11-20%, 7 CV; 20-100%, 2 CV; 100%, 1.5 CVs. The desired fractions were combined and concentrated in vacuo at RT. The residual material was dissolved in MeCN/water then lyophilised to afford the product as a yellow solid (55 mg, 16%). $^1$H NMR (500 MHz, DMSO-d$_6$+D2O) δ 8.04 (d, J=8.6 Hz, 1H), 8.02 (s, 1H), 7.70-7.58 (m, 1H), 4.95 (s, 2H), 4.72-4.57 (m, 4H), 4.54-4.38 (m, 1H), 4.05-3.95 (m, 2H), 3.68-3.61 (m, 2H), 3.58 (dd, J=11.0, 3.1 Hz, 2H), 3.54-3.45 (m, 3H), 3.43-3.36 (m, 4H), 3.34-3.23 (m, 4H), 3.20-3.01 (m, 3H), 2.94-2.72 (m, 1H), 2.26-1.47 (m, 2H), 1.42-1.33 (m, 7H), 1.32-1.11 (m, 2H).

LC/MS (System D): m/z (ESI$^+$)=842 [M($^{35}$Cl)$^+$], 844 [M($^{37}$Cl)$^+$], R$_t$=1.34 min, UV purity=96%.

Example 4—Synthesis of 6-[(3R)-3-{bis[(2S,3R,4R,5R)-2,3,4,5,6-pentahydroxyhexyl]amino}pyrrolidine-1-carbonyl]-2-{[(3,5-diamino-6-chloropyrazin-2-yl)formamido]methyl}-1,3-diethyl-1H-1,3-benzodiazol-3-ium trifluoroacetic acid trifluoroacetate

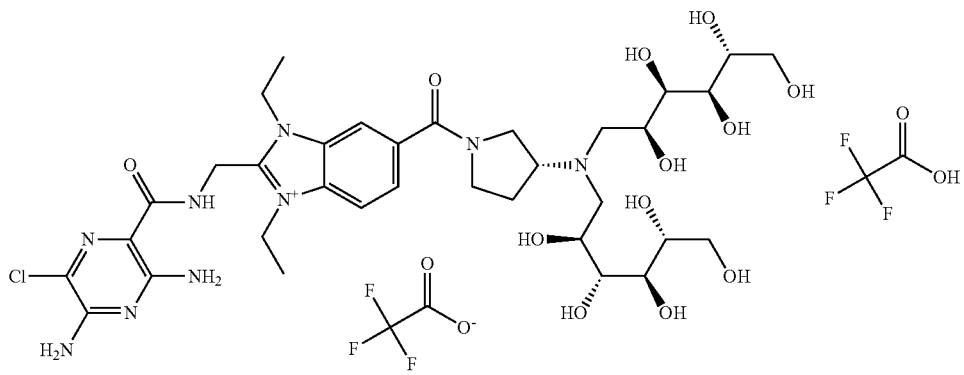 [SMILES: CCn1c(CNC(=O)c2nc(Cl)c(N)nc2N)[n+](CC)c2ccc(C(=O)N3CC[C@@H](N(C[C@H](O)[C@@H](O)[C@H](O)[C@H](O)CO)C[C@H](O)[C@@H](O)[C@H](O)[C@H](O)CO)C3)cc21 ; O=C([O-])C(F)(F)F ; O=C(O)C(F)(F)F]

A mixture of 6-carboxy-2-{[(3,5-diamino-6-chloropyrazin-2-yl)formamido]methyl}-1,3-diethyl-1H-1,3-benzodiazol-3-ium bromide, Intermediate 9 (128 mg, 0.256 mmol) and CDI (62 mg, 0.38 mmol) in DMF (1.5 ml) was stirred at RT for 6 h. An aliquot (0.75 ml) of the reaction mixture was added to (2R,3R,4R,5S)-6-{[(2S,3R,4R,5R)-2,3,4,5,6-pentahydroxyhexyl][(3R)-pyrrolidin-3-yl]amino}hexane-1,2,3,4,5-pentol dihydrochloride, Intermediate 21 (83%, 106 mg, 0.180 mmol). The reaction was left to stir at RT for 22 h then diluted with water (1 ml). The crude material was purified by flash column chromatography on C18 (30 g). The column was eluted with MeCN:H$_2$O+0.1% TFA using the following gradient (% MeCN, column volumes): 2%, 2 CVs; 2-3%, 1 CVs; 3%, 3 CV; 3-13%, 8 CVs; 13%, 3 CV; 13-20%, 6 CV; 20-100%, 2CV; 100%, 2 CVs. The desired fractions were combined and concentrated in vacuo at RT.

The residual material was dissolved in MeCN/water then lyophilised to afford the product as a yellow solid (37 mg, 27%).

$^1$H NMR (500 MHz, DMSO-$d_6$+$D_2O$) δ 8.13 (s, 1H), 8.11-8.01 (m, 1H), 7.76 (d, J=8.8 Hz, 1H), 4.96 (s, 2H), 4.74-4.51 (m, 4H), 4.41-4.19 (m, 1H), 4.12-3.94 (m, 2H), 3.75-3.21 (m, 17H), 2.39-2.04 (m, 3H), 1.44-1.32 (m, 6H).

LC/MS (System D): m/z (ESI$^+$)=814 [M($^{35}$Cl)$^+$], 816 [M($^{37}$Cl)$^+$], R$_t$=1.25 min, UV purity=97%.

Example 5—Synthesis of 6-[(2-{bis[(2S,3R,4R,5R)-2,3,4,5,6-pentahydroxyhexyl]amino}ethyl)carbamoyl]-2-{[(3,5-diamino-6-chloropyrazin-2-yl)formamido]methyl}-1,3-diethyl-1H-1,3-benzodiazol-3-ium trifluoroacetic acid trifluoroacetate

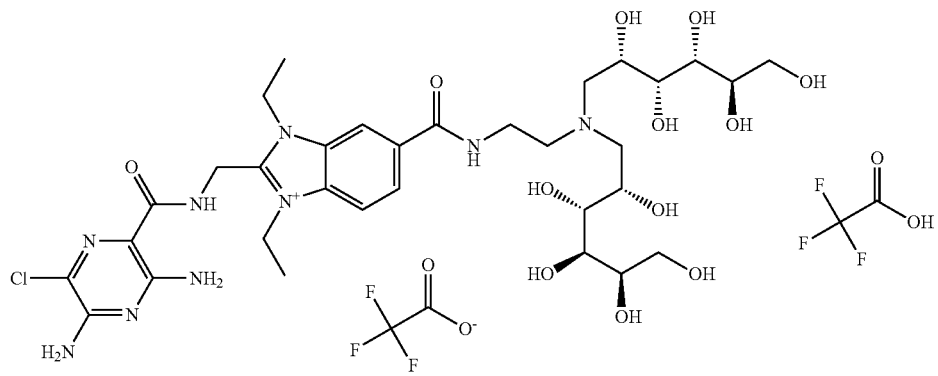 [SMILES: CCn1c(CNC(=O)c2nc(Cl)c(N)nc2N)[n+](CC)c2ccc(C(=O)NCCN(C[C@H](O)[C@@H](O)[C@H](O)[C@H](O)CO)C[C@H](O)[C@@H](O)[C@H](O)[C@H](O)CO)cc21 ; O=C([O-])C(F)(F)F ; O=C(O)C(F)(F)F]

A mixture of 6-carboxy-2-{[(3,5-diamino-6-chloropyrazin-2-yl)formamido]methyl}-1,3-diethyl-1H-1,3-benzodiazol-3-ium bromide, Intermediate 9 (150 mg, 0.301 mmol) and CDI (73 mg, 0.45 mmol) in DMF (1.5 ml) was stirred at RT for 4.5 h. (2R,3R,4R,5S)-6-[(2-aminoethyl)[(2S,3R,4R,5R)-2,3,4,5,6-Pentahydroxyhexyl]amino]hexane-1,2,3,4,5-pentol dihydrochloride, Intermediate 23 (94%, 166 mg, 0.338 mmol) was added then the reaction was left to stir at RT for 16 h then diluted with water (1 ml). The crude material was purified by flash column chromatography on C18 (30 g). The column was eluted with MeCN:$H_2O$+0.1% TFA using the following gradient (% MeCN, column volumes): 2%, 2 CVs; 2-10%, 6.5 CVs; 10%, 7.5 CV; 10-20%, 7.5 CVs; 20-100%, 2 CV; 100%, 2 CVs.

The desired fractions were combined and concentrated in vacuo at RT. The residual material was dissolved in MeCN/water then lyophilised to afford the product as a yellow solid (93 mg, 30%).

$^1$H NMR (500 MHz, DMSO-$d_6$+$D_2O$) δ 8.38 (s, 1H), 8.11 (d, J=8.8 Hz, 1H), 8.09-8.04 (m, 1H), 5.05-4.91 (m, 2H), 4.73-4.58 (m, 4H), 4.09-3.97 (m, 2H), 3.69-3.64 (m, 3H+HDO), 3.62-3.25 (m, 15H), 1.50-1.31 (m, 6H).

LC/MS (System D): m/z (ESI$^+$)=788 [M($^{35}$Cl)$^+$], 790 [M($^{37}$Cl)$^+$], R$_t$=1.30 min, UV purity=97%.

Example 6—Synthesis of 2-{[(3,5-diamino-6-chloropyrazin-2-yl)formamido]methyl}-1,3-diethyl-6-{[(14S,15R,16R,17R)-14,15,16,17,18-pentahydroxy-12-[(2S,3R,4R,5R)-2,3,4,5,6-pentahydroxyhexyl]-3,6,9-trioxa-12-azaoctadecan-1-yl]carbamoyl}-1H-1,3-benzodiazol-3-ium trifluoroacetic acid trifluoroacetate

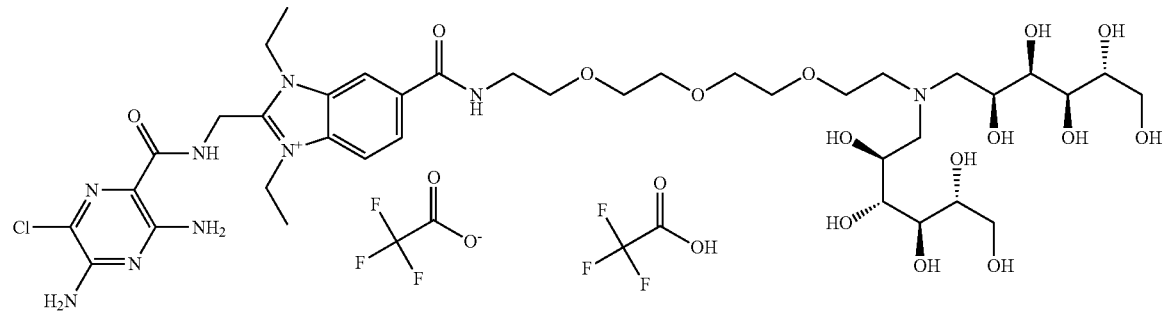 [SMILES: CCn1c(CNC(=O)c2nc(Cl)c(N)nc2N)[n+](CC)c2ccc(C(=O)NCCOCCOCCOCCN(C[C@H](O)[C@@H](O)[C@H](O)[C@H](O)CO)C[C@H](O)[C@@H](O)[C@H](O)[C@H](O)CO)cc21 ; O=C([O-])C(F)(F)F ; O=C(O)C(F)(F)F]

A mixture of 6-carboxy-2-{[(3,5-diamino-6-chloropyrazin-2-yl)formamido]methyl}-1,3-diethyl-1H-1,3-benzodiazol-3-ium bromide, Intermediate 9 (150 mg, 0.301 mmol) and CDI (73 mg, 0.45 mmol) in DMF (1.5 ml) was stirred at RT for 4.5 h. Additional CDI (73 mg, 0.45) was added then the reaction was left to stir at RT for 18 h. The reaction mixture was added to (14S,15R,16R,17R)-1-amino-12-[(2S,3R,4R,5R)-2,3,4,5,6-pentahydroxyhexyl]-3,6,9-trioxa-12-azaoctadecane-14,15,16,17,18-pentol dihydrochloride, Intermediate 28 (96%, 214 mg, 0.346 mmol). The resultant mixture was left to stir at RT for 21 h then diluted with water (2 ml). The crude material was purified by flash column chromatography on C18 (30 g). The column was eluted with MeCN:H$_2$O+0.1% TFA using the following gradient (% MeCN, column volumes): 2%, 2 CVs; 2-9%, 6 CVs; 9%, 1.5 CV; 9-14%, 4 CVs; 14%, 6 CV; 14-19%, 4 CV; 19-20%, 0.5 CV; 20-100%, 2 CVs; 100% 1.5 CV. The desired fractions were combined and concentrated in vacuo at RT. The residual material was dissolved in MeCN/water then lyophilised to afford a yellow solid (74 mg). The material thus obtained was further purified by flash column chromatography on C18 (12 g). The column was eluted with MeCN:H$_2$O+0.1% TFA using the following gradient (% MeCN, column volumes): 2%, 2 CVs; 2-14%, 10 CVs; 14%, 5.5 CV; 14-20%, 5 CVs; 20-100%, 2 CVs; 100% 2 CV. The desired fractions were combined and concentrated in vacuo at RT. The residual material was dissolved in MeCN/water then lyophilised to afford the product as an off-white solid (9 mg, 3%).

$^1$H NMR (500 MHz, DMSO-d$_6$+D$_2$O) δ 8.41 (s, 1H), 8.10-8.07 (m, 2H), 5.05-4.92 (m, 2H), 4.71-4.57 (m, 4H), 4.04-3.93 (m, 2H), 3.67-3.62 (m, 2H), 3.61-3.17 (m, 28H), 1.48-1.30 (m, 6H).

LC/MS (System D): m/z (ESI$^+$)=461 [(M($^{35}$Cl)+H)$^{2+}$], 462 [(M($^{37}$Cl)+H)$^{2+}$], R$_t$=1.48 min, UV purity=96%.

Example 7—Synthesis of 6-({2-[4'-(2-{bis[(2S,3R,4R,5R)-2,3,4,5,6-pentahydroxyhexyl]amino}ethyl)-[1,1'-biphenyl]-4-yl]ethyl}carbamoyl)-2-{[(3,5-diamino-6-chloropyrazin-2-yl)formamido]methyl}-1,3-diethyl-1H-1,3-benzodiazol-3-ium trifluoroacetic acid trifluoroacetate A mixture of 6-carboxy-2-{[(3,5-diamino-6-chloropyrazin-2-yl)formamido]methyl}-1,3-diethyl-1H-1,3-benzodiazol-3-ium bromide, Intermediate 9 (128 mg, 0.256 mmol) and CDI (62 mg, 0.38 mmol) in DMF (1.5 ml) was stirred at RT for 6 h. An aliquot (0.75 ml) of the reaction mixture was added to (2R,3R,4R,5S)-6-({2-[4'-(2-aminoethyl)-[1,1'-biphenyl]-4-yl]ethyl}[(2S,3R,4R,5R)-2,3,4,5,6-pentahydroxyhexyl]amino)hexane-1,2,3,4,5-pentol dihydrochloride, Intermediate 33 (94%, 154 mg, 0.226 mmol). Additional DMF (0.75 ml) was used to rinse the intermediate solution into the reaction vessel. The reaction mixture was stirred at RT for 16 h then concentrated under a stream of nitrogen. The residue thus obtained was diluted with water (1 ml) then purified by flash column chromatography on C18 (30 g). The column was eluted with MeCN:H$_2$O+0.1% TFA using the following gradient (% MeCN, column volumes): 2%, 2 CVs; 2-6%, 3 CVs; 6%, 0.5 CV; 6-10%, 3.5 CVs; 10%, 4 CV; 10-20%, 8.5 CV; 20-100%, 2 CV; 100%, 2 CVs. The desired fractions were combined and concentrated in vacuo at RT. The residual material was dissolved in MeCN/water then lyophilised to afford a yellow oil. The material thus obtained was further purified by flash column chromatography on C18 (30 g). The column was eluted with MeCN:H$_2$O+0.1% TFA using the following gradient (% MeCN, column volumes): 10%, 2 CVs; 10-21%, 2 CVs; 21%, 0.5 CV; 21-25%, 1 CVs; 25%, 4 CV; 25-35%, 2 CV; 35%, 1 CV; 35-84%, 9 CV; 100%, 3.5 CVs. The desired fractions were combined and concentrated in vacuo at RT. The residual material was dissolved in MeCN/water then lyophilised to afford the product as a yellow solid (35 mg, 23%).

$^1$H NMR (500 MHz, DMSO-d$_6$+D$_2$O) δ 8.29 (s, 1H), 8.05-7.90 (m, 2H), 7.61-7.50 (m, 4H), 7.38-7.27 (m, 4H), 4.94 (s, 2H), 4.68-4.52 (m, 4H), 4.09-4.06 (m, 2H+HDO), 3.73-3.21 (m, 18H), 3.08-2.97 (m, 2H), 2.95-2.84 (m, 2H), 1.41-1.33 (m, 6H). LC/MS (System D): m/z (ESI$^+$)=485 [(M($^{35}$Cl)+H)$^{2+}$], 486 [(M($^{37}$Cl)+H)$^{2+}$], R$_t$=2.03 min, UV purity=100%.

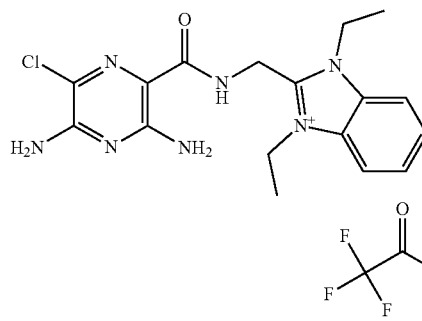
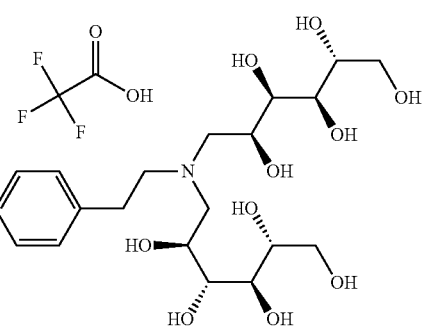

Other Compounds of the Invention

Intermediate 7 may be reacted with intermediate 8 to give a compound of the formula:

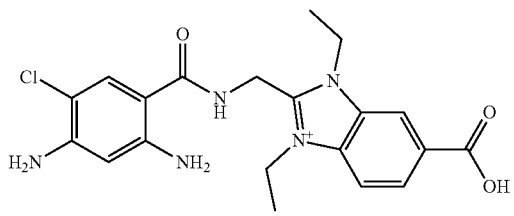 [SMILES: CCn1c(CNC(=O)c2cc(Cl)c(N)cc2N)[n+](CC)c2ccc(C(=O)O)cc21]

This compound may be reacted with Intermediate 104 or Intermediate 116 to yield further compounds of general formula (I).

BIOLOGICAL EXAMPLES

Example 8—Short Circuit Current Assay to Determine ENaC Blocker Potency in Human Bronchial Epithelial Cells Cell Culture Human bronchial epithelial cells (HBECs) (Lonza, UK) were cultured using a modification of the method described by Coote et al, (2008). Cells were seeded into plastic T-75 flasks and grown in Bronchial Epithelial Cell Growth Medium (BEGM) (Lonza, UK) supplemented with bovine pituitary extract (52 ng/mL), hydrocortisone (0.5 µg/mL), human recombinant Epidermal Growth Factor (0.5 ng/mL), epinephrine (0.5 ng/mL), transferrin (10 ng/mL), insulin (5 ng/mL), retinoic acid (0.1 ng/mL), triiodothyronine (6.5 ng/mL), gentamycin (50 µg/mL) and amphotericin-B (50 ng/mL). Medium was changed every 48 hours until cells were 90% confluent. Cells were then passaged and seeded ($8.25 \times 10^5$ cells/insert) onto polycarbonate Snapwell™ inserts (Costar, UK) in differentiation media containing 50% DMEM in BGEM with the same supplements as above but without triiodothyronine and a final retinoic acid concentration of 50 nM (all-trans retinoic acid; Sigma-Aldrich, UK). Cells were maintained submerged for the first 7 days in culture after which time they were exposed to an apical air interface for the remainder of the culture period. From the first day of establishment of an AL1, HBEC were fed with a DMEM:HAMS F-12 (1:1) media containing 2% Ultroser G (Pall BioSepra, France) with gentamycin (50 µg/mL) and amphotericin B (50 ng/mL). Cells were used for short-circuit current assay between days 14-21 after the establishment of the AL1. At all stages of culture, cells were maintained at 37° C. in 5% $CO_2$ in an air incubator.

Example 9—Bronchoalveolar Lavage

A 0.1 mg/mL solution of ENaC inhibitor in 5% dextrose was administered intratracheally to a rat weighing 225-250 g. A volume of 1 mL/Kg was used. After 6 hours, lungs were lavaged with 3×4 mL of sterile saline. A 1 mL aliquot was subsequently snap frozen. Lungs were excised, weighed and snap frozen. Compound levels in the BAL and lung tissue were subsequently determined using LC/MS/MS bioanalysis.

The results from Examples 8 and 9 are presented in Table 1.

| Example | ENaC | BAL @ 6 hours (ng/mL) |
|---|---|---|
| 1 | 6 | 222 |
| 2 | 18 | |
| 3 | 4 | 210 |
| 4 | 11 | 524 |
| 5 | 5 | 471 |
| 6 | 4 | 251 |
| 7 | 1 | 645 |

The invention claimed is:
1. A compound of general formula (I) including all tautomeric forms, all enantiomers and isotopic variants and salts thereof:

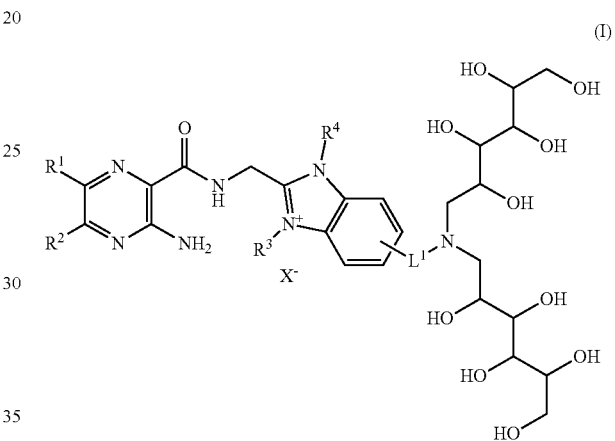

wherein
$X^-$ is an anion;
$R^1$ is halo, cyano, $C_{1-3}$ alkyl, $C_{1-3}$ haloalkyl, or —S($C_{1-3}$ alkyl);
$R^2$ is H or $NH_2$;
each of $R^3$ and $R^4$ is independently $C_{1-10}$ alkyl, wherein one or more —$CH_2$— groups is optionally replaced by —O—, —S— or provided that adjacent —$CH_2$— groups are not so replaced, and which is optionally substituted with one or more substituents selected from halo, —$OR^6$, —$SR^6$, —$NR^6R^7$, aryl, heteroaryl, cycloalkyl, heterocyclyl, —C(O)$OR^6$, or —C(O)$NR^6R^7$;
wherein each $R^5$, $R^6$ and $R^7$ is independently selected from H or $Ci$-4 alkyl;
$L^1$ is:
—$Z^1$—, -$Q^1$-, —$Z^1Q^1$-, -$Q^1Z^1$—, —$Z^1Q^1Z^2$—, -$Q^1Q^2$-, -$Q^1Q^2Z^1$—, -$Q^1Q^2Z^1Q^3Z^2$—, or -$Z^1Q^1OQ^2OQ^3$-;
—$OZ^1$—, -$OQ^1$-, —$OZ^1Q^1$-, -$OQ^1Z^1$—, —$OZ^1Q^1Z^2$—, -$OQ^1Q^2$-, -$OQ^1Q^2Z^1$—, -$OQ^1Q^2Z^1Q^3Z^2$—, or —$OZ^1Q^1OQ^2OQ^3$-;
—$NR^8Z^1$—, —$NR^8Q^1$-, —$NR^8Z^1Q^1$-, —$NR^8Q^1Z^1$—, —$NR^8Z^1Q^1Z^2$—, —$NR^8Q^1Q^2$-, —$NR^8Q^1Q^2Z^1$—, —$NR^8Q^1Q^2Z^1Q^3Z^2$—, or —$NR^8Z^1Q^1OQ^2OQ^3$;
—$Z^1NR^8Z^2$—, -$Q^1$-$Z^1NR^8Z^2$—, —$Z^1NR^8Z^2Q^1$-, or -$Q^1Z^1NR^8Z^2Q^2Z^3$—;
—$Z^1O(CH_2CH_2O)_nZ^2$—, —$Z^1O(CH_2CH_2O)_nQ^1$-, —$Z^1O(CH_2CH_2O)_nZ^2Q^1$, —$Z^1O(CH_2CH_2O)_nQ^1Z^2$—, -$Q^1Z^1O(CH_2CH_2O)_nZ^2$—, -$Q^1Z^1O(CH_2CH_2O)_nQ^1$-, -$Q^1Z^1O(CH_2CH_2O)_nZ^2Q^1$, —$Z^1O$ (CH₂CH₂O)ₙZ²Q¹Z³-, —C(O)Z¹—, —C(O)Q¹-, —C(O)Z¹Q¹-, —C(O)Z¹Q¹Z²—, —C(O)Q¹Z¹—, —C(O)Q¹Q²-, —C(O)Q¹Q²Z¹—, —C(O)Q¹NR⁸C(O)Z¹—, —C(O)Q¹NR⁸C(O)Z¹Q²-, —C(O)Q¹NR⁸C(O)Z¹Q²Q³—C(O)Q¹NR⁸C(O)Z¹Q²Z²—, or —C(O)Z¹Q¹OQ²OQ³-;

—C(O)NR⁸Z¹—, —C(O)NR⁸Q¹-, —C(O)NR⁸Z¹Q¹-, —C(O)NR⁸Z¹Q¹Z²—, —C(O)NR⁸Q¹Z¹—, —C(O)NR⁸Q¹Q²-, —C(O)NR⁸Q¹Q²Z¹—, —C(O)NR⁸Z¹Q¹Q²Z², —C(O)NR⁸(CH₂CH₂O)ₙZ¹—C(O)NR⁸Z¹O(CH₂O)ₙZ²—, —C(O)NR⁸Z¹Q¹Z²NR⁹Z³—, —C(O)NR⁸Z¹NR⁹Z²—, —C(O)NR⁸Q¹Z¹NR⁹Z²—, —C(O)NR⁸Z¹Q¹OQ²OQ³, or —C(O)NR⁸Z¹Q¹OQ²OQ³Z²;

—Z¹C(O)NR⁸Z²—, —Z¹C(O)NR⁸Q¹-, —Z¹C(O)NR⁸Z²Q¹-, —Z¹C(O)NR⁸Q¹Z²—, —Z¹C(O)NR⁸Q¹Q²-, —Z¹C(O)Q¹-, —Z¹C(O)Q¹Z²—, —Z¹C(O)Q¹Q²-, or —Z¹C(O)NR⁸Q¹Q²Z²—;

—C(O)OZ¹—, —C(O)OQ¹-, —C(O)OZ¹Q¹-, —C(O)OZ¹Q¹Z²—, —C(O)OQ¹Z¹—, —C(O)OQ¹Q²-, or —C(O)OQ¹Q²Z¹—;

-Q¹C(O)Q²-, Q¹C(O)Z¹—, -Q¹C(O)Q²Z¹—, Q¹C(O)Q²Q³-, Q¹C(O)Z¹Q²-, or Q¹C(O)Q²Q³Z¹—; or

C(=NR¹⁰)NR⁸Z¹—, C(=NR¹⁰)NR⁸Q¹-, C(=NR¹⁰)NR⁸Z¹Q¹-, C(=NR¹⁰)NR⁸Z¹Q¹Z²—, C(=NR¹⁰)NR⁸Q¹Z¹—, —C(=NR¹⁰)NR⁸Q¹Q², or C(=NR¹⁰)NR⁸Q¹Q²Z¹;

each of Z¹, Z² and Z³ is independently C₁₋₁₂ alkylene, C₂₋₁₂ alkenylene, or C₂₋₁₂ alkynylene any of which is optionally substituted by one or more halo, OH, C(O)NR¹¹R¹², C(O)OR¹¹ or NR¹¹R¹²;

each R¹¹ and R¹² is independently H or C₁₋₆ alkyl;

each of Q¹, Q² and Q³ is independently carbocyclyl, heterocyclyl, aryl or heteroaryl any of which is optionally substituted with one or more substituents selected from halo, OH, C(O)NR¹¹R¹², C(O)OR¹¹ or NR¹¹R¹², or, for carbocyclyl and heterocyclyl groups, oxo, wherein R¹¹ and R¹² are as defined above;

n is 1 to 6;

each R⁸ and R⁹ is independently selected from H or C₁₋₁₂ alkyl optionally substituted with one or more halo or OH groups; and R¹⁰ is H or C₁₋₆ alkyl.

2. The compound according to claim 1, wherein the compound is of general formula (IA):

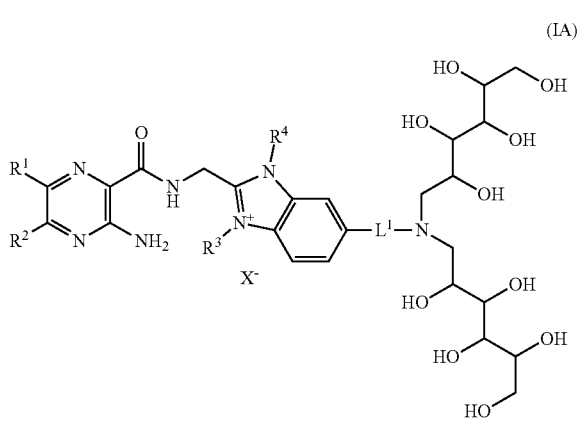

(IA)

wherein R¹, R², R³, R⁴, L¹ and X⁻ are as defined for general formula (I);

or the compound is of general formula (IB):

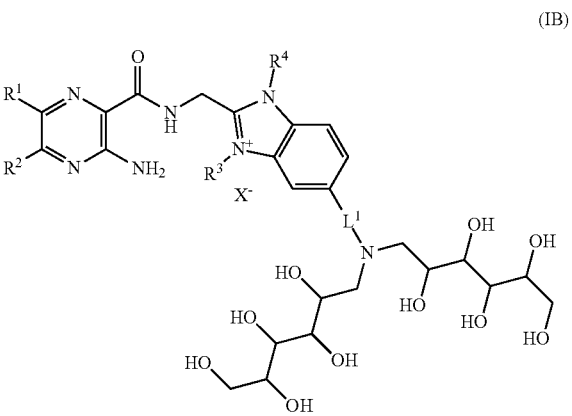

(IB)

wherein R¹, R², R³, R⁴, L¹ and X⁻ are as defined for general formula (I).

3. The compound according to claim 1 wherein R¹ is halo or methyl.

4. The compound according to claim 1 wherein R² is NH₂.

5. The compound according to claim 1 wherein:
one or both of R³ and R⁴ are methyl, ethyl, benzyl, pyridylmethyl, —CH₂OH, —CH₂NH₂, —CH₂CH₂OH or CH₂CH₂NH₂; or
both R³ and R⁴ are C₁₋₁₀ alkyl; or
at least one of R³ and R⁴ is —CH₂CH₂OCH₂CH₂OH or —CH₂CH₂OCH₂CH₂OCH₂CH₂OH.

6. The compound according to claim 1 wherein L¹ is:
—C(O)Z¹—, —C(O)Q¹-, —C(O)Z¹Q¹-, —C(O)Z¹Q¹Z²—, —C(O)Q¹Z¹—, —C(O)Q¹Q²-, —C(O)Q¹Q²Z¹—, —C(O)Q¹NR⁸C(O)Z¹—, —C(O)Q¹NR⁸C(O)Z¹Q²-, —C(O)Q¹NR⁸C(O)Z¹Q²Q³—C(O)Q¹NR⁸C(O)Z¹Q²Z²—, or —C(O)NR⁸Z¹—, —C(O)NR⁸Q¹-, —C(O)NR⁸Z¹Q¹, C(O)NR⁸Z¹Q¹Z²—, —C(O)NR⁸Q¹Z¹—, —C(O)NR⁸Q¹Q²-, —C(O)NR⁸Q¹Q²Z¹, C(O)NR⁸Z¹Q¹Q²Z², —C(O)NR⁸(CH₂CH₂O)ₙZ¹—C(O)NR⁸Z¹O(CH₂O)ₙZ²—, —C(O)NR⁸Z¹Q¹Z²NR⁹Z³—, —C(O)NR⁸Z¹NR⁹Z²—, —C(O)NR⁸Q¹Z¹NR⁹Z²—, —C(O)NR⁸Z¹Q¹OQ²OQ³-, or —C(O)NR⁸Z¹Q¹OQ²OQ³Z²—.

7. The compound according to claim 6 wherein L¹ is —C(O)Q¹-, —C(O)Q¹Z¹—, —C(O)NR⁸Z¹—, —C(O)NR⁸Z¹Q¹Q²Z²—, or —C(O)NR⁸(CH₂CH₂O)ₙZ¹—.

8. The compound according to claim 1 wherein L¹ is —C(O)Q¹-, —C(O)Q¹Z¹—, —C(O)Q¹Q²-, —C(O)Q¹Q²Z¹—, —C(O)Q¹NR⁸C(O)Z¹—, —C(O)Q¹NR⁸C(O)Z¹Q²-, —C(O)Q¹NR⁸C(O)Z¹Q²Q³-, or —C(O)Q¹NR⁸C(O)Z¹Q²Z²—, and Q¹ is pyrrolidin-1-yl, piperidin-1-yl, or piperazin-1-yl; or L¹ is -Q¹C(O)Q²-, -Q¹C(O)Q²Z¹—, Q¹C(O)Q²Q³-, or Q¹C(O)Q²Q³Z¹—, and Q² is pyrrolidin-1-yl, piperidin-1-yl, or piperazin-1-yl.

9. The compound according to claim 1 selected from the following salts:

6-(4-{bis[(2S,3R,4R,5R)-2,3,4,5, 6-pentahydroxyhexyl]amino}piperidine-1-carbonyl)-2-{[(3,5-diamino-6-chloropyrazin-2-yl)formamido]methyl}-1,3-diethyl-1H-1,3-benzodiazol-3-ium;

2-{[(3-amino-6-bromopyrazin-2-yl)formamido]methyl}-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium;

6-[4-({bis[(2S,3R,4R,5R)-2,3,4,5,6-pentahydroxyhexyl]amino}methyl)piperidine-1-carbonyl]-2-{[(3,5-diamino-6-chloropyrazin-2-yl)formamido]methyl}-1,3-diethyl-1H-1,3-benzodiazol-3-ium;

6-[(3R)-3-{bis[(2S,3R,4R,5R)-2,3,4,5,6-pentahydroxyhexyl] amino}pyrrolidine-1-carbonyl]-2-{[(3,5-diamino-6-chloropyrazin-2-yl)formamido]methyl}-1,3-diethyl-1H-1,3-benzodiazol-3-ium;

6-[(2-{bis[(2S,3R,4R,5R)-2,3,4,5,6-pentahydroxyhexyl]amino}ethyl)carbamoyl]-2-{[(3,5-diamino-6-chloropyrazin-2-yl)formamido]methyl}-1,3-diethyl-1H-1,3-benzodiazol-3-ium;

2-{[(3,5-diamino-6-chloropyrazin-2-yl)formamido]methyl}-1,3-diethyl-6-{-1H-1,3-benzodiazol-3-ium; or 6-({2-[4'-(2-{bis[(2S,3R,4R,5R)-2,3,4,5,6-pentahydroxyhexyl] amino}ethyl)-[1,1'-biphenyl]-4-yl]ethyl}carbamoyl)-2-{[(3,5-diamino-6-chloropyrazin-2-yl)formamido]methyl}-1,3-diethyl-1H-1,3-benzodiazol-3-ium;

wherein the counter ion is an anion X⁻ as defined in claim 1.

10. A pharmaceutical composition comprising the compound according to claim 1 and a pharmaceutically acceptable excipient.

* * * * *

UNITED STATES PATENT AND TRADEMARK OFFICE
CERTIFICATE OF CORRECTION

PATENT NO. : 11,370,778 B2
APPLICATION NO. : 16/756416
DATED : June 28, 2022
INVENTOR(S) : Duncan Alexander Hay et al.

It is certified that error appears in the above-identified patent and that said Letters Patent is hereby corrected as shown below:

In the Claims

In Claim 1, Column 84, Line 45, after "or" insert -- -$NR^5$-, --.

In Claim 1, Column 84, Line 52, delete "Ci-4" and insert -- $C_{1-4}$ --.

In Claim 1, Column 84, Line 61, delete "–$NR^8Z^1Q^1OQ^2OQ^3$;" and insert -- –$NR^8Z^1Q^1OQ^2OQ^3$–; --.

In Claim 1, Column 84, Line 62, delete "–$Q^{1-}Z^1NR^8Z^2$–," and insert -- –$Q^1Z^1NR^8Z^2$–, --.

In Claim 1, Column 84, Line 65, delete "–$Z^1O(CH_2CH_2O)_nZ^2Q^1$," and insert
-- –$Z^1O(CH_2CH_2O)_nZ^2Q^1$–, --.

In Claim 1, Column 84, Line 67 to Column 85, Line 1, delete "–$Z^1O(CH_2CH_2O)_nZ^2Q^1Z^3$-—$C(O)Z^1$–," and insert -- –$Z^1O(CH_2CH_2O)_nZ^2Q^1Z^3$–, –$C(O)Z^1$–, --.

In Claim 1, Column 85, Lines 4-5, delete "–$C(O)Q^1NR^8C(O)Z^1Q^2Q^3$- —$C(O)Q^1NR^8C(O)Z^1Q^2Z^2$—,"
and insert -- –$C(O)Q^1NR^8C(O)Z^1Q^2Q^3$–, –$C(O)Q^1NR^8C(O)Z^1Q^2Z^2$–, --.

In Claim 1, Column 85, Line 7, delete "–$C(O)NR^8Z'$–," and insert -- –$C(O)NR^8Z^1$–, --.

In Claim 1, Column 85, Lines 11-12, delete "–$C(O)NR^8(CH_2CH_2O)_nZ^1$—$C(O)NR^8Z^1O(CH_2O)_nZ^2$–,"
and insert -- –$C(O)NR^8(CH_2CH_2O)_nZ^1$–, –$C(O)NR^8Z^1O(CH_2O)_nZ^2$–, --.

In Claim 1, Column 85, Lines 14-15, delete "–$C(O)NR^8Z^1Q^1OQ^2OQ^3$, or –$C(O)NR^8Z^1Q^1OQ^2OQ^3Z^2$;"
and insert -- –$C(O)NR^8Z^1Q^1OQ^2OQ^3$–, or –$C(O)NR^8Z^1Q^1OQ^2OQ^3Z^2$–; --.

In Claim 1, Column 85, Lines 17-18, delete "–$Z^1C(O)NR^8Q^1Q^2$-," and insert -- –$Z^1C(O)NR^8Q^1Q^2$–, --.

Signed and Sealed this
Thirteenth Day of December, 2022

Katherine Kelly Vidal
*Director of the United States Patent and Trademark Office*

In Claim 1, Column 85, Lines 23-24, delete "$Q^1C(O)Z^1—, -Q^1C(O)Q^2Z^1—, Q^1C(O)Q^2Q^3-, Q^1C(O)Z^1Q^2-,$ or $Q^1C(O)Q^2Q^3Z^1—$" and insert -- $–Q^1C(O)Z^1–, –Q^1C(O)Q^2Z^1–, –Q^1C(O)Q^2Q^3–, –Q^1C(O)Z^1Q^2–,$ or $–Q^1C(O)Q^2Q^3Z^1–$ --.

In Claim 1, Column 85, Lines 25-26, delete "$C(=NR^{10})NR^8Z^1—, C(=NR^{10})NR^8Q^1-, C(=NR^{10})NR^8Z^1Q^1-, C(=NR^{10})NR^8Z^1Q^1Z^2—,$" and insert -- $–C(=NR^{10})NR^8Z^1–, –C(=NR^{10})NR^8Q^1–, –C(=NR^{10})NR^8Z^1Q^1–, –C(=NR^{10})NR^8Z^1Q^1Z^2–,$ --.

In Claim 1, Column 85, Lines 26-27, delete "$C(—NR^{10})NR^8Q^1Z^1—, —C(=NR^{10})NR^8Q^1Q^2,$" and insert -- $–C(=NR^{10})NR^8Q^1Z^1–, C(=NR^{10})NR^8Q^1Q^2–,$ --.

In Claim 1, Column 85, Lines 27-28, delete "$C(=NR^{10})NR^8Q^1Q^2Z^1;$" and insert -- $–C(=NR^{10})NR^8Q^1Q^2Z^1;$ --.

In Claim 2, Column 86, Line 3, delete "(TB):" and insert -- (IB): --.

In Claim 6, Column 86, Lines 37-38, delete "$C(O)Q^1NR^8C(O)Z^1Q^2Q^3—C(O)Q^1NR^8C(O)Z^1Q^2Z^2—,$" and insert -- $–C(O)Q^1NR^8C(O)Z^1Q^2Q^3–, –C(O)Q^1NR^8C(O)Z^1Q^2Z^2–,$ --.

In Claim 6, Column 86, Line 40, delete "$—C(O)NR^8Z^1Q^1, C(O)NR^8Z^1Q^1Z^2—,$" and insert -- $–C(O)NR^8Z^1Q^1–, –C(O)NR^8Z^1Q^1Z^2–,$ --.

In Claim 6, Column 86, Lines 41-42, delete "$—C(O)NR^8Q^1Q^2Z^1, C(O)NR^8Z^1Q^1Q^2Z^2,$" and insert -- $–C(O)NR^8Q^1Q^2Z^1–, –C(O)NR^8Z^1Q^1Q^2Z^2, –$ --.

In Claim 6, Column 86, Lines 42-43, delete "$—C(O)NR^8(CH_2CH_2O)_nZ^1—C(O)NR^8Z^1O(CH_2O)_nZ^2—,$" and insert -- $–C(O)NR^8(CH_2CH_2O)_nZ^1–, –C(O)NR^8Z^1O(CH_2O)_nZ^2–,$ --.

In Claim 8, Column 86, Lines 55-56, delete "$Q^1C(O)Q^2Q^3-,$ or $Q^1C(O)Q^2Q^3Z^1—,$" and insert -- $–Q^1C(O)Q^2Q^3–,$ or $–Q^1C(O)Q^2Q^3Z^1–,$ --.

In Claim 9, Column 86, Line 60, delete "-2,3,4,5, 6" and insert -- -2,3,4,5,6 --.

In Claim 9, Column 87, Line 6, delete "hexyl] amino}" and insert -- hexyl]amino} --.

In Claim 9, Column 87, Line 14, delete "6-{-1H-1,3-benzodiazol-3-ium" and insert -- 6-{[(14S,15R,16R,17R)-14,15,16,17,18-pentahydroxy-12-[(2S,3R,4R,5R)-2,3,4,5,6-pentahydroxyhexyl]-3,6,9-trioxa-12-azaoctadecan-1-yl]carbamoyl}-1H-1,3-benzodiazol-3-ium --.

In Claim 9, Column 87, Line 16, delete "hexyl] amino}" and insert -- hexyl]amino} --.